US012779469B2

(12) United States Patent
O'Neall et al.

(10) Patent No.: US 12,779,469 B2

(45) Date of Patent: Nov. 3, 2026

(54) AGRICULTURAL SAMPLE PACKAGING SYSTEM AND RELATED METHODS

(71) Applicant: Precision Planting LLC, Tremont, IL (US)

(72) Inventors: Matthew O'Neall, Ellsworth, IL (US); Todd Swanson, Morton, IL (US); Dale M. Koch, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 24 days.

(21) Appl. No.: 18/293,025

(22) PCT Filed: Sep. 7, 2022

(86) PCT No.: PCT/IB2022/058409

§ 371 (c)(1),
(2) Date: Jan. 29, 2024

(87) PCT Pub. No.: WO2023/042036

PCT Pub. Date: Mar. 23, 2023

(65) Prior Publication Data

US 2025/0074635 A1 Mar. 6, 2025

Related U.S. Application Data

(60) Provisional application No. 63/370,077, filed on Aug. 1, 2022, provisional application No. 63/370,081, filed (Continued)

(51) Int. Cl.

*B01L 3/00* (2006.01)
*B65B 1/16* (2006.01)

(Continued)

(52) U.S. Cl.

CPC ............ *B01L 3/50825* (2013.01); *B65B 1/16* (2013.01); *B65B 37/06* (2013.01); *B65B 43/60* (2013.01);

(Continued)

(58) Field of Classification Search

CPC ........... B01L 3/50825; B01L 2300/042; B01L 2300/045; B01L 2400/0478;

(Continued)

(56) References Cited

U.S. PATENT DOCUMENTS 2,558,800 A * 7/1951 Thompson ................ B65B 1/04 141/130
4,442,721 A * 4/1984 Singer .................. A01G 25/167 73/863.31

(Continued)

FOREIGN PATENT DOCUMENTS

CA 1076806 A 5/1980
CN 107192593 A 9/2017

(Continued)

OTHER PUBLICATIONS

Dale M. Koch, U.S. Appl. No. 18/350,847, filed Jul. 12, 2023, 268 pages.

(Continued)

*Primary Examiner* — Veronica Martin
*Assistant Examiner* — Mobeen Ahmed

(57) ABSTRACT

An automated programmable processor-controlled system and related methods for packaging an agricultural sample such as soil which may be tested for various chemical properties such as plant available nutrients. The packaging system includes a sample packaging apparatus which allows raw bulk sample material collected in the agricultural field to be expediently and conveniently containerized for processing and analysis. The apparatus may include a die block (Continued)

disposed between bulk material and sample collection chambers. A sample blade mechanism inserts a sample blade array through the bulk material chamber and die block. The sample blades extrude the sample material from the bulk material chamber through die slots in the die block, thereby forming plugs or blanks of the material collected in the sample collection chamber coupled to the sample container. A cleaning blade mechanism inserts a cleaning blade array through the die slots after the extrusion for removing residual soil or debris.

20 Claims, 45 Drawing Sheets

Related U.S. Application Data on Aug. 1, 2022, provisional application No. 63/370,072, filed on Aug. 1, 2022, provisional application No. 63/264,059, filed on Nov. 15, 2021, provisional application No. 63/264,062, filed on Nov. 15, 2021, provisional application No. 63/264,065, filed on Nov. 15, 2021, provisional application No. 63/245,278, filed on Sep. 17, 2021.

(51) Int. Cl.

| | |
|---|---|
| ***B65B 37/06*** | (2006.01) |
| ***B65B 43/60*** | (2006.01) |
| ***B65B 69/00*** | (2006.01) |
| ***G01N 1/00*** | (2006.01) |
| ***G01N 33/24*** | (2006.01) |
| ***G01N 35/00*** | (2006.01) |
| ***G01N 35/04*** | (2006.01) |

(52) U.S. Cl.

CPC ..... *B65B 69/0058* (2013.01); *G01N 35/0099* (2013.01); *G01N 35/04* (2013.01); *B01L 2300/042* (2013.01); *B01L 2300/045* (2013.01); *B01L 2400/0478* (2013.01); *G01N 2001/005* (2013.01); *G01N 33/24* (2013.01); *G01N 2035/0401* (2013.01); *G01N 2035/0405* (2013.01); *G01N 2035/0437* (2013.01); *G01N 2035/0465* (2013.01); *G01N 2035/0479* (2013.01)

(58) Field of Classification Search

CPC ....... B65B 69/0058; B65B 1/16; B65B 37/06; B65B 43/60; B65B 1/24; B65B 3/12; B65B 7/2821; B65B 43/54; B65B 69/005; B65B 1/30; B65B 1/36; B65B 1/363; B65B 1/38; B65B 25/02; B65B 37/00; B65B 37/16; B65B 37/20; G01N 35/0099; G01N 35/04; G01N 33/24; G01N 2001/005; G01N 2035/0401; G01N 2035/0405; G01N 2035/0437; G01N 2035/0465; G01N 2035/0479; G01N 2035/0484

See application file for complete search history.

(56) References Cited

U.S. PATENT DOCUMENTS

| | | | | | |
|---|---|---|---|---|---|
| 4,827,944 | A * | 5/1989 | Nugent | G01N 33/521 | 604/404 |
| 5,355,815 | A | 10/1994 | Monson | | |
| 5,435,399 | A * | 7/1995 | Peterson | E21B 25/005 | 175/203 |
| 6,016,713 | A * | 1/2000 | Hale | A01B 79/005 | 73/864.45 |
| 6,119,531 | A * | 9/2000 | Wendte | A01D 41/127 | 73/863.52 |
| 6,339,966 | B1 * | 1/2002 | Kalidindi | G01N 1/16 | 73/864.31 |
| 6,363,803 | B1 * | 4/2002 | Hubers | G01N 1/08 | 73/864.43 |
| 6,393,926 | B1 | 5/2002 | Bowersox, Jr. et al. | | |
| 8,205,513 | B2 * | 6/2012 | Pottmann | G01F 11/40 | 73/864.34 |
| 8,613,234 | B1 * | 12/2013 | Harrell | G01N 1/08 | 73/864.41 |
| 8,955,401 | B1 | 2/2015 | Burton | | |
| 9,116,078 | B1 * | 8/2015 | Scheiderer | G01N 1/04 | |
| 9,500,567 | B2 * | 11/2016 | Scheiderer | G01N 1/08 | |
| 10,018,612 | B2 * | 7/2018 | Baucom | G01N 33/24 | |
| 10,701,856 | B2 * | 7/2020 | Koch | A01B 79/02 | |
| 12,098,981 | B2 * | 9/2024 | Peterson | G01N 1/08 | |
| 2008/0298166 | A1 * | 12/2008 | Cartagena | G01N 1/286 | 366/140 |
| 2009/0071714 | A1 * | 3/2009 | Shrestha | A01C 21/007 | 175/20 |
| 2009/0293648 | A1 * | 12/2009 | Pottmann | G01F 11/40 | 73/864.34 |
| 2010/0037712 | A1 * | 2/2010 | Burton | E21B 49/02 | 53/284.7 |
| 2012/0241180 | A1 | 9/2012 | Renyer et al. | | |
| 2013/0028697 | A1 * | 1/2013 | Neeper | G01N 35/04 | 700/214 |
| 2013/0071944 | A1 * | 3/2013 | Ulrich | G01N 1/31 | 422/554 |
| 2014/0251032 | A1 * | 9/2014 | Scheiderer | G01N 1/04 | 73/864.43 |
| 2018/0080914 | A1 * | 3/2018 | Baucom | G01N 1/08 | |
| 2018/0124992 | A1 * | 5/2018 | Koch | G01N 33/24 | |
| 2020/0100418 | A1 | 4/2020 | Kornecki et al. | | |
| 2021/0016286 | A1 | 1/2021 | Swanson et al. | | |
| 2021/0123936 | A1 * | 4/2021 | Swanson | G01N 1/08 | |
| 2021/0208123 | A1 * | 7/2021 | Swanson | G01N 1/08 | |
| 2021/0268456 | A1 | 9/2021 | Swanson et al. | | |
| 2021/0341452 | A1 | 11/2021 | Swanson et al. | | |
| 2022/0196628 | A1 | 6/2022 | Swanson et al. | | |
| 2023/0133335 | A1 | 5/2023 | Swanson et al. | | |
| 2023/0144670 | A1 | 5/2023 | Swanson et al. | | |
| 2023/0151810 | A1 | 5/2023 | Matthew | | |
| 2023/0173415 | A1 | 6/2023 | Swanson et al. | | |
| 2023/0189696 | A1 | 6/2023 | Sauder et al. | | |
| 2024/0344935 | A1 * | 10/2024 | Royer | G01N 1/08 | |
| 2025/0074635 | A1 * | 3/2025 | O'Neall | B01L 3/50825 | |
| 2025/0155335 | A1 * | 5/2025 | Levy | G01N 1/4077 | |

FOREIGN PATENT DOCUMENTS

| | | | | |
|---|---|---|---|---|
| CN | 109085013 | A | 12/2018 | |
| DE | 3612409 | A1 | 10/1987 | |
| DE | 10140413 | A1 * | 9/2002 | B65G 1/34 |
| EP | 1970493 | A2 | 9/2008 | |
| JP | H1183696 | A | 3/1999 | |
| KR | 101084616 | B1 | 11/2011 | |
| KR | 101106075 | B1 | 1/2012 | |
| WO | WO-8707911 | A1 * | 12/1987 | C12M 33/06 |
| WO | 2021171120 | A1 | 9/2021 | |
| WO | 2021171121 | A1 | 9/2021 | |
| WO | 2021220082 | A1 | 11/2021 | |
| WO | 2021220083 | A1 | 11/2021 | |
| WO | 2021220084 | A1 | 11/2021 | |
| WO | 2021220085 | A1 | 11/2021 | |
| WO | 2022243793 | A1 | 11/2022 | |
| WO | 2022243794 | A1 | 11/2022 | |
| WO | 2022243795 | A1 | 11/2022 | |
| WO | 2022243796 | A1 | 11/2022 | |
| WO | 2022243797 | A1 | 11/2022 | |
| WO | 2022243806 | A1 | 11/2022 | |
| WO | 2022243807 | A1 | 11/2022 | |
| WO | 2022243808 | A1 | 11/2022 | |
| WO | 2022243809 | A1 | 11/2022 | |
| WO | 2022259073 | A1 | 12/2022 | |

(56) References Cited

FOREIGN PATENT DOCUMENTS

| | | | |
|---|---|---|---|
| WO | 2022269388 | A1 | 12/2022 |
| WO | 2023031725 | A1 | 3/2023 |
| WO | 2023031726 | A1 | 3/2023 |
| WO | 2023031727 | A1 | 3/2023 |
| WO | 2023042032 | A1 | 3/2023 |
| WO | 2023042033 | A1 | 3/2023 |
| WO | 2023042035 | A1 | 3/2023 |
| WO | 2023042036 | A1 | 3/2023 |
| WO | 2023042037 | A1 | 3/2023 |
| WO | 2023042038 | A1 | 3/2023 |
| WO | 2023042039 | A1 | 3/2023 |
| WO | 2023161727 | A1 | 8/2023 |
| WO | 2023161728 | A1 | 8/2023 |
| WO | 2023170480 | A1 | 9/2023 |
| WO | 2023170482 | A1 | 9/2023 |
| WO | 2023227959 | A1 | 11/2023 |
| WO | 2023227960 | A1 | 11/2023 |
| WO | 2023248015 | A1 | 12/2023 |
| WO | 2023248016 | A1 | 12/2023 |
| WO | 2024023728 | A1 | 2/2024 |
| WO | 2024023729 | A1 | 2/2024 |

OTHER PUBLICATIONS

European Patent Office, Search Report for related EP Application No. PCT/IB2022/057847, dated Nov. 11, 2022, 11 pages.

UK Intellectual Property Office, Search report for related UK Application No. GB2113489.5, dated Dec. 3, 2021, 3 pages.

* cited by examiner

AGRICULTURAL SAMPLE PACKAGING SYSTEM AND RELATED METHODS

BACKGROUND

The present application is a national phase entry under 35 U.S.C. § 371 of International Patent Application PCT/IB2022/058409, filed Sep. 7, 2022 designating the United States of America and published in English as International Patent Publication WO 2023/042036 A1 on Mar. 23, 2023, which claims priority to U.S. Provisional Patent Application No. 63/245,278 filed 17 Sep. 2021; U.S. Provisional Patent Application No. 63/264,059 filed 15 Nov. 2021; U.S. Provisional Patent Application No. 63/264,062 filed 15 Nov. 2021; U.S. Provisional Patent Application No. 63/264,065 filed 15 Nov. 2021; U.S. Provisional Patent Application No. 63/370,072 filed 1 Aug. 2022: U.S. Provisional Patent Application No. 63/370,077 filed 1 Aug. 2022; and U.S. Provisional Patent Application No. 63/370,081 filed 1 Aug. 2022. The foregoing applications are incorporated herein by reference in their entireties.

BACKGROUND

The present disclosure relates generally to agricultural sampling and analysis, and more particularly to a system for packaging and tracking an agricultural sample such as soil for chemical analysis.

Periodic soil testing is an important aspect of the agricultural arts. Test results provide valuable information on the chemical makeup of the soil such as plant-available nutrients and other important properties (e.g., levels of nitrogen, magnesium, phosphorous, potassium, pH, etc.) so that various amendments may be added to the soil to maximize the quality and quantity of crop production.

In some existing soil sampling processes, collected bulk agricultural samples such as soil or other agricultural materials may require some form of packaging to facilitate transport and further preparation and processing for eventual chemical analysis. The packaging further protects the integrity of the samples until processed. In addition, a means for tracking where samples were collected from in the agricultural field is necessary to associate the chemical analysis results with a particular portion of the field.

BRIEF SUMMARY

The present disclosure provides an automated programmable processor-controlled agricultural sample packaging system and related methods for containerizing an agricultural sample. In some embodiments, the container may be a cylindrical sample tube capped at both ends. The sample may be a soil sample in some non-limiting embodiments, or other agricultural-related materials described further herein. The packaging system may comprise a packaging apparatus which receives bulk soil sample material collected by an automated sample collection device/probe or manually, extracts portions of the material, and transfers the extracted portions to the sample container which may then be capped. The sample extraction and containerization process may be automatically controlled by a system controller which communicates with multiple sensors which monitor the operation and position of the various components of the packaging equipment to control its operation. The system may include sample tracking comprising assigning a unique tracking ID to each sample which can be correlated to the location in the agricultural field or elsewhere where the sample was obtained. In one embodiment, RFID (radio frequency identification) may be used.

Although the agricultural sample packaging system may be described herein with reference to containerizing soil samples which represents only a single category of use for the disclosed embodiments, it is to be understood that the same packaging systems including the apparatuses and related processes may further be used for processing other types of agricultural related samples including without limitation vegetation/plant, forage, manure, feed, milk, or other types of samples. The disclosure herein should therefore be considered broadly as an agricultural sample packaging system amenable for extracting and containerizing many different types of samples from bulk "as collected" sample material regardless of the method for collection. Accordingly, the present agricultural sample packaging system disclosed is expressly not limited to use of packaging soil samples alone for chemical analysis of properties of interest.

BRIEF DESCRIPTION OF THE DRAWINGS

The present disclosure will become more fully understood from the detailed description and the accompanying drawings, wherein like elements are labeled similarly and in which.

Figure 1:
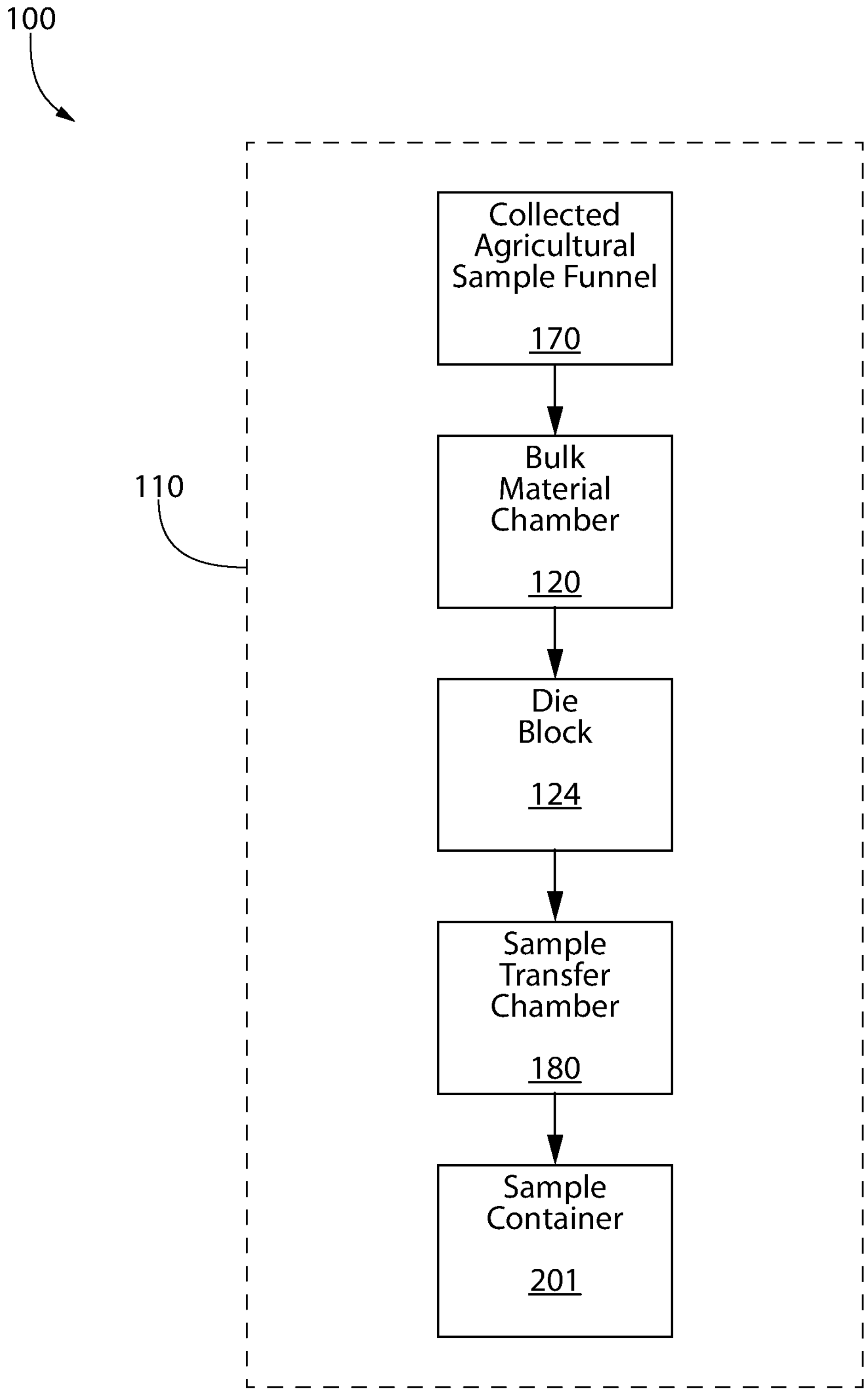
FIG. 1 is a high-level process flow chart providing a summary overview of the agricultural sample packaging process according to the present disclosure.

All drawings are not necessarily to scale. Components numbered and appearing in one figure but appearing unnumbered in other figures are the same components unless expressly noted otherwise. Any reference herein to a whole figure number which appears in multiple figures bearing the same whole number but with different alphabetical suffixes shall be constructed as a general refer to all of those figures unless expressly noted otherwise.

DETAILED DESCRIPTION

The features and benefits of the present disclosure are illustrated and described herein by reference to exemplary ("example") embodiments. This description of exemplary embodiments is intended to be read in connection with the accompanying drawings, which are to be considered part of the entire written description. Accordingly, the disclosure expressly should not be limited to such exemplary embodiments illustrating some possible non-limiting combination of features that may exist alone or in other combinations of features.

In the description of embodiments disclosed herein, any reference to direction or orientation is merely intended for convenience of description and is not intended in any way to limit the scope of the present disclosure. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise.

As used throughout, any ranges disclosed herein are used as shorthand for describing each and every value that is within the range. Any value within the range can be selected as the terminus of the range. In addition, all references cited herein to prior patents or patent applications are hereby incorporated by reference in their entireties. In the event of a conflict in a definition in the present disclosure and that of a cited reference, the present disclosure controls.

FIGS. 1-46 show one embodiment of an agricultural sample packaging system 100 and various components thereof according to the present disclosure. The packaging system may be used for and will be described for convenience with containerizing soil samples as an illustrative but not limiting use.

Packaging system 100 generally comprises agricultural sample packaging apparatus 110 defining a front 110*a*, rear 110*b*, right lateral side 110*c*, left lateral side 110*d*, top 110*e*, and bottom 110*f* for convenience of reference and not limitation. Apparatus 110 can be horizontally and laterally elongated in structure and defines a longitudinal axis LA extending horizontally through the right and left lateral sides and intersects the geometric centerline of the apparatus. An outer protective housing 116 of suitable configuration and material may be provided to protect a majority of the components of the packaging apparatus 110 including electronic components from dust, debris, direct rainfall, impacts, etc.

Packaging apparatus 110 includes a support frame 111 including an upper sub-frame 115 comprising a pair of laterally spaced apart vertical end supports 112 and one or more cross supports 113 spanning between and fixedly coupled to the end support members to form a self-supporting rigid frame structure. A lower base sub-frame 114 of the chassis 111 may be provided in some embodiments which is coupled to the upper sub-frame 115 and elevates and/or spaces the upper sub-frame above a support surface or object. Base sub-frame 114 may comprise an assemblage or weldment of plural structural members (e.g., tubes, rods, L-angles, I-beams, C-beams, etc.) configured to conform to and the mount the apparatus to a support surface or object. The support surface or object may be a stationary article or surface, or movable such as part of a self-powered or pulled wheeled vehicle (e.g., ATV, truck, trailer, etc.). Accordingly, numerous configurations of base sub-frames are possible depending on the mounting needs.

Upper sub-frame 115 of support frame 111 provides a mounting platform for and supports the functional and movable electronic and non-electronic components of the packaging apparatus 110. In one embodiment, the apparatus generally comprises a bulk material chamber 120, a sample transfer or collection chamber 180, a sample blade mechanism 130, a cleaning blade mechanism 140, a compaction piston-plunger 150, sample transfer piston-plunger 155, an optional container end cap actuator 160, funnel 170 with associated funnel door 171 and door actuator 172, and a rotatable container carousel 200 configured to removably hold the sample container 201 for the soil sample filling operation.

In the non-limiting illustrated embodiment, agricultural sample container 201 may be a hollow cylindrical sample tube 202 having a construction and customized features adapted for use with packaging apparatus 110 to containerize agricultural samples such as soil samples or others. Accordingly, sample tube 202 is distinguishable from ordinary tubes which may have capped ends.

Sample tube 202 has an elongated cylinder hollow body terminated by opposite having a top end 203*a* and bottom end 203*b* closed and sealed by a pair of circular end caps 204. Caps 204 may be made of metallic or non-metallic (e.g., plastic or other) materials. In one embodiment, the tube body and caps 204 are formed of plastic. One end cap 204*a* may be a fixed or stationary cap configured for detachable coupling to top end 203*a* of the container 201. The other remaining end cap may be a movable push-pop end cap 204*b* which is slideably received inside the tube 202 adjacent to bottom end 203*b* of the tube. Push-pop cap 204*b* is slideably moveable from end 203*b* of the tube towards the other end 203*a* and vice-versa during the tube fill operation. Bottom end 203*b* of tube 202 in some embodiments may include anti-rotation features to rotationally lock the tube in position when mounted to the packaging apparatus 110, as further described herein.

One unique aspect of sample tube 202 is push-pop cap 204*b* which includes a plurality of downwardly and outwardly projecting spring-action retention protrusions 205 configured to slideably engage the interior walls of the sample tube 202. Retention protrusions 205 may be separately mounted to the perimeter and peripheral edge of cap 204*b*, or may be integrally formed as part of a single monolithic unitary cap structure as illustrated herein. In one preferred but non-limiting embodiment, the push-pop cap 204*b* and retention protrusions 205 may be such a one-piece unitary structure made of a suitable semi-rigid but resiliently deformable plastic material having an elastic memory (e.g., polyethylene, polypropylene, etc.). Retention protrusions 205 in other embodiments, however, may be separate elements formed of spring metal or resilient deformable plastic affixed to cap 204*b*.

In one embodiment, retention protrusions 205 may each have a somewhat squared-off or U-shaped configuration as shown; however, other shaped retention protrusions may be used and the shape does not limit the invention. This gives the push-pop cap 204*b* a somewhat castellated shape. The free terminal ends 205*a* of the retention protrusions may be outwardly flared forming tabs which can positively engage corresponding complementary configured arcuately curved and elongated retention slots 202*c* of sample tube 202. This gives the protrusions 205 a somewhat L-shaped configuration with the protrusions appearing as downwardly extending legs from cap 204*b* with out-turned ends. Slots 202*c* are oriented cross-wise in the tubular sample tube body perpendicularly to its cylindrical wall. The protrusions 205 may be circumferentially spaced apart as shown around the entire perimeter and periphery of the push-pop cap 204*b*. Six retention protrusions 205 may be provided in one non-limiting embodiment; however, fewer or more protrusions may be provided.

The circumferentially elongated retention slots 202*c* formed in the cylindrical walls 202*a* of the sample tube 202 are selectively engageable with retention protrusions 205*a* to lock or unlock the push-pop cap 204*b* from the sample tube depending on the position of the cap inside the tube. Cap 204*b* therefore is sized in diameter to be fully inserted inside the interior space of the sample tube whereas cap 204*a* is sized larger for affixation to the top end of the tube. Slots 202*c* may be through slots in one embodiment extending completely through the walls of the tube. Retention slots 202*c* are disposed proximate to bottom end 203*b* of sample tube 202 and spaced slightly inwardly from the end of the tube. The opposite end of the tube receives fixed/stationary cap 204*a*. When sample tube 202 is placed in the carousel 200, the end of the tube with the retention slots 202*c* is preferably located at bottom for engagement with container end cap actuator 160 in some embodiments as further described herein.

Sample tube 202 may be formed of plastic, metal, or other suitable materials. In one preferred but non-limiting embodiments, the tube is made of plastic (e.g., polyethylene, polypropylene, etc.). The elongated tube body may be opaque or clear; the latter one allowing the sample to be visually inspected. Although the tube 202 is disclosed as being cylindrical in shape, other shapes and forms of sample containers may be used in other possible embodiments.

Bulk material chamber 120 and sample collection chamber 180 are each vertically-elongated hollow vessels located adjacent to each other and separated by an adjoining vertically-elongated die block 124 interspersed therebetween. Die block 124 forms a central division wall separating the chambers 120, 180 and comprises a set of vertically spaced apart die slots 124*a* extending completely therethrough and between the bulk material chamber and sample collection chamber. Slots 124*a* penetrate each of the chambers 120, 180 and are horizontally elongated in the front to rear direction. Die block 124 includes a flat wall side 124*b* which forms part of bulk material chamber 120 and opposite arcuately curved wall side 124*c* which forms part of sample collection chamber 180 as shown (see, e.g., FIGS. 42-43). Thus, because the flat wall side 124*b* forms part of the bulk material chamber 120 and the arcuately curved wall side 124*c* forms part of the sample collection chamber 180, the die block 124 forms a fixed wall relative to the bulk material chamber 120 and the sample collection chamber 180.

Figure 42:
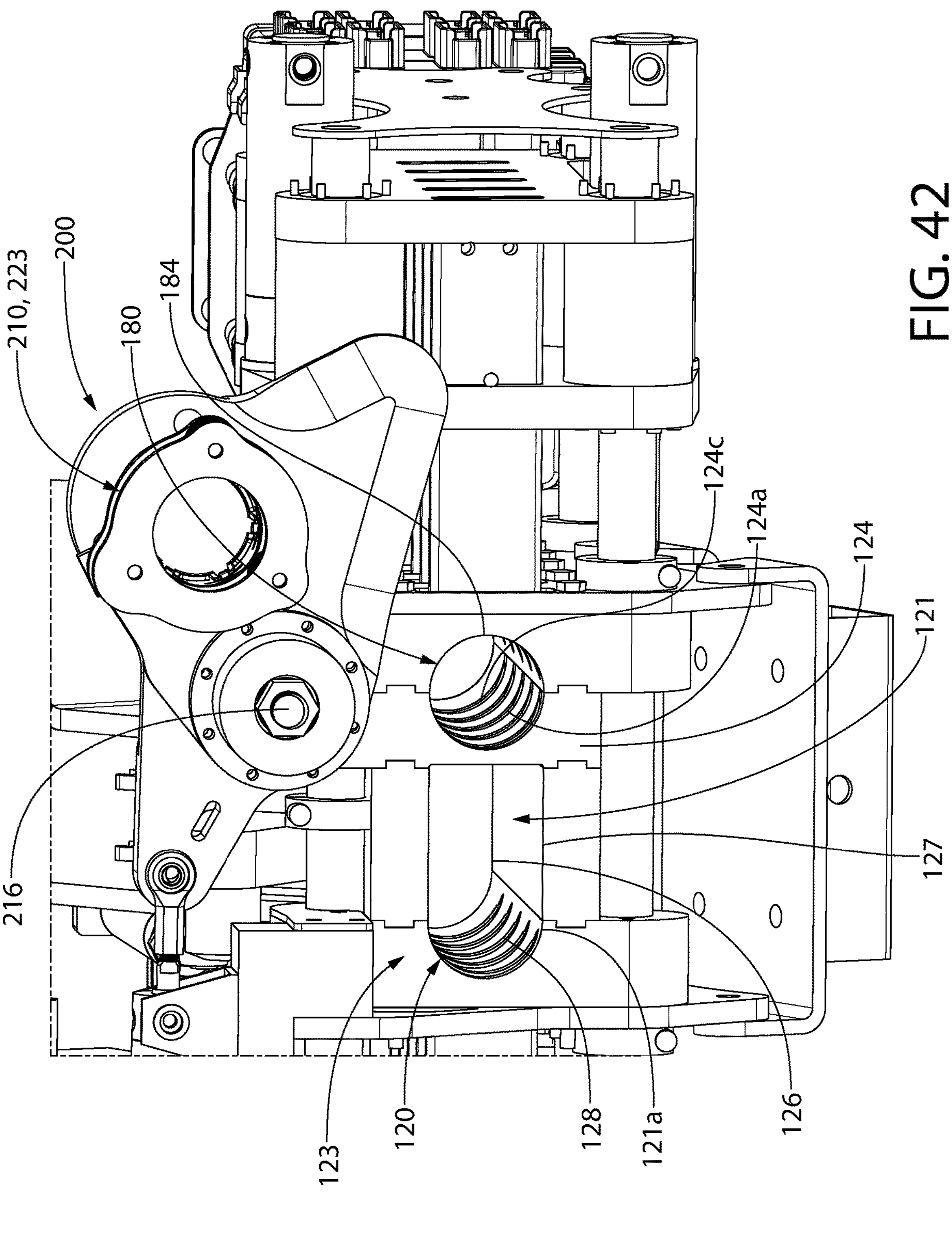
FIG. 42 is a first bottom perspective view thereof.
Figure 43:
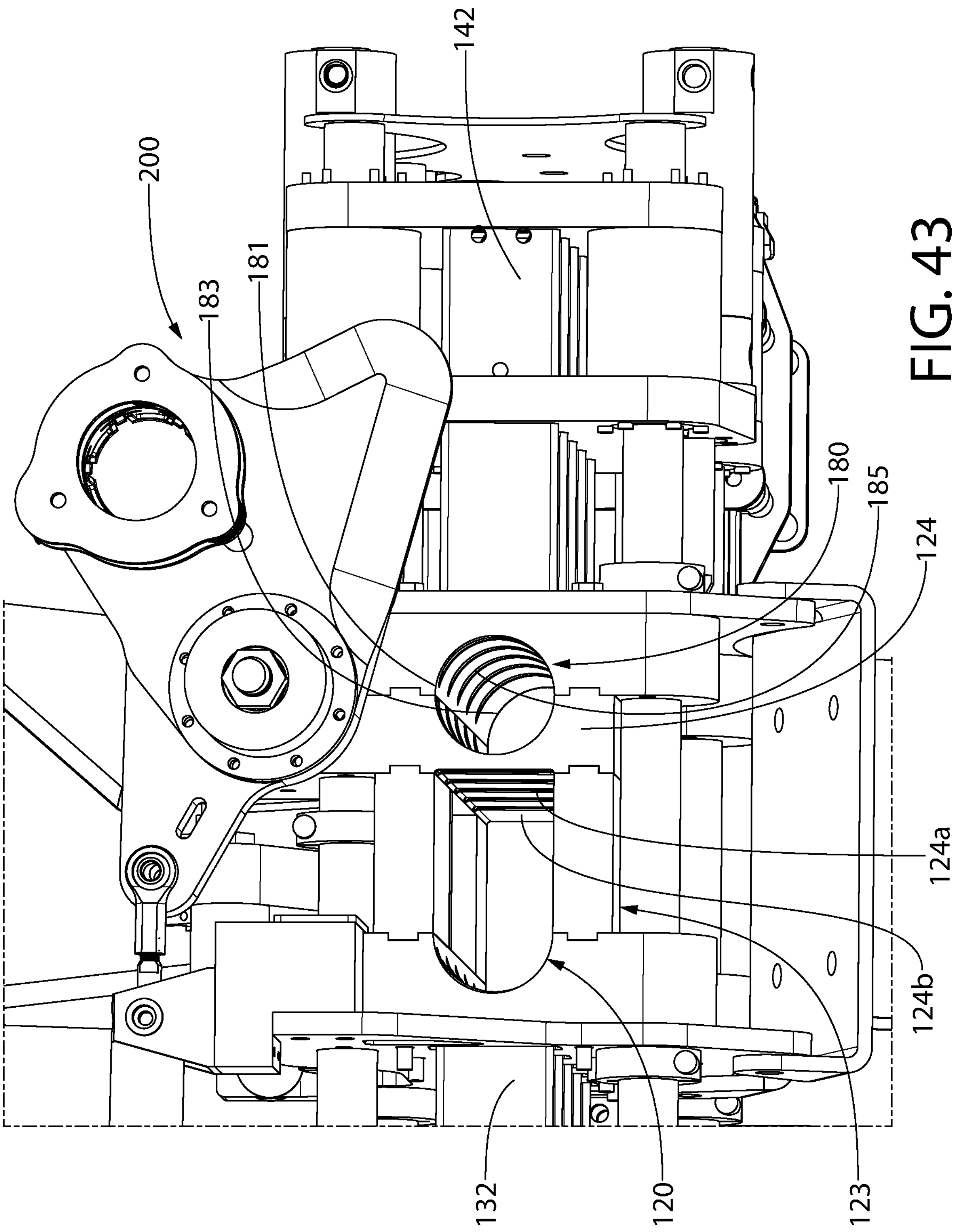
FIG. 43 is a second bottom perspective view thereof.
Figure 44:
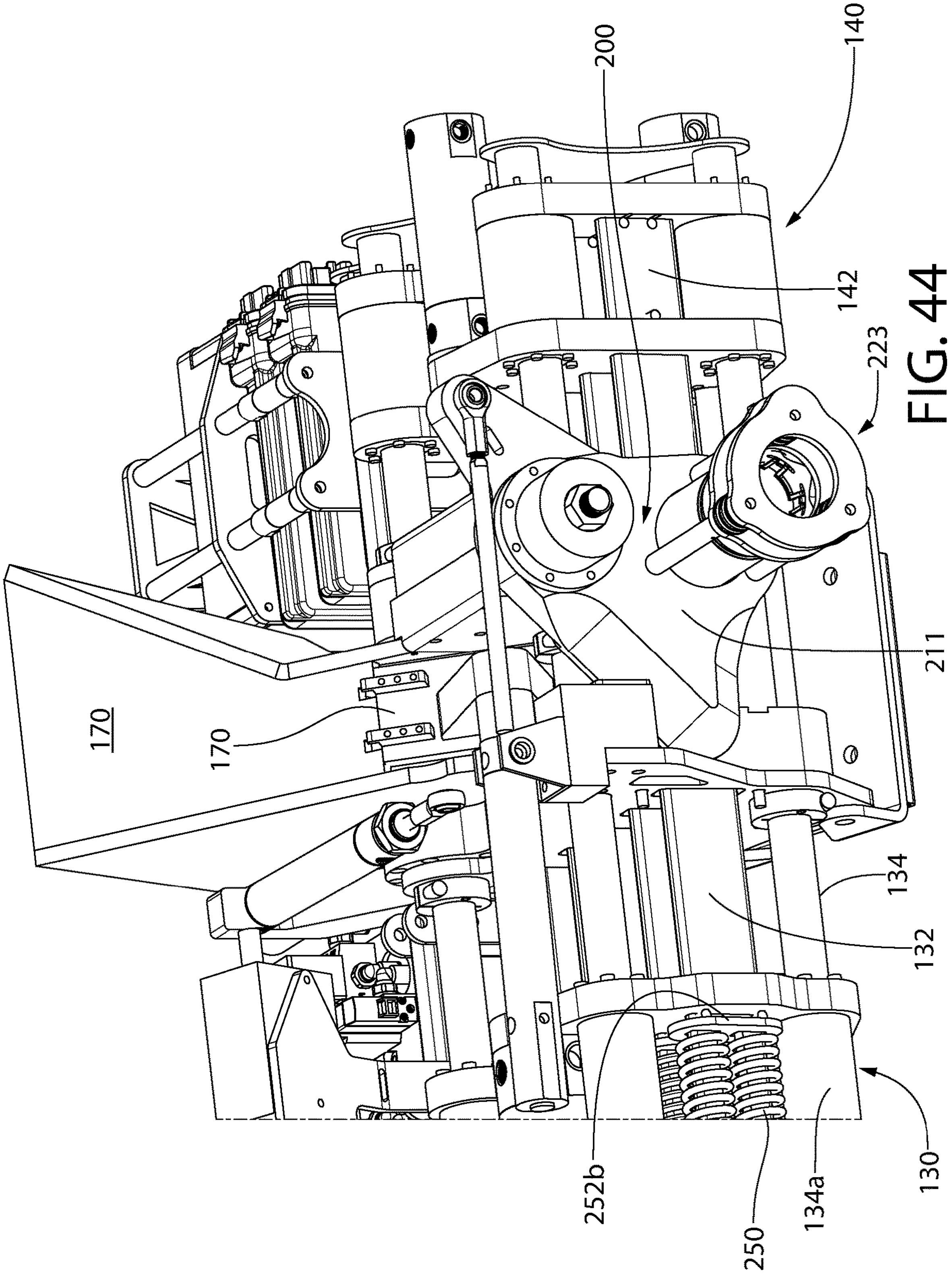
FIG. 44 is an enlarged bottom perspective view of the carousel of the apparatus.
Figure 45:
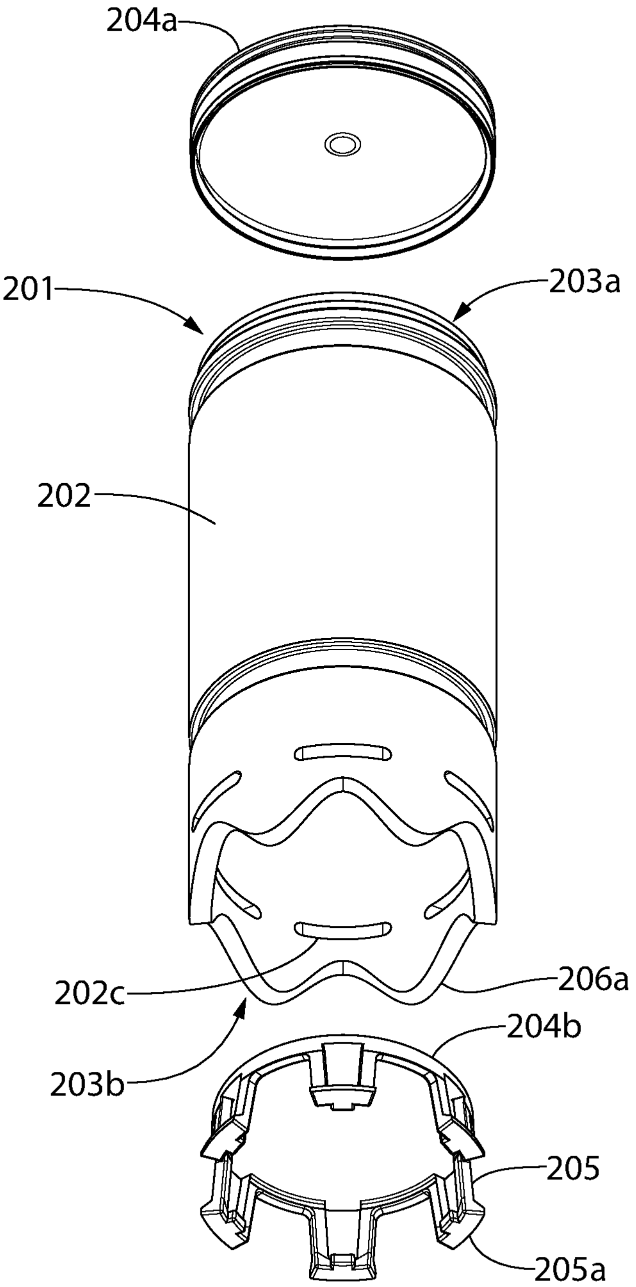
FIG. 45 is a bottom exploded perspective view of the sample container.

Chambers 120, 180 may be formed in separate chamber blocks 123 in one embodiment comprising blocks of solid material coupled to opposite sides of die block 124 (see, e.g., FIGS. 42-43. This construction allows the sample and cleaning through slots in the chamber blocks associated with the chambers 120 and 180 to be pre-fabricated prior to coupling to the die block. Chamber 180 may be partially formed in part of die block 124 such that the curved right wall side 124*c* of the die block forms part of the chamber 180 walls (see, e.g., FIGS. 42-43). Chamber block 123 and die block 124 are supported by upper sub-frame 115 between the ends of the packaging apparatus 110 as shown.

Figure 24:
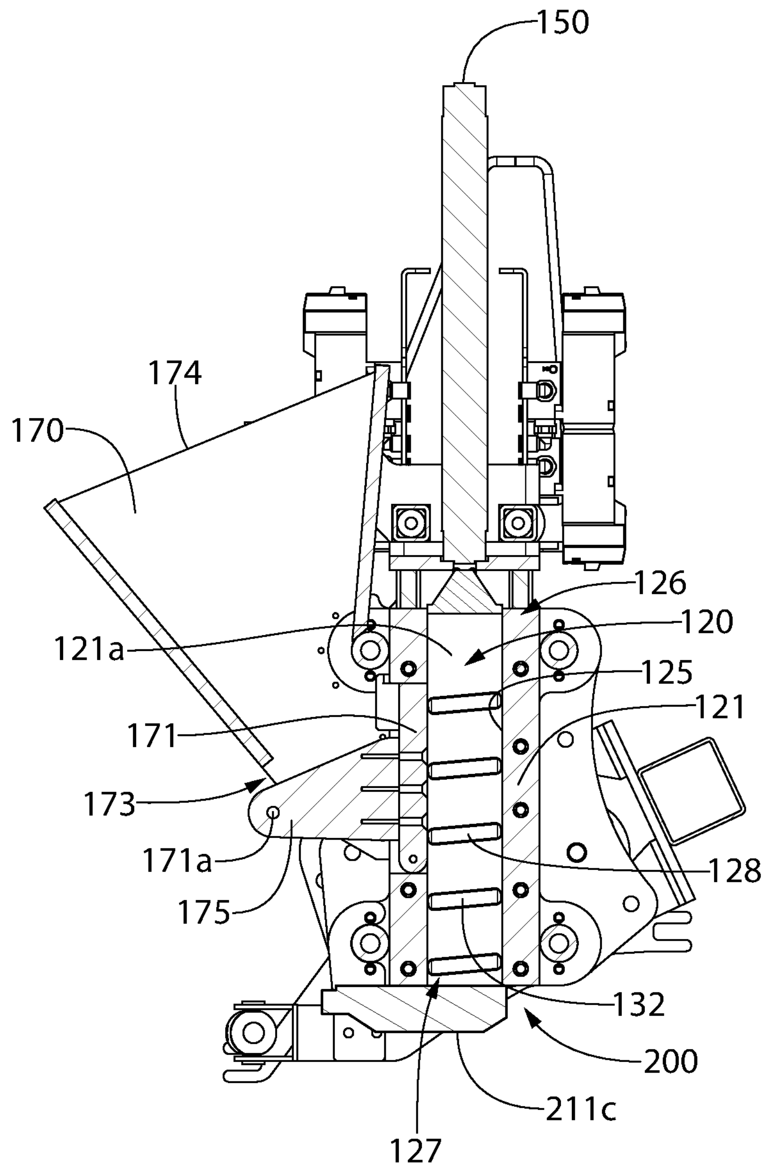
FIG. 24 is a side cross-sectional view of the apparatus showing the funnel door of the funnel in the closed position.
Figure 25:
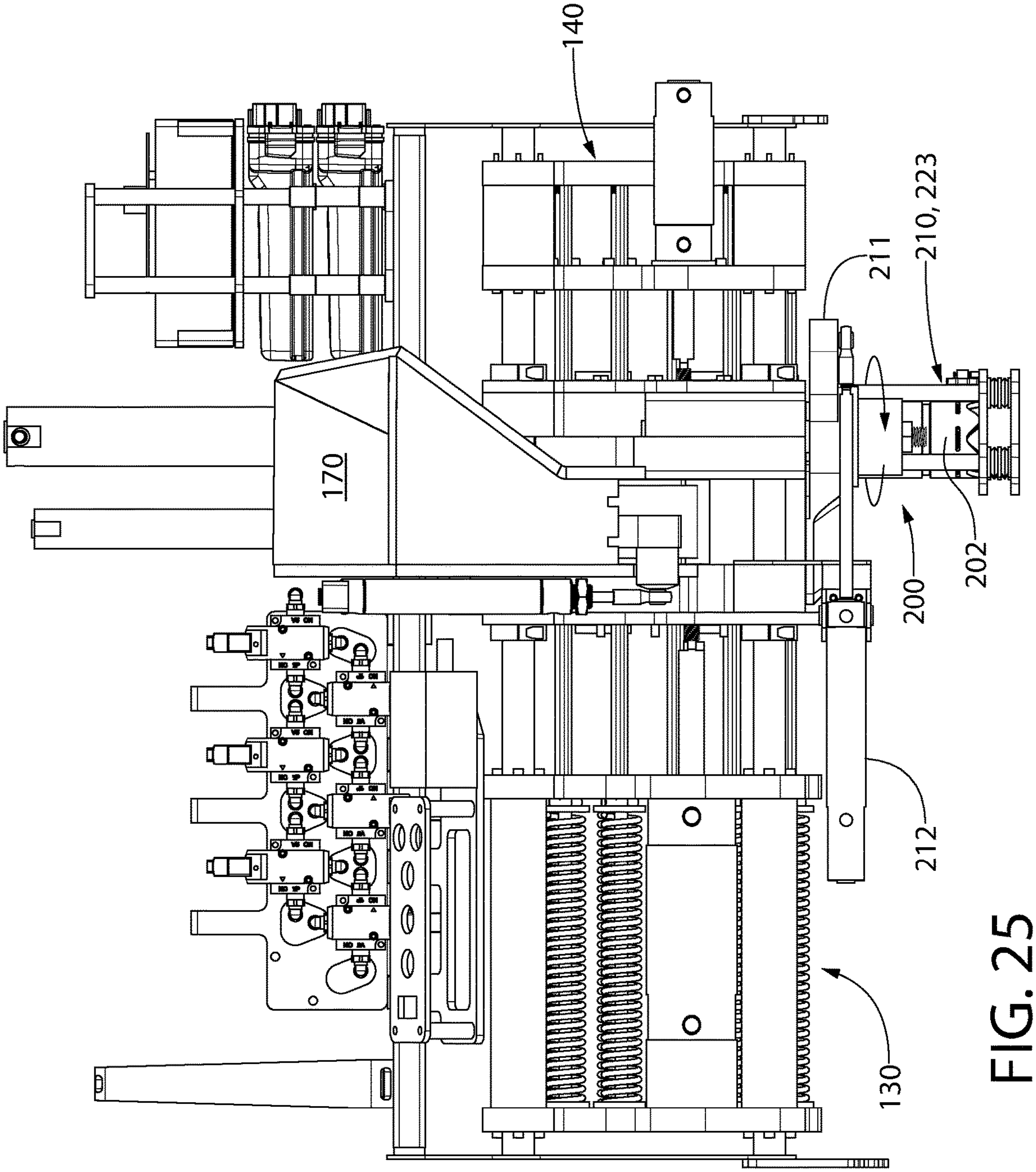
FIG. 25 is a front cross-sectional view of the apparatus showing the carousel and sample container rotated to the inward closed position ready for filling with the agricultural sample material.

Bulk material chamber 120 has a vertically-extending hollow body comprising sidewalls 121 defining an internal cavity 125, a top 126, and a bottom 127 (see, e.g., FIG. 24). The bottom 173 of funnel 170 is coupled to cavity 125 through the sidewalls 121 of chamber 120 to introduce the bulk soil sample material. In one embodiment, chamber 120 has an oblong transverse cross-sectional shape which is horizontally elongated in the axial longitudinal direction parallel to longitudinal axis LA (see, e.g., FIGS. 41-43). Sidewalls 121 may comprise an arcuately curved wall section 121*a* opposite the flat wall side 124*b* of die block 124 which forms part of the sidewalls of chamber 120. Wall section 121*a* comprises a set of vertically spaced apart blade slots 128 extending completely therethrough to slideably receive sample blades 131 of the sample blade mechanism 130. Slots 128 are positionally synchronized with and diametrically opposite die slots 124*b* such that each slot 128 is horizontally axially aligned with a corresponding die slot 124*a*.

Sample collection chamber 180 has a cylindrical configuration and vertically-extending hollow body comprising sidewalls 181 defining an internal cavity 182, a top 183, and a bottom 184. In one embodiment, chamber 180 has a circular transverse cross-sectional shape. Sidewalls 181 comprise a set of vertically spaced apart blade slots 185 extending completely therethrough to slideably receive cleaning blades 141 of the cleaning blade mechanism 140. Slots 185 are positionally synchronized with and diametrically opposite die slots 124*b* in curved wall side 124*c* of die block 124 such that each slot 185 is axially aligned with a corresponding die slot 124*b*.

Sample blade mechanism 130 comprises a chassis 131 and plurality of sample blades 132 fixedly coupled to the chassis in a vertically spaced apart array. Chassis 131 may include a pair of horizontally spaced apart right and left vertical end plates 133 at each end. Sample blades 132 may be slideably coupled to the left end plate 133*a* of the pair and slideably pass through complementary configured holes in a right end plate 133*b*. The right and left end plates are each rigidly connected together by horizontally oriented tubular guide rod sleeves 134*a* so that the chassis moves right and left as a single unit with the sample blades 132 and end plates 133.

Chassis 131 is slideably carried by a plurality of guide rods 134 each spanning laterally between and coupled to the vertical end supports 112 of frame 111 at one end and the chamber block 123 located therebetween at the other end of the rods. Guide rods 134 are slideably received inside the hollow tubular guide rod sleeves 134*a* of the chassis described above. Two sets of four guide rods 134 in each set may be provided in one embodiment which are vertically and horizontally spaced apart from each other top to bottom and front to rear as shown. One set is for slideably supporting the sample blade chassis 131 and the other is for slideably supporting sample transfer blade chassis 141. Each set of guide rods 134 may include a pair of upper and lower guide rods; each of which have an associated guide rod sleeve 134*a* of chassis 131 and guide rod sleeve 144*a* of chassis 141.

Sample blades 132 may each have a horizontally elongated bar-like body terminated by a concave terminal end 132*a* which passes through bulk material chamber 120 and die block 124 during the tube filling operation. End 132*a* has a radius of curvature (concave) which corresponds to the radius of curvature of the sample collection chamber 180 to form part of the walls of the chamber when inserted through die block 124, as further described herein. In some embodiments, the blade bodies may be arcuately curved from side to side between the longitudinal long sides of the blade 132. In other embodiments, the blade bodies may be flat. Sample blades 132 are axially and laterally moveable in the horizontal longitudinal direction between a retracted position withdrawn from bulk material chamber 120 and die block 124, and a projected position extending through the chamber 120 and die block 124. When projected, the blades extract and extrude/push soil sample material blanks or plugs from the bulk material chamber 120 through the die block 124 and into the sample collection chamber 180. In the retracted position, the concave ends 132*a* of blades 132 are flush with and form part of the arcuate curved wall section 121*a* of the bulk material chamber 120.

Sample blade mechanism 130 comprises an actuator 135 which linearly moves the chassis 131 and array of sample blades 132 supported thereby between the retracted and projected positions. Actuator 135 may be any suitable commercially-available electric linear rod actuator, pneumatic actuator, or hydraulic actuator with retractable/extendible operating rod 136 coupled to the chassis 131.

Sample blades 132 may be vertically stacked and spaced apart in one embodiment as shown. The chassis 131 to which they are mounted moves all the sample blades in unison between the retracted and projected positions.

According to one aspect of the sample blade mechanism 130, a spring-biased protection system may be provided to protect the sample blades 132 and mechanism from damage in the event one or more die slots 124*a* in die block 124 are plugged by foreign debris such as stones/rocks wedged into the die slots from a previous sample material extrusion run. In one embodiment, each sample blade 132 is mounted in a corresponding blade spring pack 253 comprising a pair of springs 250. Referring to FIGS. 20-23, the distal end portion of blades 132 (farthest from bulk material chamber 120) is bifurcated into a pair of longitudinally elongated legs 251; each of which captures a coiled compression spring 250 therearound. The proximal end of each spring 250 may be braced against and acts on an elongated proximal spring plate 252*a* slideably coupled to the blade 132 between its distal and proximal end. Proximal spring plate 252*a* abuttingly engages right end plate 133*b* of chassis 131 when mounted therein. The remaining distal end of each spring may be braced against a second elongated distal spring plate 252*b* which abuttingly engages the left end plate 133*a* of chassis 131. The bifurcated distal end of the blades 132 are projectible through corresponding openings in left distal spring plate 252*b* and left end plate 133*a* of the chassis in the event the blade encounters blockage of its respective die slot 124*a* in die block 124 when the sample blade mechanism 130 attempts to insert the blade through the slot. In operation, the remaining blades 132 whose paths are not blocked in die block 124 will continue to advance into the bulk material chamber 120 to extract soil sample material while the blocked blade will remain stationary as the chassis moves towards chamber 120 to the right. The springs associated with the blocked blade or blades 132 will be compressed and the blocked blade will not advance any farther towards the bulk material chamber. Advantageously, the sample blade mechanism will continue to function and extract samples even in the event one or more sample blade paths are blocked so that the soil sample material packaging operation is not interrupted.

The spring force (k) of springs 250 is selected to allow the sample blades 132 to be inserted through the die slots 124*a* of die block 124 with a reasonable maximum amount of force determined to prevent damage to the blades and cleaning blade mechanism 140. When this predetermined maximum force limit is exceeded as a blade encounters a blocked or plugged die slot, the springs 250 will compress to arrest progress of the blade and prevent damage to the blade and the mechanism.

Cleaning blade mechanism 140 may be generally similar to the sample blade mechanism 120 in construction and operation; however, the cleaning blades 142 enter the sample collection chamber 180 and die block 124 from the opposite direction to removed and clean residual soil deposits from the die block slots 124*a* in preparation for the next tube filling operation. Briefly, without undue repetition, cleaning blade mechanism 140 also comprises a chassis 141 supporting the plurality of cleaning blades 142 fixed coupled to the chassis in a spaced part array. Chassis 141 is slideably carried by the same type hollow tubular guide rod sleeves 144*a* which travel on guide rods 144 spanning laterally between and coupled to the vertical end supports 112 of frame 111 and chamber block 123. Chassis 141 also includes a pair of horizontally spaced apart vertical end plates 143. Cleaning blades 142 may be fixedly coupled to a right end plate 143*a* of the pair and slideably pass through complementary configured holes in a left end plate 143*b*. The blades may optionally be fixedly connected to the left end plate as well in some embodiments.

It bears noting that the cleaning blades 142 preferably do not include a spring protection mechanism like the sample blades 132. Since the function of the cleaning blades includes dislodging any debris (e.g., stones/rocks, hardened agricultural clumps, etc.) from the die block die slots 124*a*, it is preferred that the cleaning blades can be advance with full force through the die slots in a rigidly supported manner. It is therefore desirable in some embodiments for the cleaning blades 142 to not have the spring-operated relieving feature. If the cleaning blades are unable to forcefully dislodge an object obstructing one or more die slots 124*a*, the sample extraction cycle will stall (e.g., cleaning blade mechanism 140), which is detected by sample packaging machine controller 2811 via an appropriately configured sensor 2811*c* (see, e.g., FIG. 26) configured to detect that the sample blades have not fully advance and been inserted in the die slots. A positional or proximity sensors may be used for this purpose of the types similar to full tube sensor 220 described elsewhere herein, or other type sensors. The controller will electronically "time out" the cycle, indicating to the operator there is an internal problem. If a foreign object were allowed to stay lodged in the die block and the extraction cycle continues, damage will result to internal components of the apparatus mechanism. The controller 2811 communicates (e.g., visually and/or audibly) the "time out" condition to the human operator via an appropriate alarm signal so the operator is made aware of and can remedy the die block obstruction issue to restore normal operation.

Figure 20:
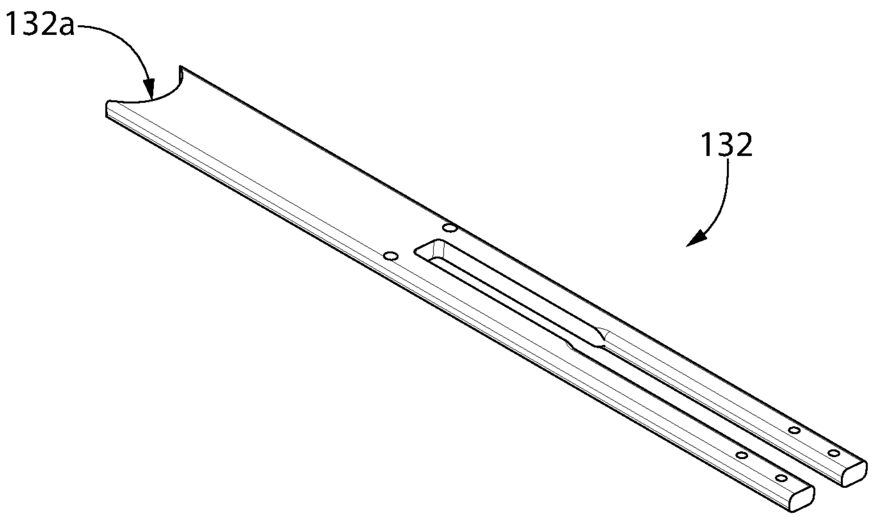
FIG. 20 is a top perspective view of a sample blade.
Figure 21:
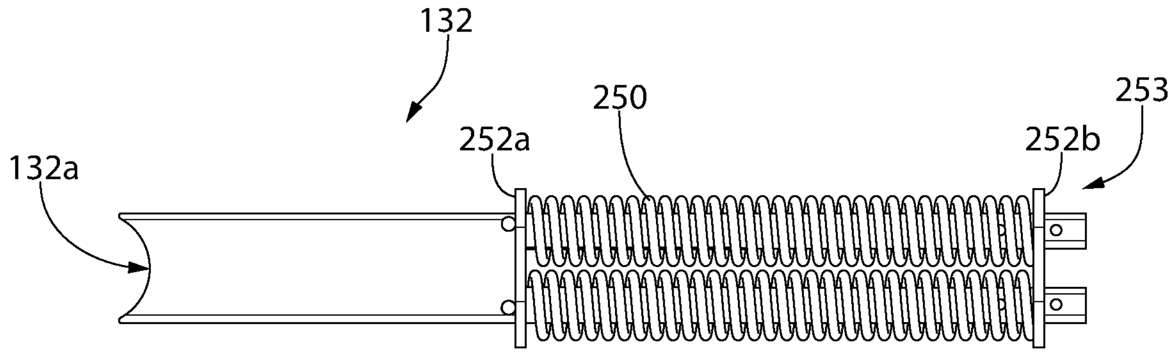
FIG. 21 is a top view of the sample blade showing a spring pack associated with the blade.

Cleaning blades 142 may have the same shape as sample blades 132 at least in cross section since they pass through the same horizontally elongated slots 124*a* in the die block 124 to remove residual soil therefrom, as further described herein. FIGS. 20 and 21 showing sample blades 132 may also represent cleaning blades 142 in shape and construction except the cleaning blade do not bifurcated ends because not spring protection mechanism is provided. Cleaning blades 142 also may each have a horizontally elongated bar-like body terminated by a concave terminal end 142*a* which passes through sample collection chamber 180 and die block 124 during the die cleaning operation. In some embodiments, the blade bodies may be arcuately curved between the longitudinal long sides. In other embodiments, the blade bodies may be flat. Cleaning blades 142 are axially and laterally moveable in the horizontal longitudinal direction between a retracted position withdrawn from chamber 180 and die block 124, and a projected position extending through the chamber 180 and die block 124. This pushes residual soil in slots 124*a* of die block 124 back into the bulk material chamber 120 from which they can be purged. In the retracted position, the concave ends 142*a* of blades 142 are flush with and form part of the arcuate curved sidewalls 181 of the sample collection chamber 180.

Cleaning blade mechanism 140 comprises an actuator 145 which linearly moves chassis 141 with the array of cleaning blades 142 supported thereby between the retracted and projected positions. Actuator 145 may be any suitable commercially available electric linear rod actuator, pneumatic actuator, or hydraulic actuator with retractable/extendible operating rod 146 coupled to the chassis 141.

Cleaning blades 142 may be vertically stacked and spaced apart in one embodiment as shown. The chassis 141 to which they are mounted moves all the cleaning blades in unison between the retracted and projected positions. The cleaning blades 142 are positionally synchronized with the die slots 124*a* such that each blade is axially and horizontally aligned with a corresponding one of the die slots.

The sample and cleaning blades 132, 142 as well as the structural components of the sample and cleaning blade mechanisms 130, 140 (e.g., end plates, guide rods and sleeves, etc.) described above preferably are made of a suitably strong metallic material, such as steel or stainless steel in some embodiments. Other suitable materials may be used.

Compaction piston-plunger 150 and sample transfer piston-plunger 155 may each be any suitable type commercially available electric linear rod actuator, pneumatic cylinder, or hydraulic cylinder with retractable/extendible operating rod 151*a* and 151*b*. Rods 151*a*, 151*b* are terminated with a disk 152*a*, 152*b* respectively; each being configured to fit closely and conform to the shape and internal diameters of the bulk material chamber 120 and sample chamber 180 without any appreciable gaps between the disks and chamber walls. Disks 152*a*, 152*b* are sized such that the peripheral edges of the disks are located adjacent to their respective chamber walls to scrape any soil away from the walls as the disks slide upwards/downwards in their chambers. Disk 152*a* of compaction piston-plunger 150 has an oblong transverse cross-sectional shape which corresponds to the oblong cross-sectional shape of bulk material chamber 120. Disk 152*b* of sample transfer piston-plunger 155 has a circular transverse cross-sectional shape which corresponds to the circular cross-sectional shape of the sample collection chamber 180.

Piston-plungers 150, 155 are each vertically oriented in one embodiment and enter the open tops of chambers 120, 180. In operation, the piston-plungers are each linearly moveable from a retracted upward position withdrawn from chambers 120 or 180, or projected downward position extending to the bottom end of the chambers. The exposed bottom surfaces of each disk 152*a*, 152*b* may be substantially flush with the bottom end faces of the chambers 120, 180 to ensure all soil is purged from the chambers and to allow the lower disk faces to be scraped/wiped clean via operation of the carousel, as further described herein.

Funnel 170 provides a hopper-type vessel into which the bulk soil sample is filled for transfer to the bulk material chamber 120. Housing 116 includes an annular chute 170*a* positioned over and optionally detachably coupleable to and partially insertable into the top of the funnel for guiding the agricultural sample material (e.g., soil or other) into the funnel. Chute 170*a* may comprise sloping walls in some embodiments as shown to facilitate adding the sample material to the funnel. In certain embodiments, the sloping walls of funnel 170 and chute 170*a* may be comprised of a nonstick material such as UHMW-PE or similar, and/or be coated to encourage sample material to flow through and not adhere to the walls. This may be particularly beneficial when processing sticky type soils such as clay.

The funnel 170 may have any suitable configuration and gradually narrows in width from the open top 174 for adding the soil sample to the funnel to the bottom 173 under control of an openable/closeable funnel door 171 coupled to door actuator 172. In one embodiment, funnel 170 may be trapezoidal shaped as shown. Other funnel shapes including frustoconical shaped funnels may be used. Funnel door 171 is pivotably and hingedly mounted to the lower portion of the funnel via hinge pin 171*a* and coupled to an eccentric cam lever 175 operably coupled to actuator 172. Funnel door 171 is pivotably moveable via operation of actuator 172 between a closed position for filling the funnel 170 with the bulk soil sample material, and an open position for transferring the soil to bulk material chamber 120. The actuator 172 may be any suitable commercially available electric linear rod actuator, pneumatic actuator, or hydraulic actuator with retractable/extendible operating rod 176 coupled to the cam lever 175.

Container carousel 200 is configured to removably hold and rotatably move the sample container 201 inwards under the sample chamber 180 and outwards therefrom during the soil sample packaging operation. Carousel 200 is rotatably mounted about a vertical pivot axis PA under packaging apparatus 110 and positioned below and proximate to the bottom ends of the bulk material chamber 120 and sample chamber 180. The carousel generally includes a rotatable base member 211 supporting a container holder 210 and carousel actuator 212 coupled to the base member. The base member 211 in one embodiment may comprise a generally broad and flat plate-like monolithic structure having a compound configuration including outwardly extending eccentric cam arm 211*a*, container support arm 211*b*, and a solid closure arm 211*c*. Pivot axis PA is formed by a pivot pin 216 extending vertically through the base member 211 and offset from the geometric center of the plate. Base member 211 is rotatably movable about pivot axis PA in a horizontal reference plane defined by pivot pin 216 which mounts the base member to the support frame 111.

Solid closure arm 211*c* is rotatable underneath and adjacent to the normally open bottom end of bulk material chamber 120 to selectively close or open the bottom end of the chamber via rotation of base 211, as further described herein. The top surface of at least the closure arm 211*c* is preferably flat to form relatively tight closure of chamber 120 at bottom to prevent the bulk soil from falling through the chamber. Closure arm 211*c* slideably moves into and out of position against the bottom end of chamber 120. This advantageously helps clean and remove any soil residue at the bottom of the chamber 120 between tube filling cycles via a wiping/scraping type action across the bottom face of the chamber.

Container holder 210 may be a generally cup-shaped structure in one embodiment supported by base member 211. In one non-limiting embodiment, the holder includes a circular opening formed in the container support arm 211*b* of the base member to receive sample tube 202 and a circular support disk 213 suspended below support arm 211*b* in a vertically spaced apart manner by a plurality of vertically elongated spacer rods 214. The container holder 210 is configured via positioning of support disk 213 such that a majority of the height of the sample tube 202 is located below the base member 211 as shown. This ensures that the tube is held by the container holder in a stable manner both during the tube sample filling operation and during rotation of the tube with the base member 211. Other forms and configurations of container holder 210 are possible so long as the sample tube 202 can be removably held with the required degree of stability.

Sample tube 202 may be configured to be rotationally locked in position to support disk 213 to ensure the tube does not rotate and remains rotationally stable during the tube filling operation and movement of the base member 211 of carousel 200. In one embodiment, the bottom end 203*b* of the cylindrical walls 202*a* of tube 202 may have an arcuately undulating castellated configuration to form a rotational interlock with a mating arcuately undulating castellated feature on the support disk 213. Accordingly, the bottom end 203*b* of sample tube 202 adjacent to where retention slots 202*c* are formed in the tube may comprise anti-rotation protrusions 206*a* which locking engage a ring of mating anti-rotation protrusions 206*b* on the tube support disk 213. The protrusions 206*a*, 206*b* may have rounded ends with sloping sides in some embodiments as shown to help guide the sample tube 202 onto the castellated support disk 213. In other embodiments, the anti-rotations features may be omitted where it might not be necessary or desirable to rotationally lock the sample tube 202 into the packaging apparatus 110 during the filling operation.

Figure 46:
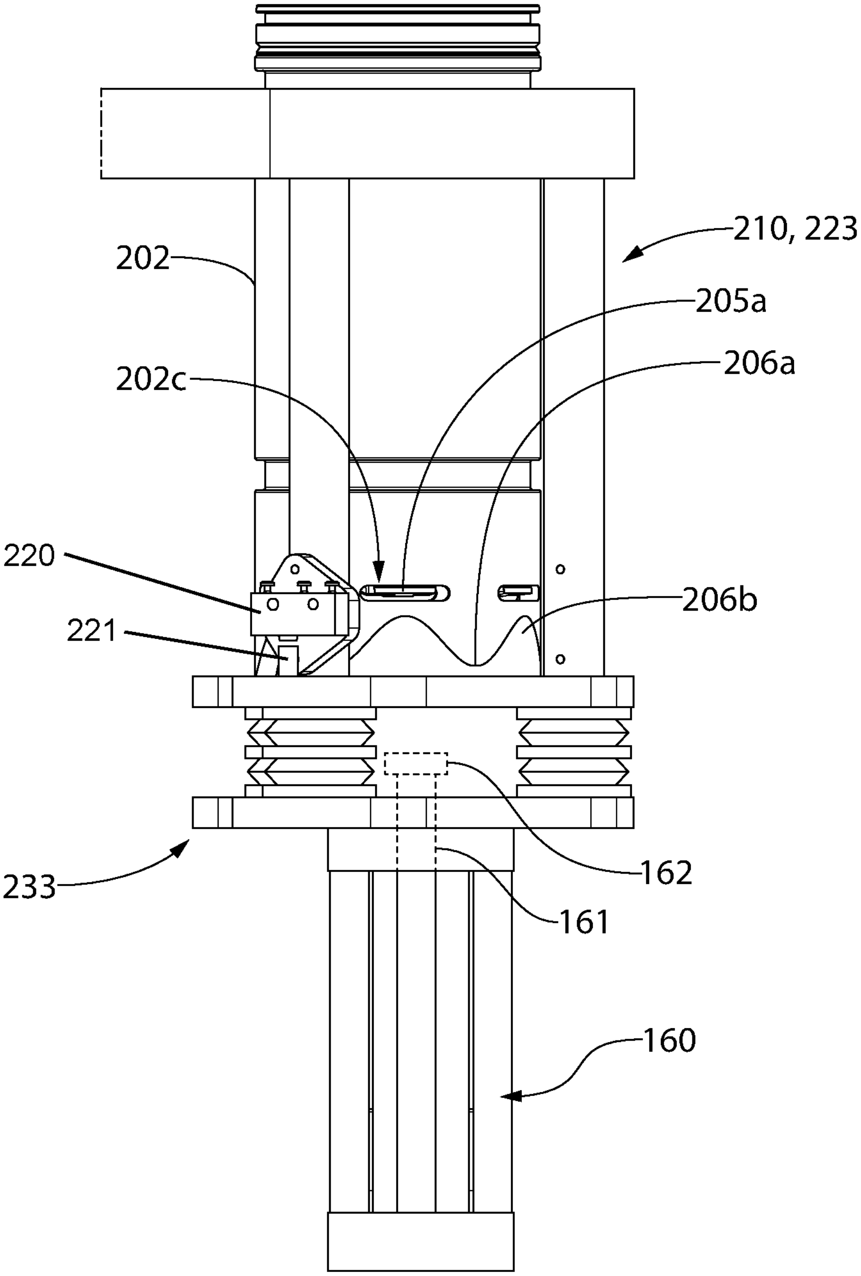
FIG. 46 is a side view of the collapsible embodiment of the cup hold of the carousel showing the push-pop cap actuator.

In one embodiment, container end cap actuator 160 may be mounted to support disk 213 of container holder 210 (FIG. 19), or alternatively collapsible dual support plate assembly 233 of alternative container holder 223 (see, e.g., FIG. 46). Cap actuator 160 is therefore rotatable with base member 211 of carousel 200. The cap actuator 160 may be any suitable commercially available electric linear rod actuator, pneumatic actuator, or hydraulic actuator with retractable/extendible operating rod 161 which is projectable through a complementary configured opening in the support disk 213 to engage and activate the push-pop cap 204*b*. Rod 161 may be terminated with a with a diametrically enlarged cylindrical disk 162 configured to engage push-pop cap 204*b*. Actuator 160 is operable to disengage and unlock the push-pop cap from retention slots 202*c* (i.e. retention protrusions 205*a*) so that the cap can be moved upwards in sample tube 202 for reasons associated with the sample tube filling operation, as further described herein.

Figure 26:
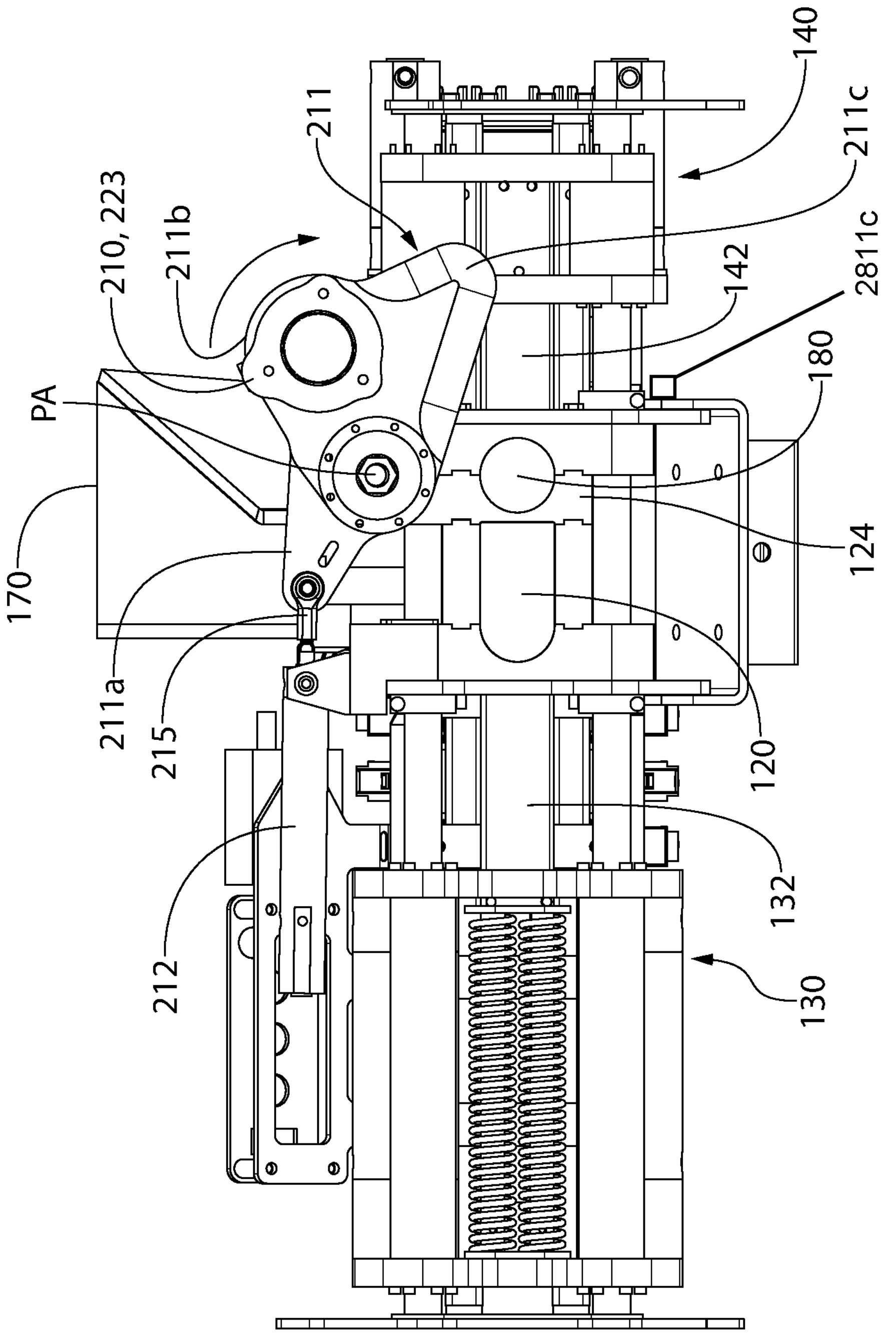
FIG. 26 is bottom view of the apparatus showing the carousel in the outward open position.
Figure 27:
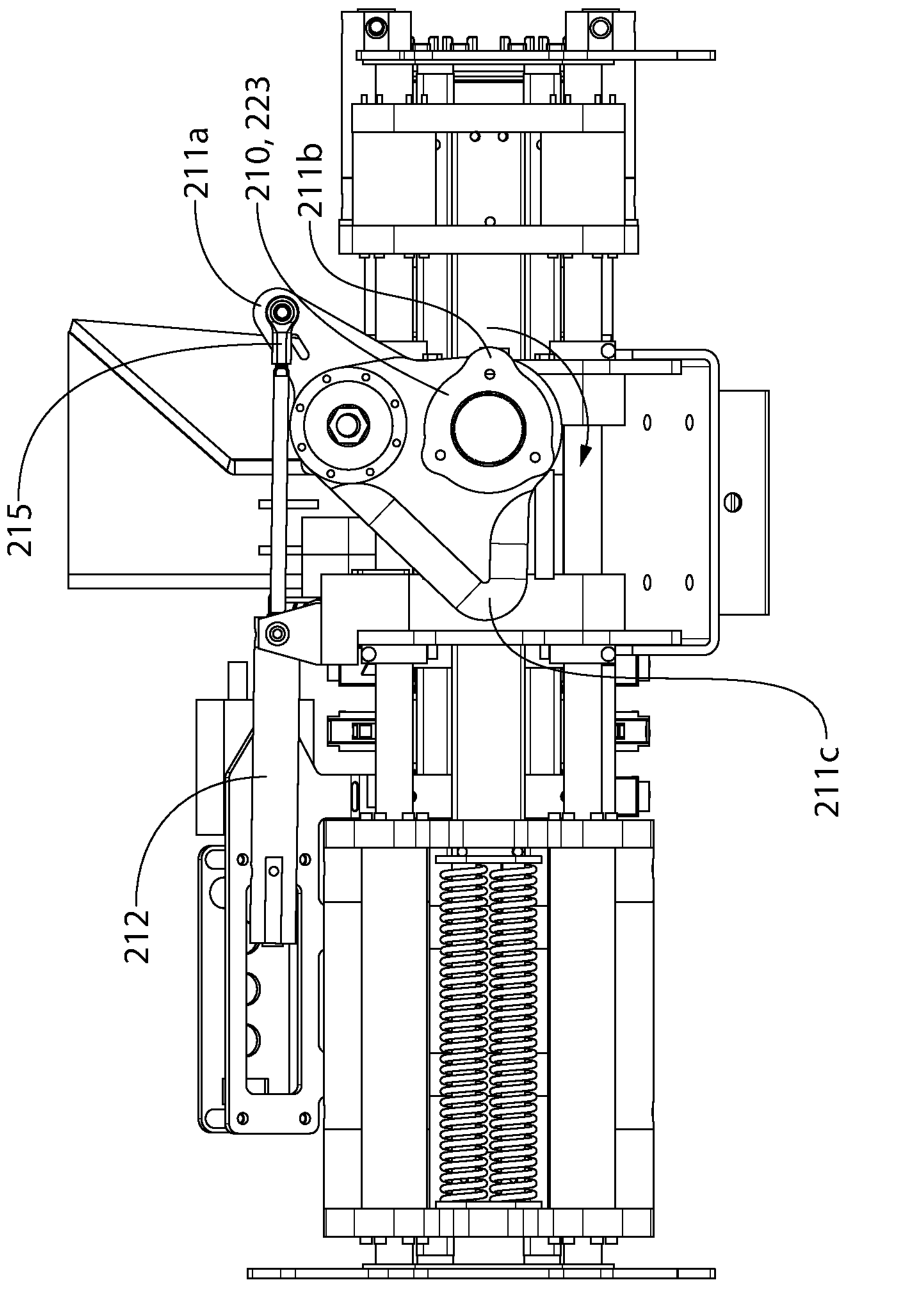
FIG. 27 is a bottom view of the apparatus showing the carousel in the inward closed position.

The actuator 212 coupled to cam arm 211*a* of base member 211 may be any suitable commercially available electric linear rod actuator, pneumatic actuator, or hydraulic actuator with retractable/extendible operating rod 215 coupled to the cam arm (see, e.g., FIG. 26). Actuator 212 is operable to rotate base member 211 about pivot axis PA to move the carousel between: (1) an inward closed position for tube filling in which sample tube 202 is positioned directly beneath and adjacent to the bottom end of sample chamber 180 and base member closure arm 211*c* is positioned directly beneath and adjacent to the bottom end of bulk material chamber 120 to close that chamber (see, e.g., FIG. 27); and (2) an outward open position in which sample tube 202 is not positioned beneath sample chamber 180 and base member closure arm 211*c* is not positioned beneath and adjacent to the bottom end of bulk material chamber 120 which is then downwardly open (see, e.g., FIG. 26). In the outward position, sample tubes 202 may be exchanged between tube filling cycles to remove filled tubes and mount new empty tubes.

A method or process for packaging an agricultural sample will now be described. In one embodiment, the sample may be a soil sample which will be used for convenience and without limitation as a basis for describing the operation of agricultural sample packaging system 100 disclosed herein. FIG. 1 is a high-level process flow chart providing a summary overview of the packaging process. FIGS. 22-40 are sequential images showing one non-limiting embodiment the sample packaging operation and positional changes of the agricultural sample packaging apparatus 110 described herein. The sample material used in the process below may be soil for convenience of discussion and not limitation.

Figure 22:
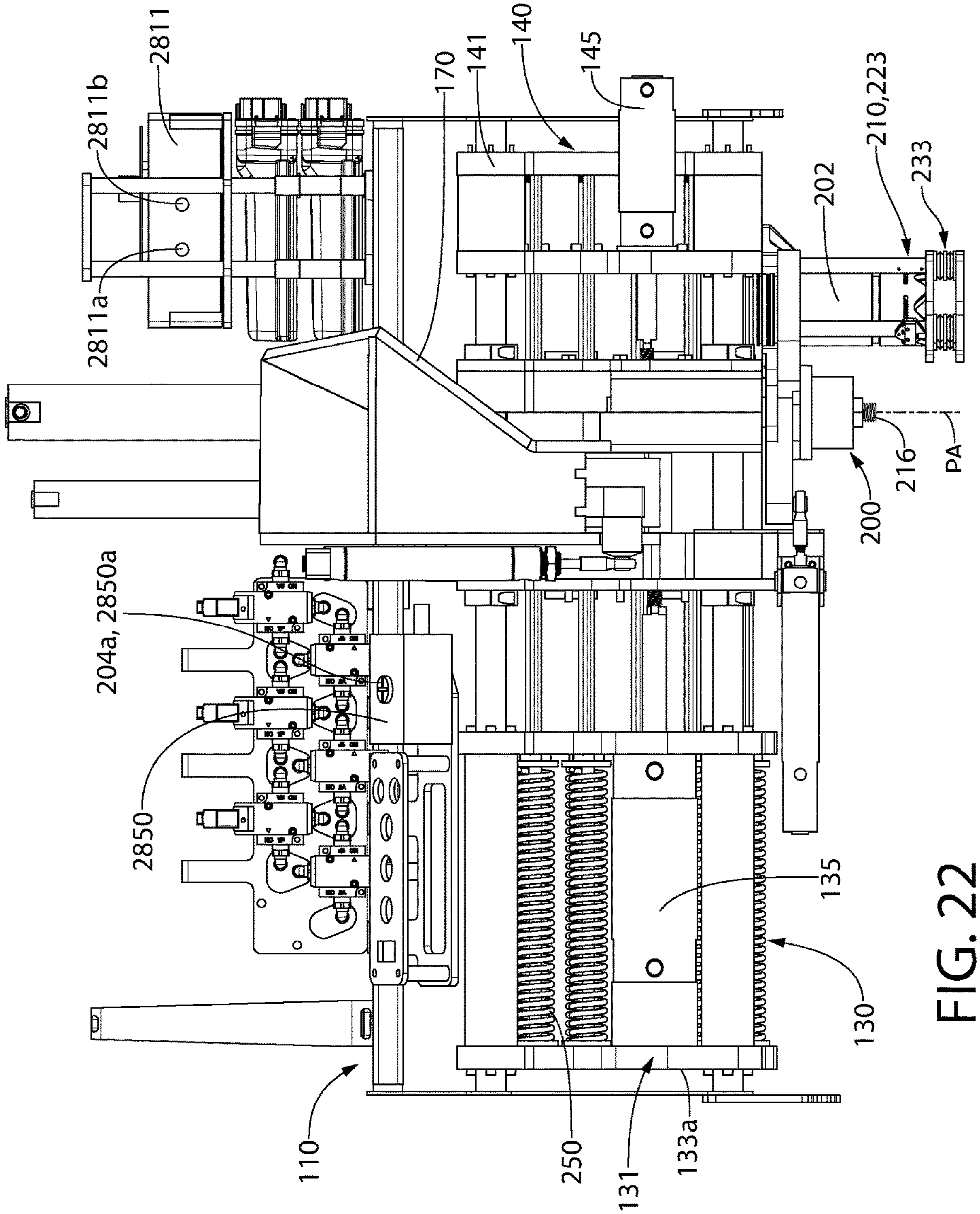
FIG. 22 is a front view of the sample packaging apparatus showing one operating position of the mechanism with sample funnel attached and the rotatable carousel with sample container supported thereby in the outward open position.

The method begins with the carousel 200 in the outward open position (see, e.g., FIG. 22). If the carousel is not outward and ready to accept the new empty sample tube 202, a carousel may be rotated outwards by actuating an actuator 2811*b* such as a button, toggle, or other type switch (FIG. 22) in some embodiment which is operably coupled to packaging machine controller 2811 (see, e.g., FIGS. 25-27). This may arbitrarily be referred to as the "Load Tube" switch or by another name. In other embodiments, the step may be actuated via a personal electronic device 2851 operably coupled to controller 2811 which initiates outward rotation of the carousel (see, e.g., FIG. 2). In either control scenario, rotating the carousel outward enables the operator to manually insert sample tube 202 into the container holder 210 or 223 of the carousel 200.

Figure 23:
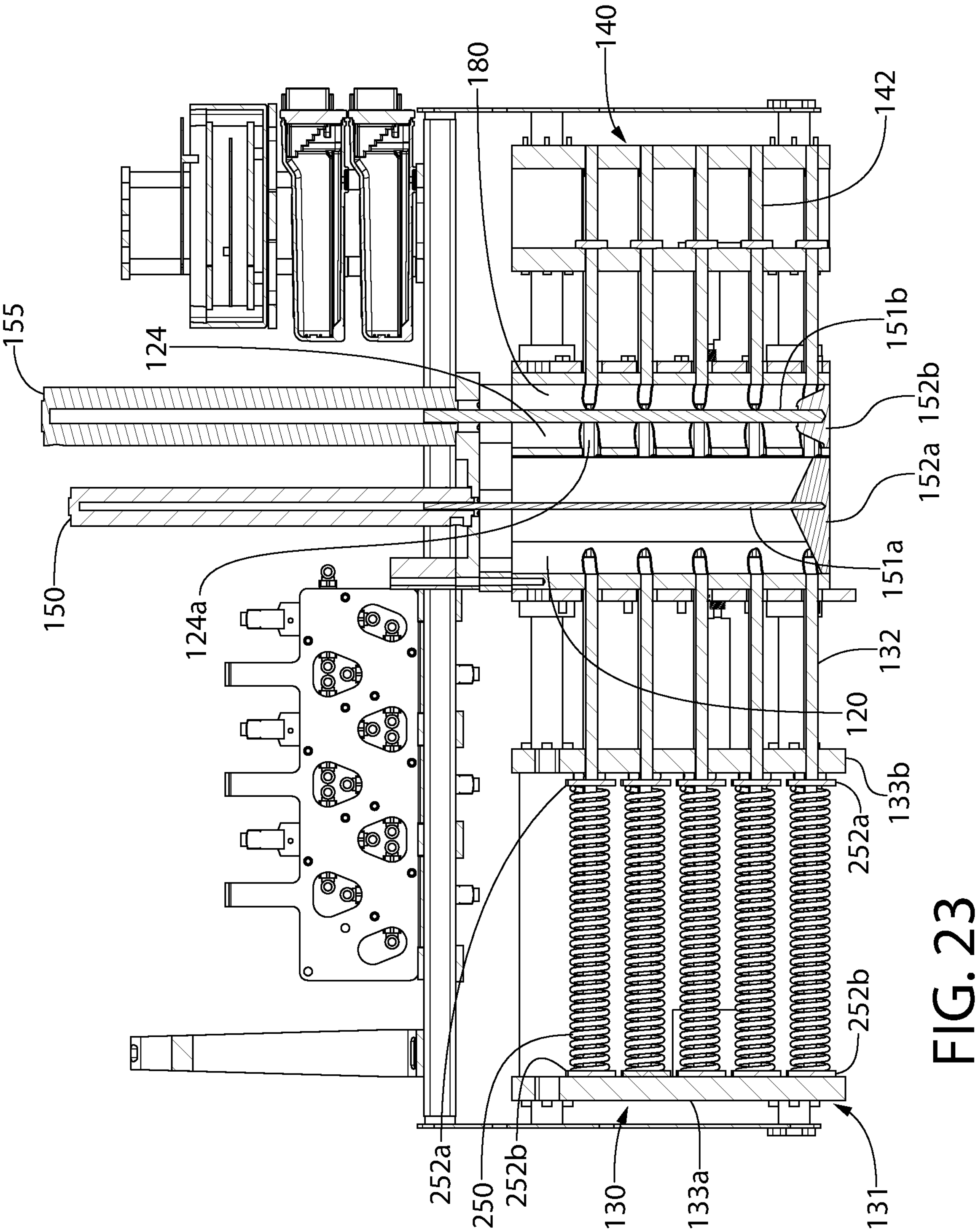
FIG. 23 is a front cross-sectional view thereof.

At the start of the packaging operation, the piston-plungers 150 and 155 are preferably in their downward extended/projected position shown in FIG. 23 from either the previous container packaging operation or in preparation to start the first packaging operation.

An empty sample container 201 such as sample tube 202 is first vertically inserted into and placed in the container holder 210 of the carousel A castellated and rotationally interlocked interface is formed between the bottom end 203*b* of the tube and support disk 213 of the holder 210, as previously described herein. The top end cap 204*a* of sample tube 202 containing the RFID tag 2850*a* is placed on RFID reader 2852. Packaging machine controller 2811 and/or main system controller 2820 automatically reads the tag and begins tracking the sample including all relevant data such as geolocation via GPS sensor 2854, time of day, etc. The RFID tag could alternatively be contained within the plunger cap 204*b* and read automatically when the sample tube is loaded into the carousel 200. Additionally, if the RFID tag is within any portion of the tube or plunger cap that is loaded into container holder 210, the reader may be attached to container holder 210, enabling the capability to read the tube when it is loaded and not requiring a separate station for RFID reading.

At this point in the method/process, the funnel door 171 is in the closed position (see, e.g., FIG. 24). This prevents the soil sample material if loaded into the funnel 170 from entering and falling out of the still open bottom of the bulk material chamber 120 if loaded into the funnel before the sample tube 202 is rotated beneath chamber 120.

Carousel 200 is then rotated to the inward closed position via operation of carousel actuator 212. In some embodiments, this step may be initiated by actuating an actuator 2811*a* such as a button, toggle, or other type switch (FIG. 22) operably coupled to packaging machine controller 2811 (see, e.g., FIGS. 25-27). This may arbitrarily be referred to as the "Fill Tube" actuator or by another name. In other embodiments, the step may be actuated via a personal electronic device 2851 operably coupled to controller 2811 which initiates rotation of the carousel (see, e.g., FIG. 2). In either control scenario, rotating the carousel inwards positions sample tube 202 under sample collection chamber 180. The base member 211 (i.e. closure arm 211*c*) closes the bottom end of previously open bulk material chamber 120.

With the piston-plungers 150, 155 still in their downward position, it bears noting that the closure arm 211*c* of the carousel 200 will scrape any residue away from the bottom faces of the plunger disks 152*a*, 152*b* as the closure arm rotates inwards which may remain from the last container packaging operation.

The soil sample material may be added to funnel 170 after rotating the carousel inwards or at any point before that so long as the funnel door 171 remains closed up to this point in the process.

Next, the push-pop cap 204*b* is unlocked/unclipped from the sample tube 202 by actuating end cap actuator 160 for those embodiments including the actuator. The actuator disengages the retention protrusions 205 of push-pop cap 204*b* from the retention slots 202*c* in tube 202 and slideably pushes the cap vertically upwards inside the tube. Cap 204*b* is therefore no longer locked near the bottom end 203*b* of sample tube 202, but at some preselected position between the ends of the tubes. The protrusions 205 have a radially outwards directed spring force sufficient to positively engage the inside surface of cylindrical sample tube wall 202*a* to retain the position of the push-pop cap 204*b*.

Alternatively, if the alternative container holder 223 embodiment without actuator 160 is used as further described below and shown in FIG. 22 et al., the push-pop cap remains at its lower locked position in sample tube 202.

Figure 28:
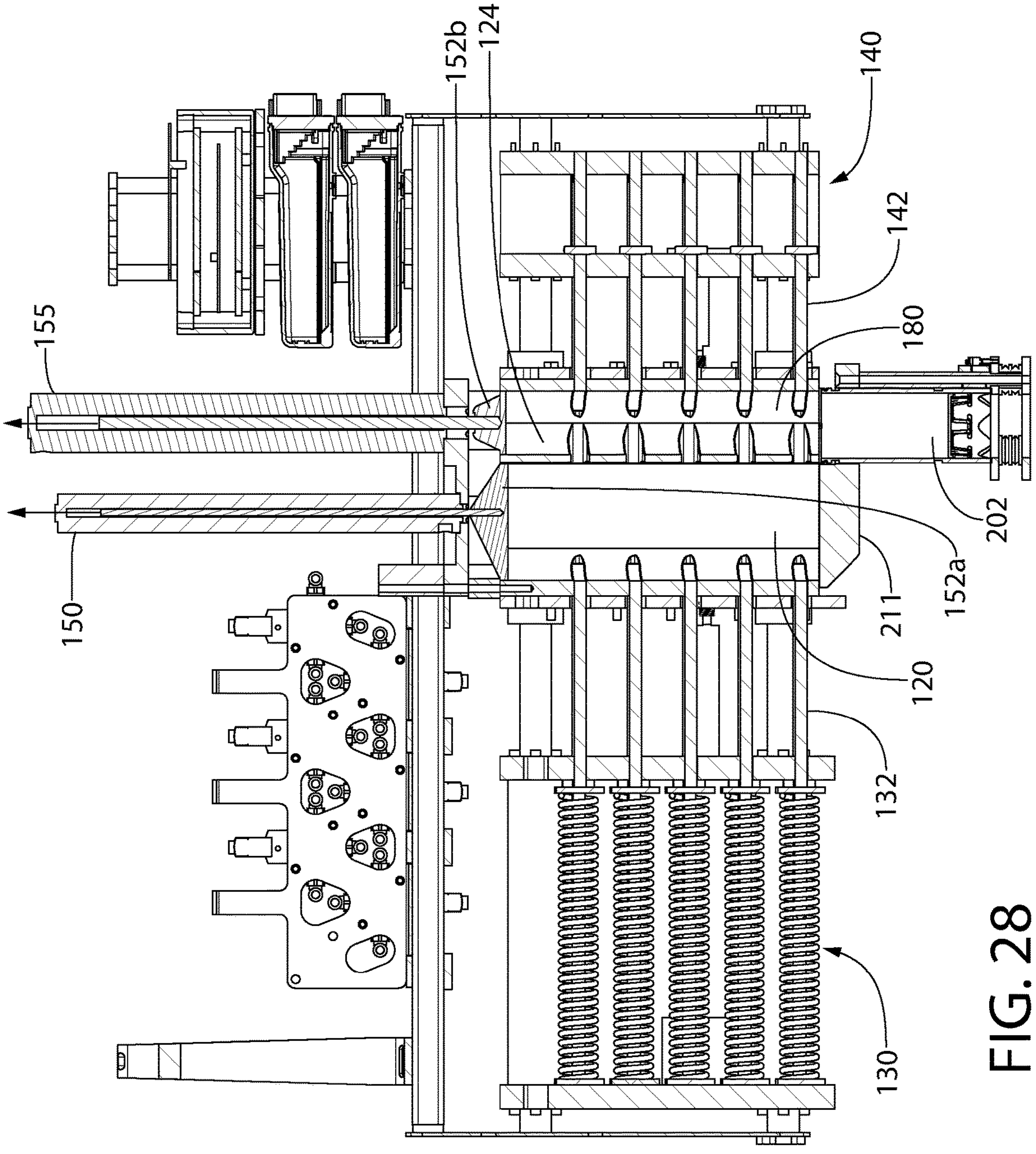
FIG. 28 is a front cross-sectional view of the apparatus showing the sample and cleaning blades of the apparatus in their retracted positions.

As shown in FIG. 28, the piston-plungers 150, 155 are retracted from the bulk material chamber 120 and sample collection chamber 180 (see, e.g., FIG. 28) if not previously retracted.

Figure 29:
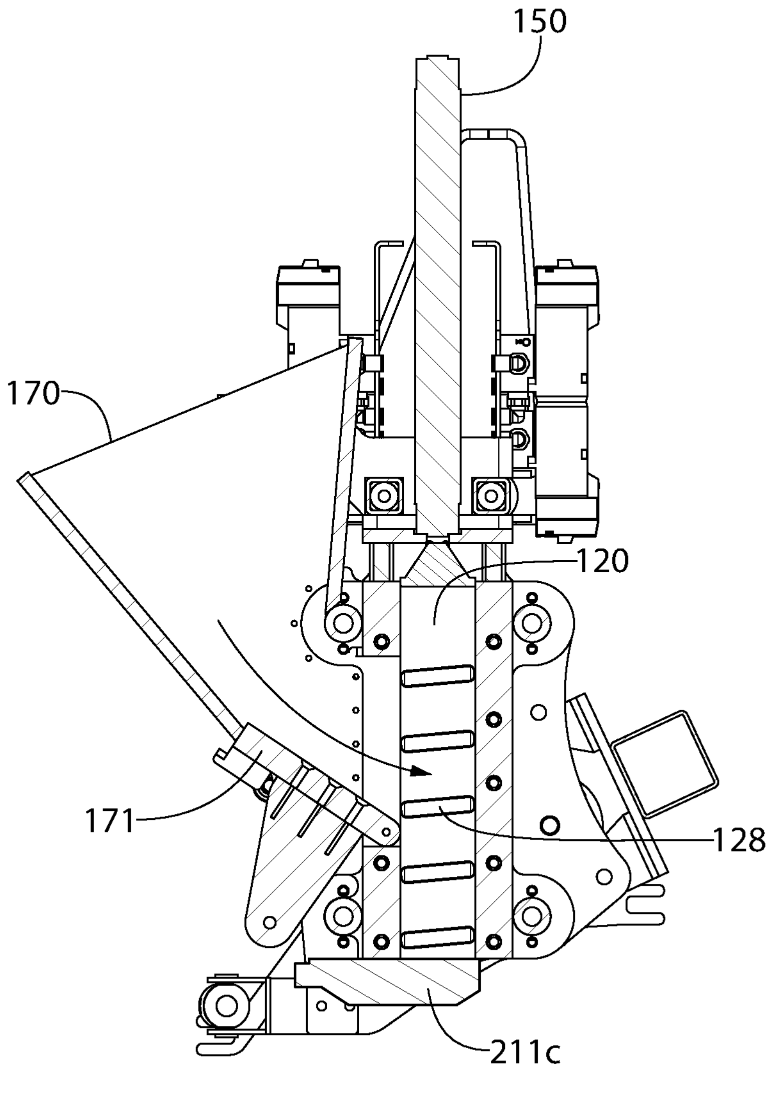
FIG. 29 is a side cross-sectional view of the apparatus showing the funnel door in the open position to admit sample material into the bulk material chamber as indicated by the directional arrow.
Figure 30:
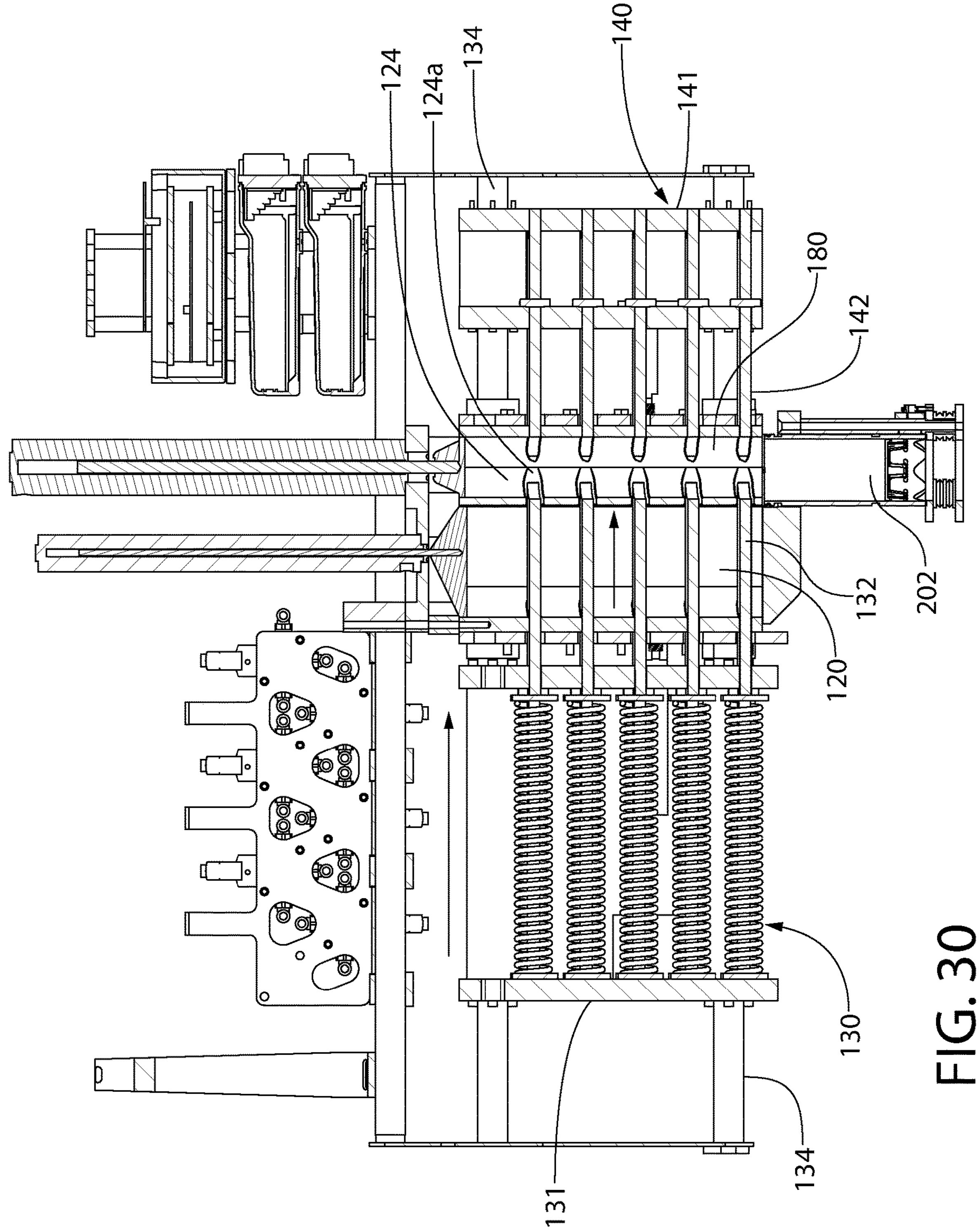
FIG. 30 is a front cross-sectional view of the apparatus showing the sample blades in their projected positions inserted through the bulk material chamber and die block.

Once the carousel is set up as described above and piston-plungers 150, 155 are retracted, the soil sample extraction process is ready to begin. The funnel door 171 is opened via operation of actuator 172. The bulk soil sample material is transferred to and enters the bulk material chamber 120 (FIG. 29). Door 171 may then be shut, which compacts any slight overfill of the chamber and prevents any remaining soil in the funnel from working its way into the chamber.

The method continues with activation of the sample blade mechanism 130. Actuator 135 slideably moves the sample blade chassis 131 along guide rods 134 and sample blades 132 are inserted through bulk material chamber 120 and die block 124. The blades 132 move from the initial retracted position to the projected position previously described herein (e.g., towards the right in FIG. 30—see directional arrows). The sample blades 132 each extrude or force a portion of soil from the bulk material sample through a respective die slot 124*a* in die block 124. The extruded/extracted soil, which comprises multiple plugs or blanks of soil are deposited in sample collection chamber 180 by the advancing blades 132). The extracted soil plugs fall downward into open sample tube 202 waiting below chamber 180.

Figure 31:
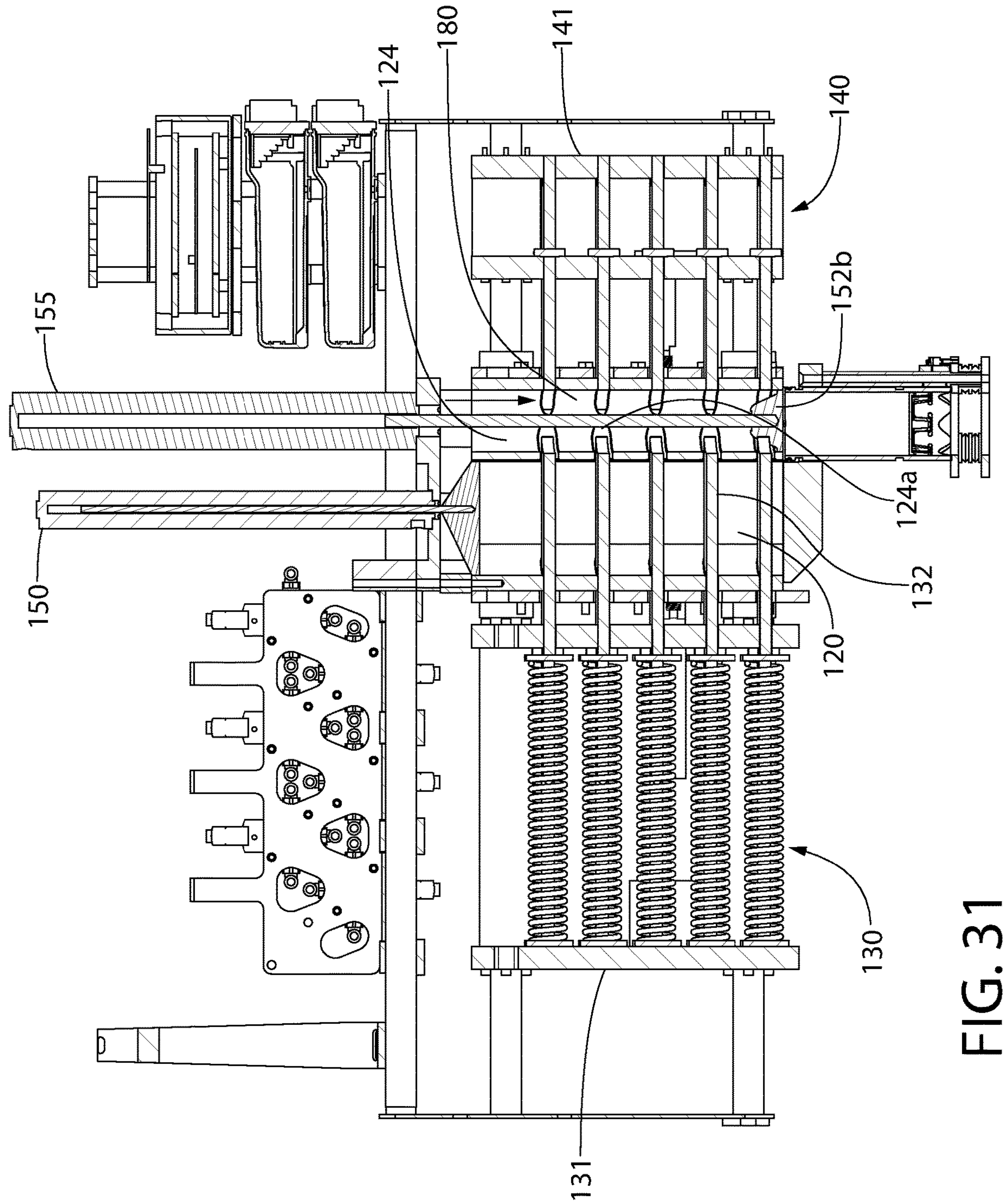
FIG. 31 is a front cross-sectional view thereof showing the sample transfer piston-plunger in its downward extended/projected position.

Sample transfer piston-plunger 155 may then be actuated to ensure all of the soil sample material in collection chamber 180 is positively pushed downwards into the sample tube (see, e.g., FIG. 31). Preferably, this step is conducted while sample blades 132 remain in the die block 124 within die slots 124*a* to ensure that the soil in chamber 180 is not pushed laterally backwards into the die slots 124*a* of die block 124 by the piston-plunger. Piston-plunger 155 may be extended all the into the sample tube 202 to tightly pack the soil in the tube. Notably, the piston-plunger compacts the soil in sample tube 202 while forcing and displacing the push-pop cap 204*b* back downwards incrementally by a distance. This advantageously ensures that soil sample in the tube is a tightly packed sample.

Piston-plunger 155 may then be withdrawn from the sample tube 202 and chamber 180, and returns vertically upwards back to its initial retracted position.

Figure 32:
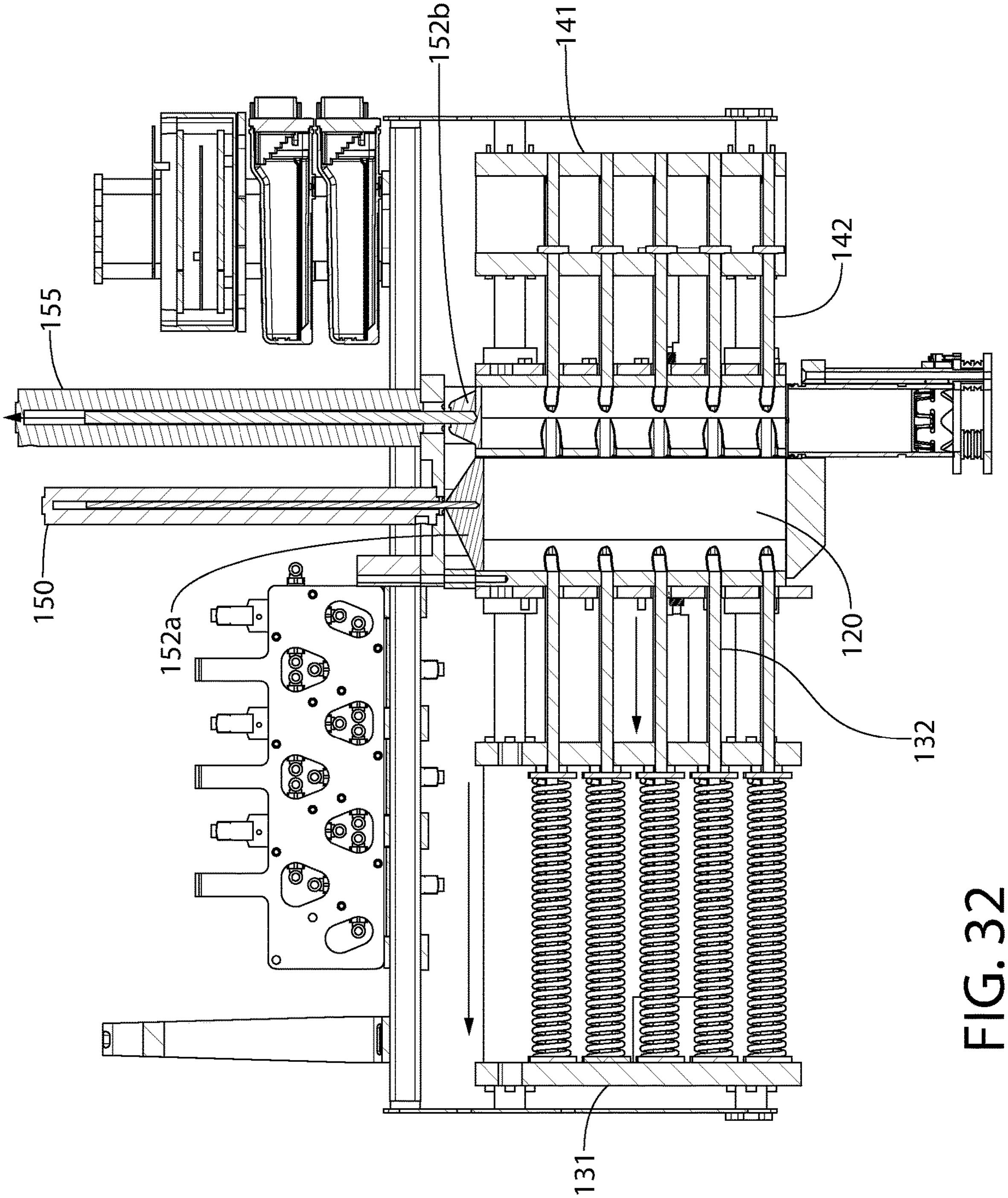
FIG. 32 is a front cross-sectional view thereof showing the sample transfer piston-plunger returned to its upward retracted position.
Figure 33:
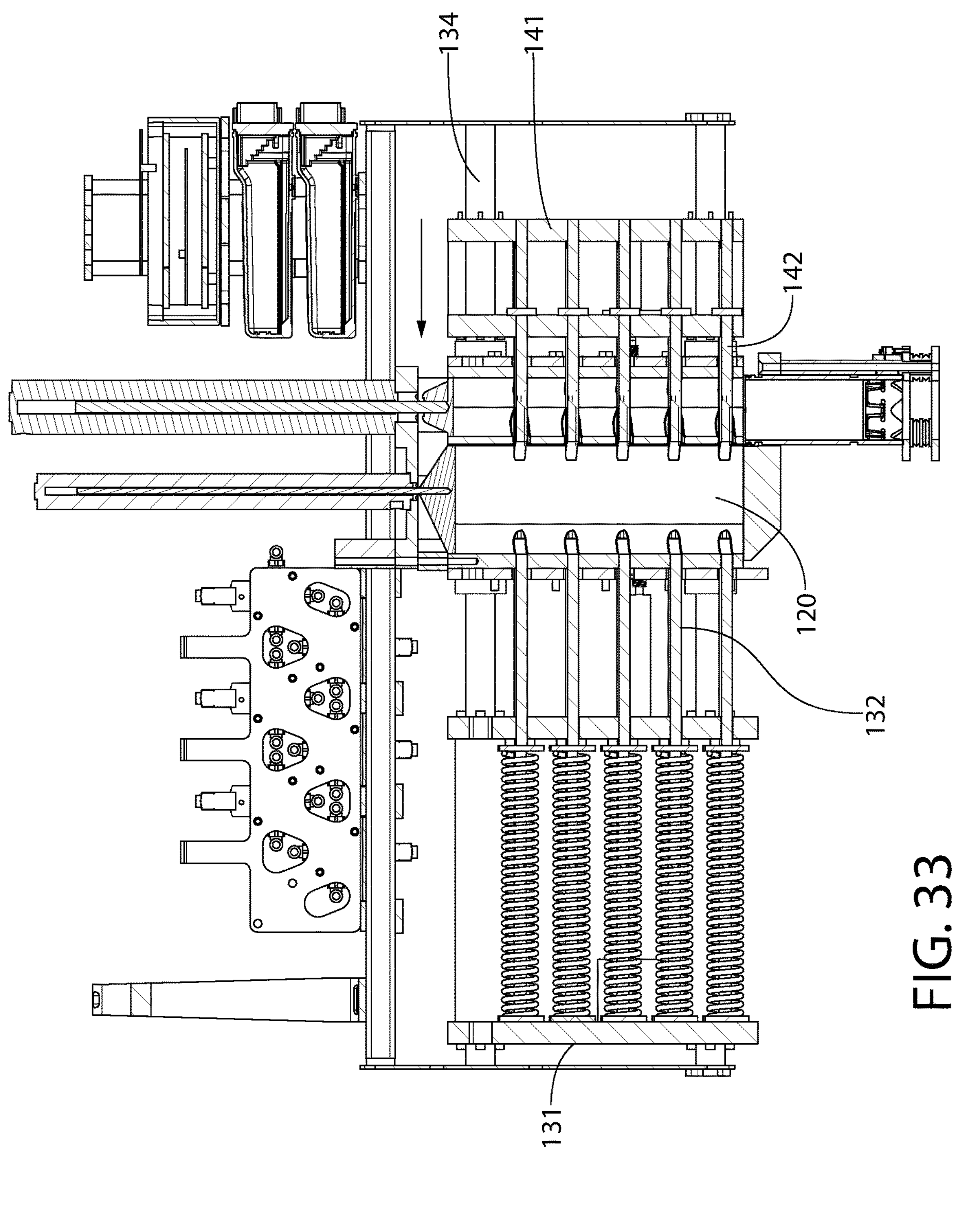
FIG. 33 is front cross-sectional view thereof showing the cleaning blades in their projected position inserted through the sample collection chamber and die block.

The method continues with withdrawing the sample blades 132 from the die block 124 and bulk material chamber 120 by returning the chassis 131 of the sample blade mechanism 130 to the retracted position (e.g., towards the left in FIG. 32).

The method continues with actuating the cleaning blade mechanism 140. Actuator 145 moves the cleaning blade chassis 141 and cleaning blades 142 from the initial retracted position to the projected position previously described herein (e.g., towards the left in FIG. 33). Cleaning blades 142 are inserted through sample collection chamber 180 and die slots 124*a* in the die block. The cleaning blades 142 each push any residual soil residue or particularly hard non-soil debris (e.g. stones, etc.) which may have been trapped in the die slots 124*a* backwards and into the bulk material sample chamber 120.

Figure 34:
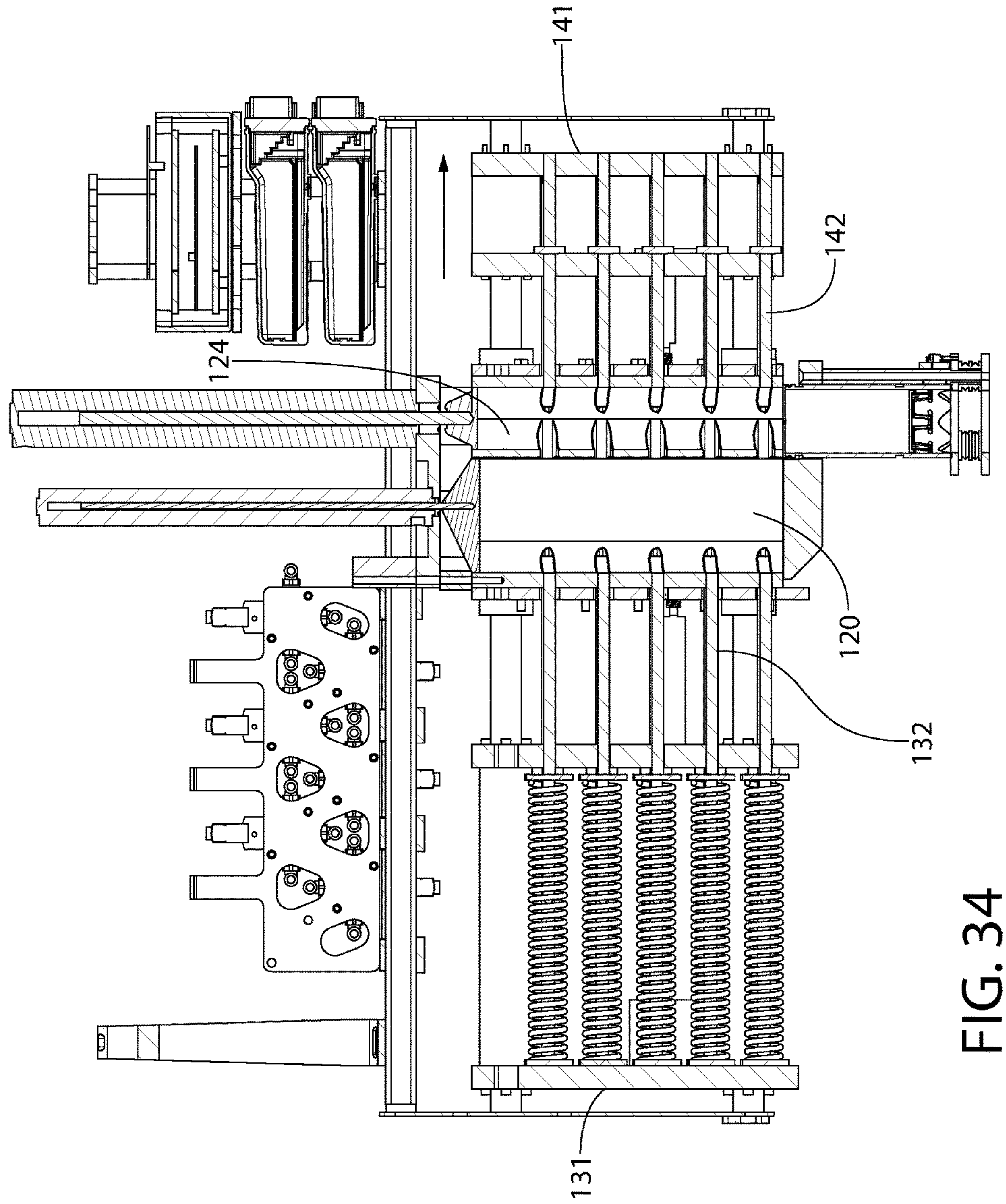
FIG. 34 is a front cross-sectional view thereof showing the cleaning blades returned to their retracted positions.

The cleaning blades 142 are then retracted from the die block 124 and soil collection chamber 180 by reversing the above operation (see, e.g., FIG. 34).

Figure 35:
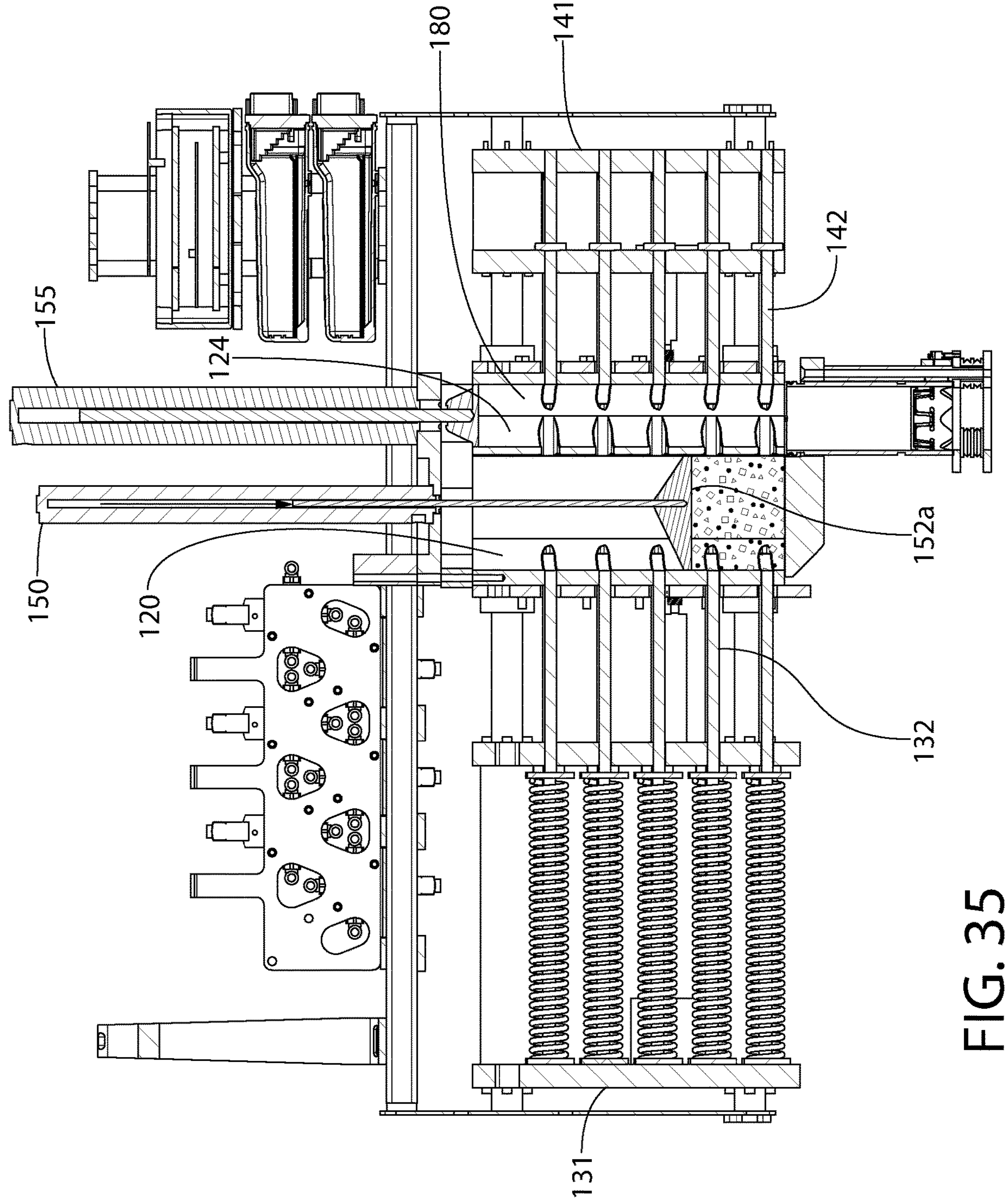
FIG. 35 is a front cross-sectional view thereof showing the compaction transfer piston-plunger in its downward extended/projected position.

Next, compaction piston-plunger 150 is actuated to repack the soil in bulk material chamber 120 (see, e.g., FIG. 35). The piston-plunger 150 moves vertically downwards in chamber 120 to compact the remaining soil in the chamber. This is particularly beneficial if moist sticky and dense soil such as clay is being processed. It is possible that the sample blades 132 may leave voids in the self-supporting soil material remaining in chamber 120 when the blades are initially withdrawn from the soil in the chamber when the sample material plugs were first extruded. If so, the next extraction cycle may fail to displace and collect any appreciable amount of soil for the sample due to the presences of the voids. To remedy this possibility and maintain a quick pace of extracting a full soil sample, the piston-plunger 150 advantageously will collapse the soil and remove any such voids.

Figure 36:
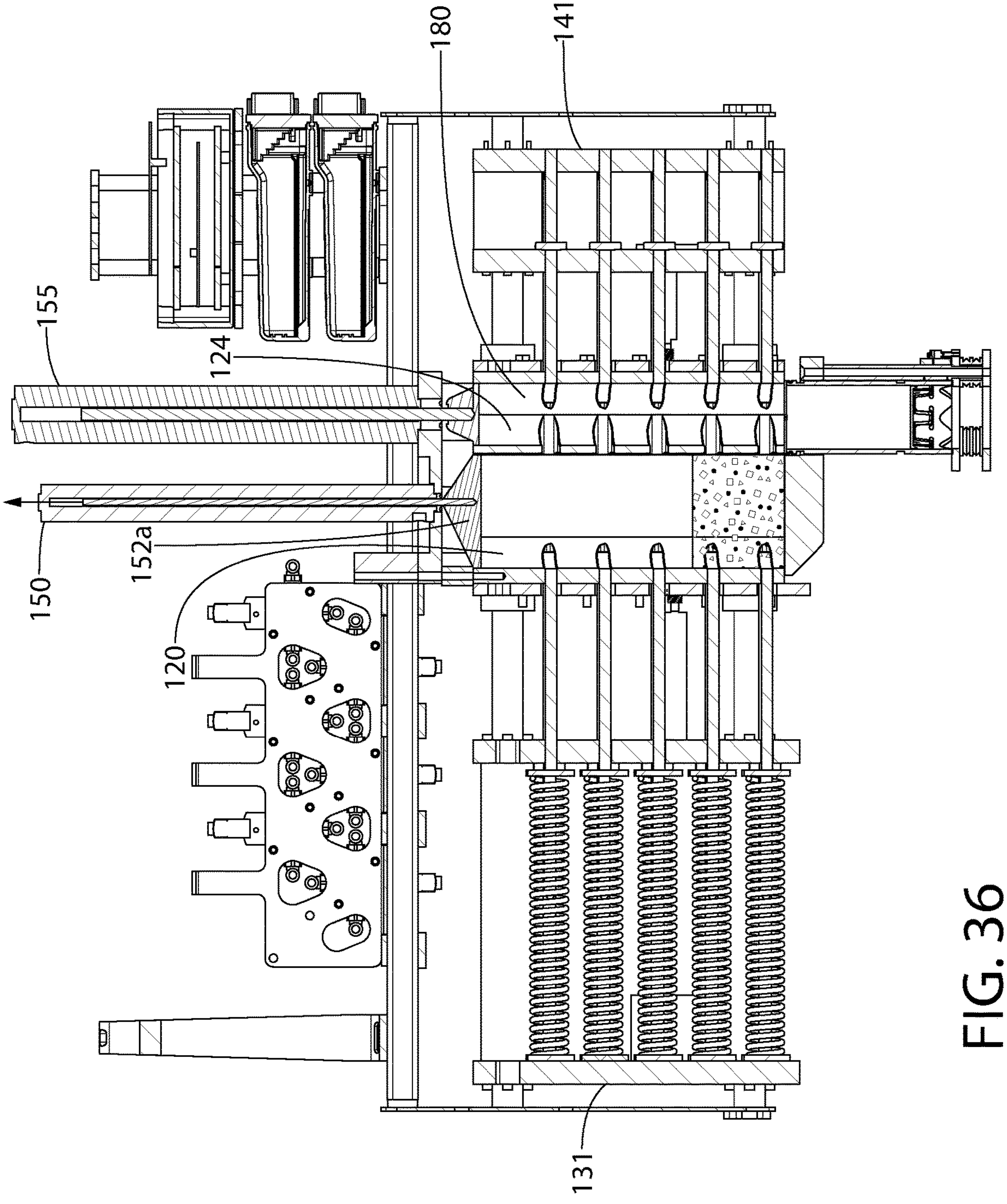
FIG. 36 is a front cross-sectional view thereof showing the compaction piston-plunger returned to its upward retracted position.

Next, the compaction piston-plunger 150 is retracted from bulk material chamber 120 (see, e.g., FIG. 36).

It bears noting that a single soil sample plug or blank extraction cycle as described above may not be sufficient to sufficiently fill the sample tube 202 with enough soil for further processing and eventual chemical analysis. Accordingly, the entire cycle may be repeated multiple times to extract a sufficient amount of the soil sample material for chemical testing in a related process.

It should also be noted that in sample packaging apparatus 110 embodiments including the cap actuator 160, the push-pop cap 204*b* gradually advances farther downwards inside sample tube 202 as the tube is gradually filled and packed down by piston-plunger 155 as previously described herein. The retention protrusions 205 of cap 204*b* eventually re-engage and snap back into the retention slots 202*c* of the sample tube. This represents the lowermost position of the cap 204*b* in the tube and maximum volumetric capacity of the tube.

Figure 38:
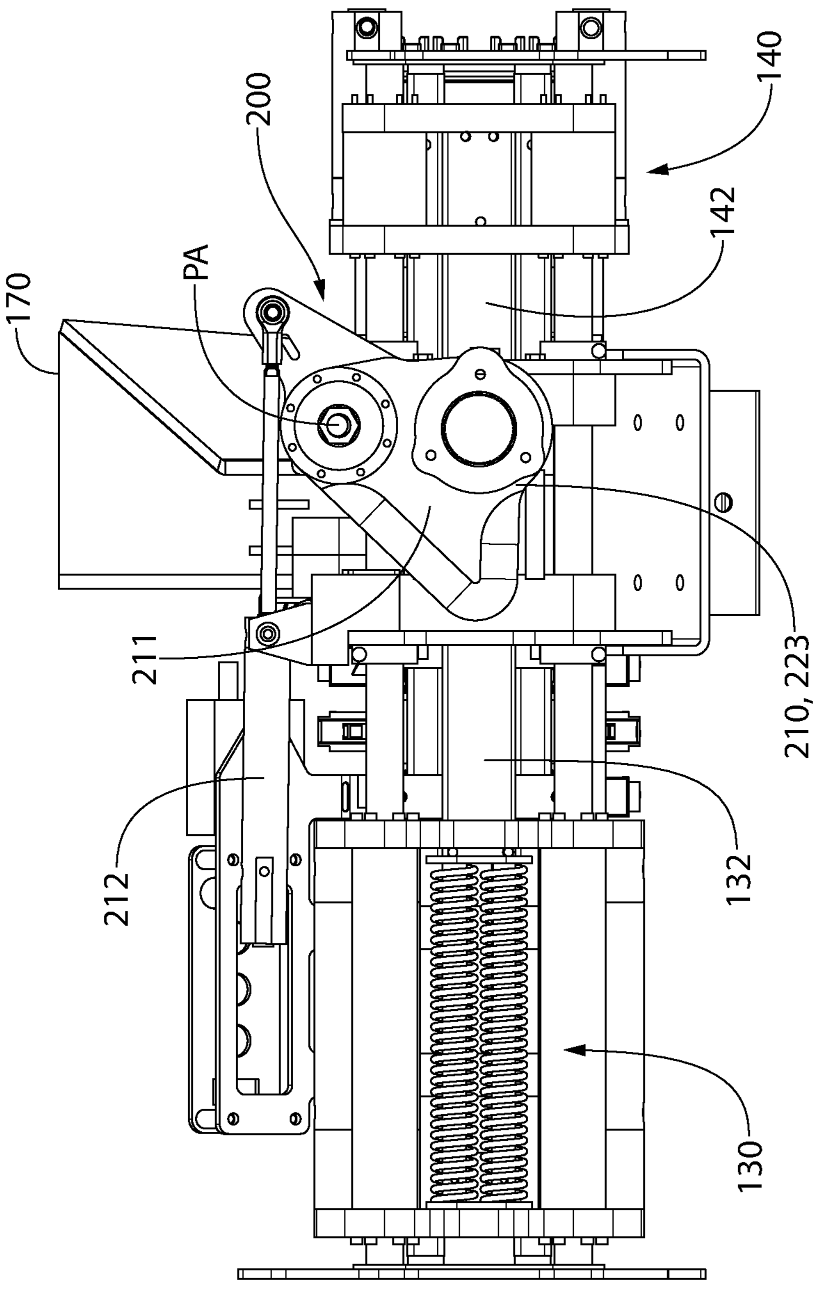
FIG. 38 is a bottom view of the apparatus showing the carousel and sample container rotated to the inward closed position ready for filling with the agricultural sample material.
Figure 39:
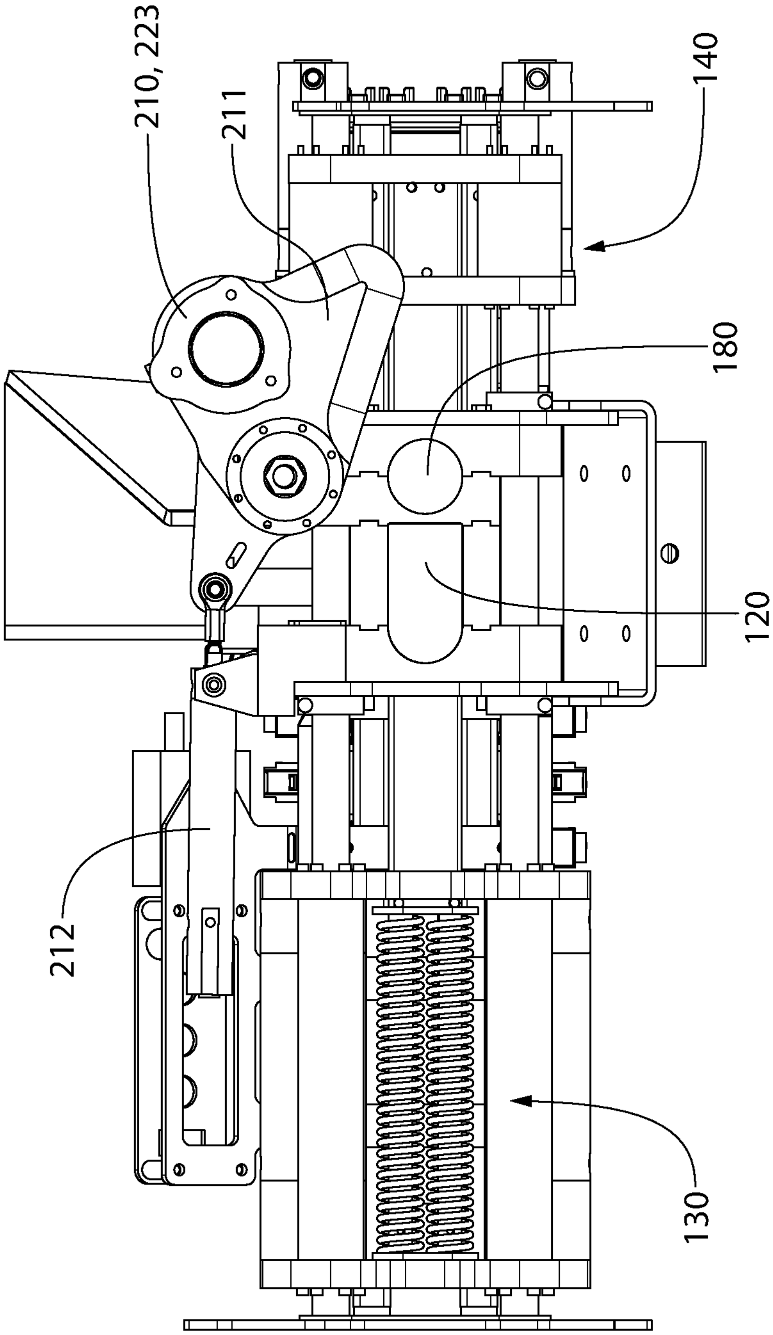
FIG. 39 is bottom view of thereof showing the carousel in the outward open position to enable removal of a filled sample container from the apparatus.

Once the sample tube 202 is full, the carousel 200 is rotated back to the outwards open position (see, e.g., FIGS. 38-29). The carousel is configured such that it screeds the top of the tube to remove any soil mounded above the top rim of the tube so that the top end cap 204*a* can be installed without having to manually level off any upwardly protruding mound of soil. Any mound of soil will be screeded or scraped off by the bottom surface of the chamber block 123 portion adjacent to sample collection chamber 180 as the baseplate 211 of the carousel 200 rotates to its open outward position. The stationary end cap 204*a* may then be manually removed from RFID reader 2850 with RFID tag 2850*a* and coupled to the open top end 203*a* of the tube to seal the sample. If the tag 2850*a* is not located on the stationary top end cap 204*a*, that cap need not be placed on an RFID reader and may be recovered from wherever stored. In either case, the packed and sealed sample tube 202 may then be removed from packaging apparatus 110 for further processing and eventual chemical analysis.

Figure 40:
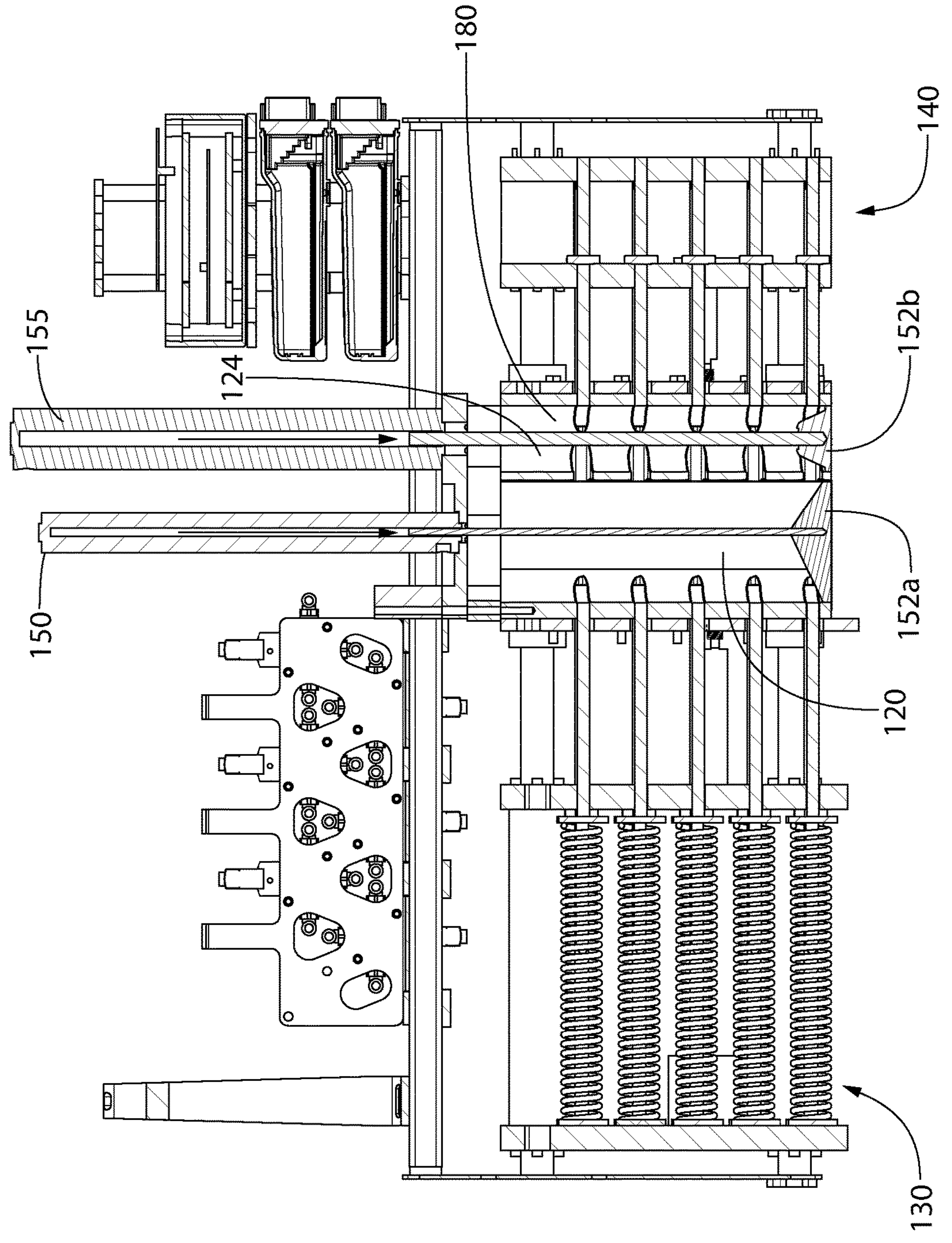
FIG. 40 is a front cross-sectional view of the apparatus showing the sample transfer piston-plunger and compaction plunger in their downward projected positions.
Figure 41:
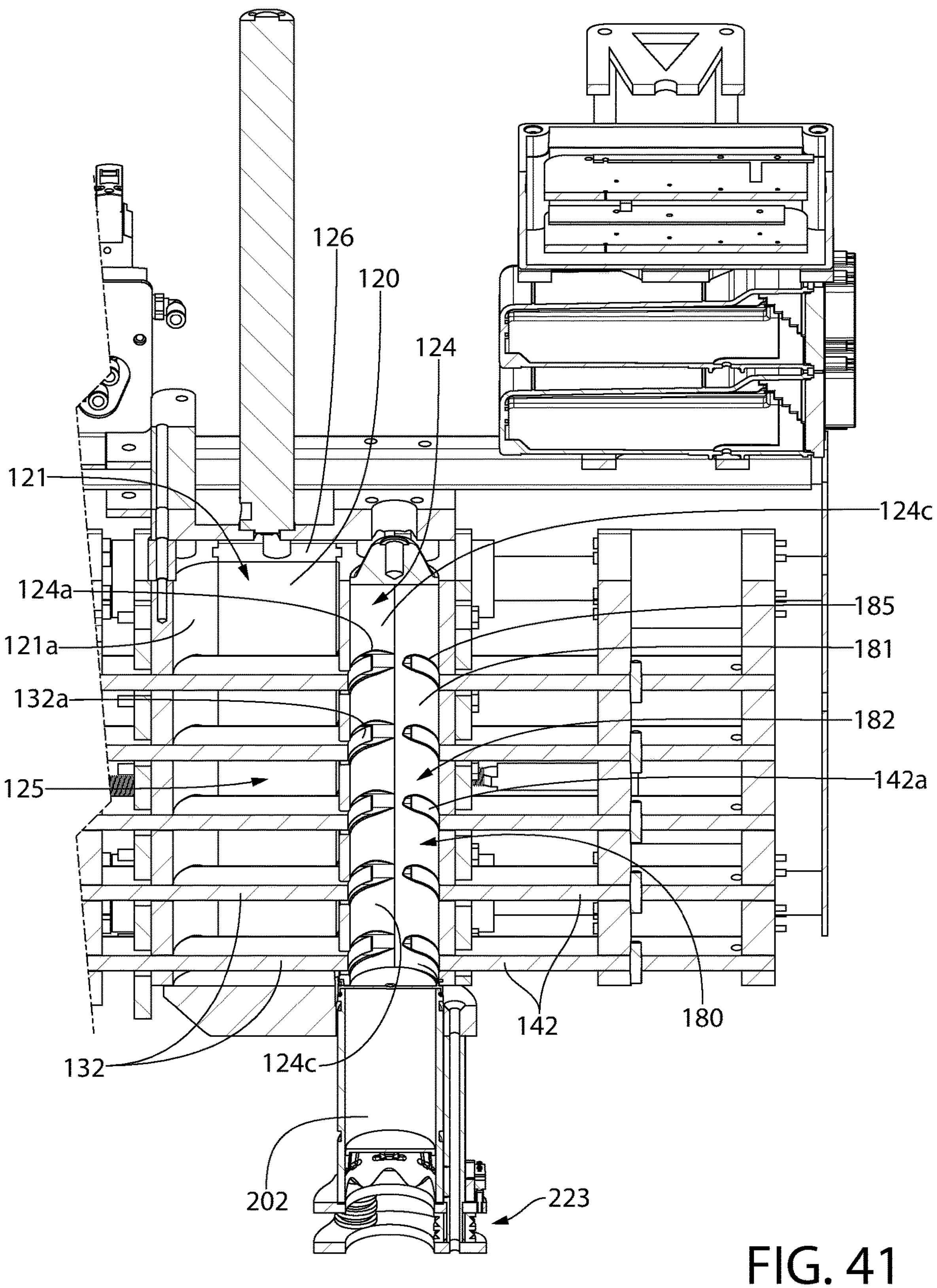
FIG. 41 is an enlarged partial front cross-sectional view of the chambers and die block of the apparatus.

With the carousel still in the outward open position, sample transfer piston-plunger 155 and compaction piston-plunger 150 may be run back through their respective soil collection and bulk material chambers 180, 120 to remove any residual soil in preparation for the next round of extracting the soil samples (see, e.g., FIG. 40).

The sample transfer piston-plunger 155 and compaction piston-plunger 150 may remain in this downward position with disk 152*a*, 152*b* exposed at the bottom ends of the bulk material chamber 120 and sample collection chamber 180. After the sample tube 202 has been loaded into the carousel 200 for the next set of soil sample extractions, rotating the carousel to inward closed position will wipe the exposed faces of the piston-plungers 150, 155 clean as the closure arm 211*c* passes beneath both piston-plungers. The piston-plungers can each be returned to their upward position before soil is added to the bulk material chamber 120 for the sample plug/blank extractions.

It bears noting that compaction piston-plunger 150 doubles as a scraper to clean the ends of the sample blades 132 when in their retracted position each time the plunger moves downwards and upwards in the bulk material chamber 120. In a similar manner, the sample transfer piston-plunger doubles 155 which travels upwards/downwards in sample collection chamber 180 acts as a scraper to clean the ends of the sample blades 132 when in the projected position extending through the die block 124 and the ends of the cleaning blades 142 with each downward/upward movement of the plunger. This is possible because, as previously described herein, the terminal ends of the sample blades 132 form part of the exposed inner walls of the chamber 120 when retracted and part of the inner walls of chamber 180 when projected. In a similar vane, the terminal ends of cleaning blades 142 form part of the inner walls of chamber 180.

Figure 37:
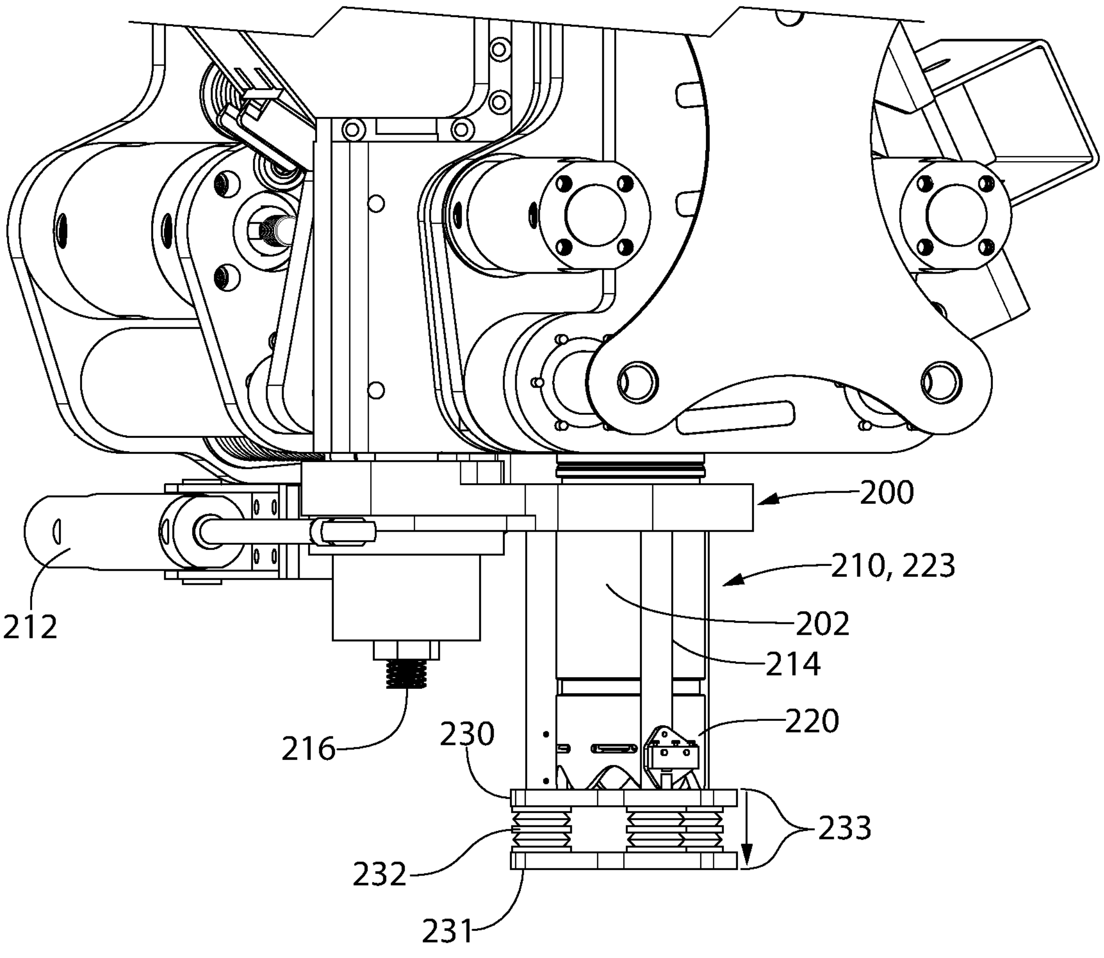
FIG. 37 is partial front perspective view of the carousel showing a collapsible embodiment of the container holder with container sensor.

FIGS. 22 and 37 depict an alternative embodiment of a sample container holder assembly which omits the end cap actuator 160. In this embodiment, the present container holder 223 comprises a collapsible dual support plate assembly 233 which is supported and suspended by spacer rods 214 beneath the base member 211 of carousel 200. The dual plate assembly comprises a lower fixed plate 231 rigidly coupled to the bottom ends of spacers rods 214 and upper floating plate 230 vertically slideable up and down on the spacer rods relative to fixed plate 231. Fixed plate 231 thus remains stationary relative to the base member 211 of carousel 200 and spacer rods 214. The fixed and floating plates 231, 230 are spaced apart by plurality of springs 232 coupled between the plates. The sample tube 202 is seated on the upper floating plate when the tube is positioned on the packaging apparatus 110. The support plate assembly 233 is movable between an expanded condition in which the floating and fixed plates 230, 231 are spaced apart by springs 232 by a maximum extent and distal to each other, and a collapsed condition in which the plates 230, 231 are proximate to each other or closest when the springs are compressed by piston-plunger 155 as further described herein.

In operation, the general steps in foregoing description of the method for packaging an agricultural sample remain the same and will not be repeated for sake of brevity. The differences in the method when using the present container holder 223 is as follows. First, the push-pop cap 204*b* is not unlocked and moved upward in sample tube 202 before adding soil to the tube since the cap actuator 160 is omitted in the present embodiment. Accordingly, cap 204*b* remains in its lowermost position proximate to bottom end 203*b* of tube and locked to the retention slots 202*c* of the tube. In some embodiments, the cap 204*b* could be replaced by a fixed immovable cap coupled to the bottom end of the tube similar to cap 204*a* coupled to the top tube end 203*a*.

A second difference in the method for packaging the agricultural sample is that the movable dual plate assembly 233 is activated and collapsed when the sample tube 202 is completely filled to capacity. The dual plate assembly 233 begins in the expanded condition when the sample tube is loaded onto the present container holder 223. After several tube fill cycles previously described herein, the tube will become full as the sample transfer piston-plunger 150 tamps and packs the soil into the tube. Once the maximum volume has been reached, the last tamping action will push the soil in the tube 202 and tube itself downwards together. This in turn moves the upper floating plate 230 downwards compressing the springs 232 counter to their upward biasing action. Support plate assembly 233 is now in the collapsed condition.

A full sample tube sensor 220 fixedly mounted adjacent to the bottom end of one of the spacer rods 214 is activated by the floating plate moving downward and configured detect movement of the floating plate, which is indicative of the tube being filled to capacity and ready for removal from the packaging apparatus 110. Sensor 220 sends a signal to the local machine controller 2811 onboard apparatus 110 and/or main system controller 2820 indicating the same. It bears noting that floating plate 230 will only be displaced when the tube 202 is filled to capacity as described above.

Any suitable type commercially available presence or contact sensing sensor including micro limit switches of suitable type, Hall effect sensors, etc. may be used to detect the presence or movement of floating plate 230. In one embodiment, a plunger type micro limit switch may be used as shown which comprises a depressible spring-biased plunger 221 that contacts upper floating plate 230 which the dual plate assembly dual support plate 233 is in the expanded condition (see, e.g., FIG. 46). If a micro limit switch is used, electrical contacts in the switch may be either opened (in a normally closed circuit) or closed (in a normally open circuit). In other embodiments, suitable load or force sensing sensors may be used. In yet other embodiments, non-contact type proximity sensors including inductive proximity, capacitive proximity, and photoelectric sensors may be used. Accordingly, there are a number of sensor options and the invention is not limited by the type of sensor employed so long as an appropriate "full tube" signal is transmitted to the local machine and/or main system controllers 2811, 2820.

It should be noted that the sample transfer piston-plunger 155 which tamps the sample into sample tube 202 does not directly apply force directly to the tube. Piston-plunger 155 applies its force directly to the sample in tube, and then the sample transmits its received force to the tube. This indirect force transfer allows the sample to be compressed consistently by the piston-plunger within the tube before triggering a full tube condition via sensor 220.

In other embodiments, full sample tube sensor 220 may be a commercially-available "load" or "force" sensor operably coupled to packaging machine controller 2811. This may be accomplished using controls and feedback via packaging machine controller 2811 with a commercially available actuator or load/force cells in place of the springs 232 of in container holder 223. The load/force cell sensor would be disposed between the lower fixed plate 231 and upper floating plate 230 of the dual support plate assembly 233 which are in abutting contact with each other. Commercially-available thin film type sensors can be used for this application sandwiched between plates 231 and 230. When the actual load/force sensed during the sample tube 202 filling operation reaches a predetermined load/force setpoint preprogrammed into controller 2811, the controller determines the tube is filled to capacity by comparing the setpoint to the actual sensed load/force. The load/force sensing arrangement is clear to those skilled in the art based on the foregoing description without further undue elaboration or need for drawings.

It bears noting that after the piston-plunger 155 returns to its upward position, the dual support plate assembly 233 returns to the expanded condition as floating plate 230 returns upwards via the upwards biasing action of springs 232 acting on the floating plate as the springs expand.

Control System

In one embodiment, the foregoing method or process for operating agricultural sample packaging system 100 may be controlled by a microprocessor controlled processing system including programmable local machine controller 2811 and/or main system controller 2820.

Controller 2811 and/or controller 2820 is operably and communicably coupled and linked to all of the actuators, sensors, and other devices disclosed herein and programmable to execute suitable control logic/program instructions (e.g., software) to automatically control operation of the entire sample packaging system 100. In some embodiments, operation of the sample packing apparatus 110 may be initiated by one or more local actuators 2811*a*, 2811*b* (FIG. 22) which activates the controller 2811 and/or controller 2820 to start the sample packaging operations. These actuator switches are operably coupled to controller 2811 (which in turn is operably coupled to controller 2820 as further described below) and may be located anywhere on sample packaging apparatus 110.

Figure 2:
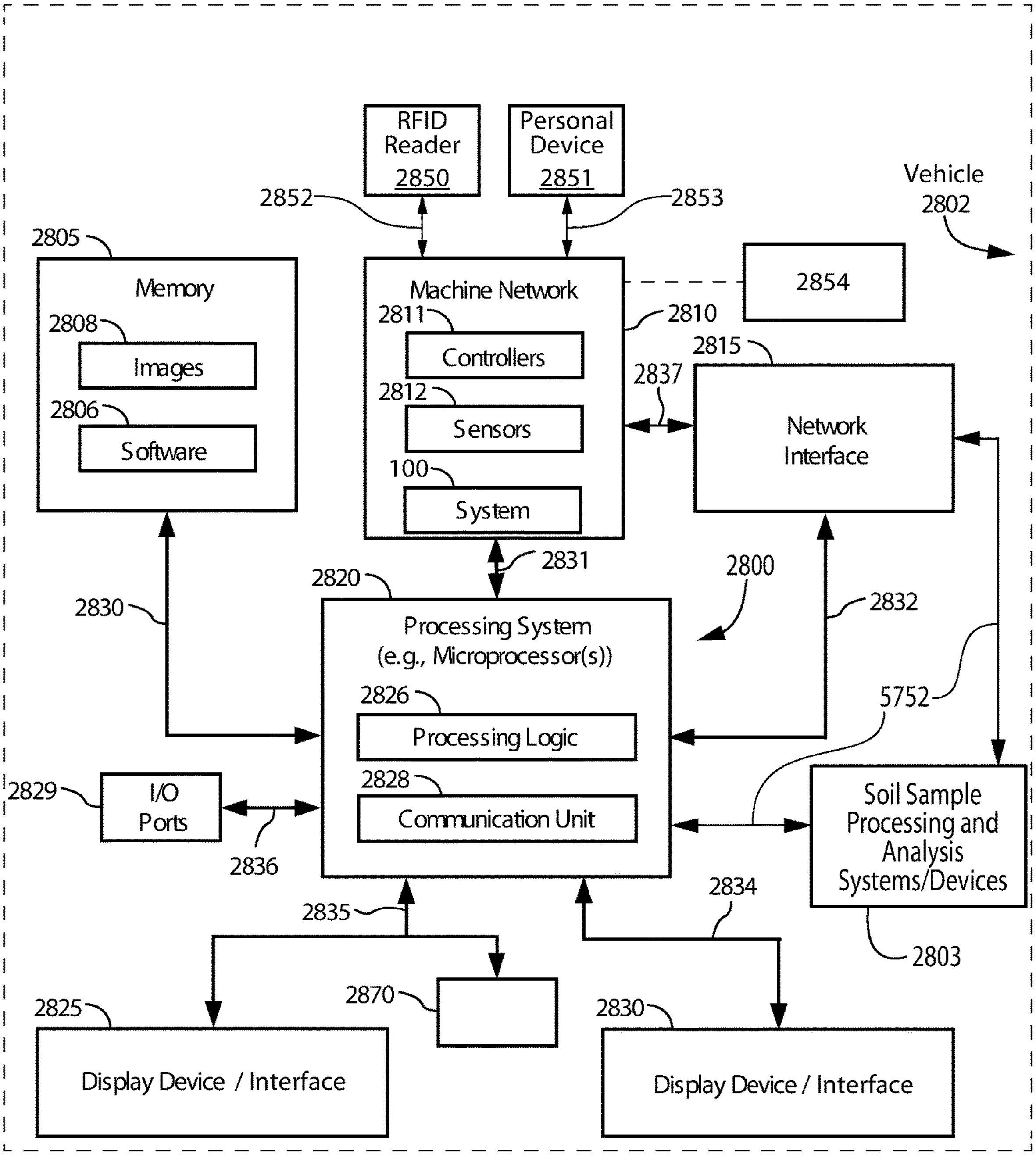
FIG. 2 is a schematic system diagram of a programmable processor-based central processing unit (CPU) or system controller for controlling the systems and apparatuses disclosed herein associated with the agricultural sample packaging system.
Figure 3:
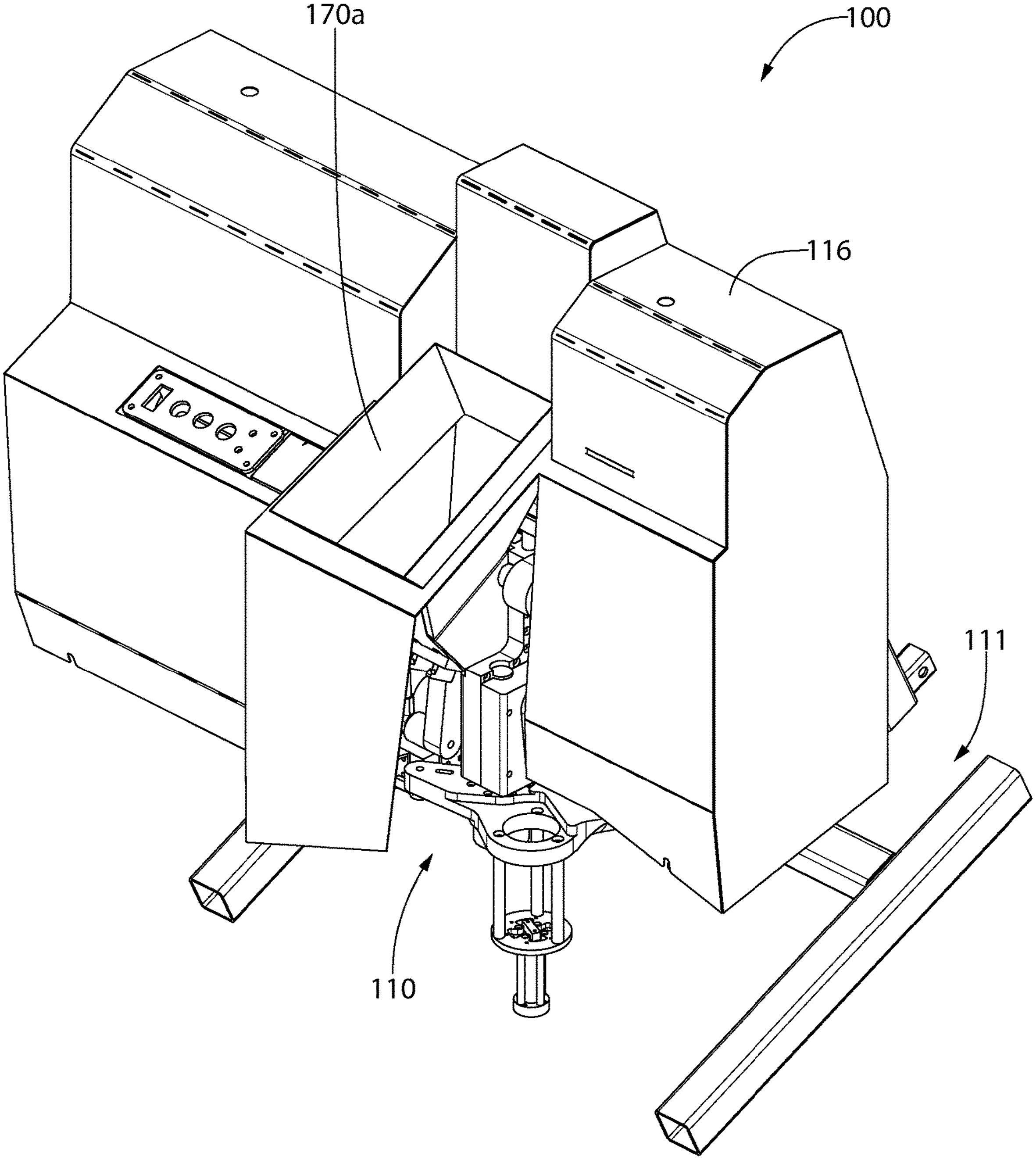
FIG. 3 is right top front perspective view of the sample packaging apparatus of the system.
Figure 4:
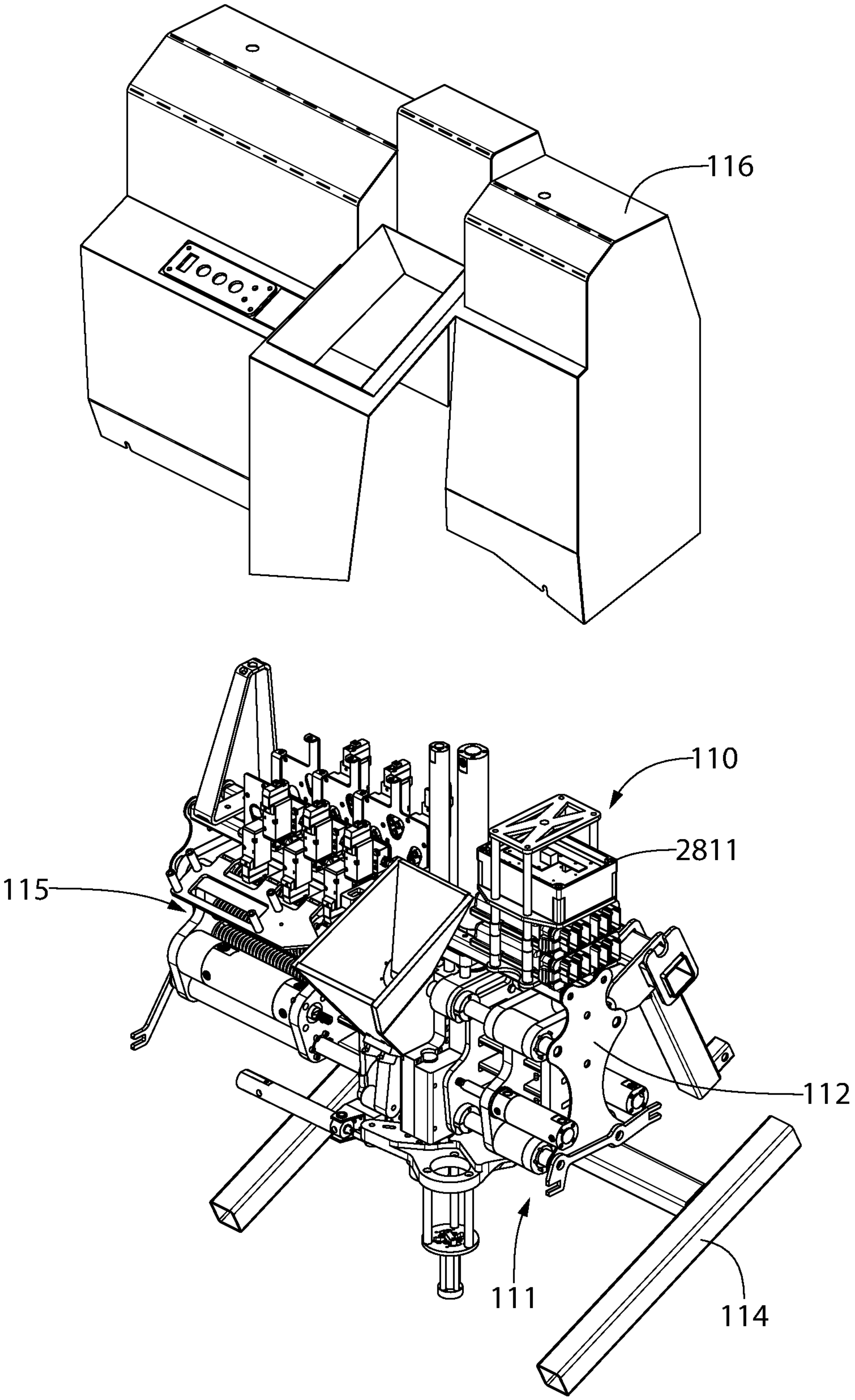
FIG. 4 is an exploded perspective view thereof showing the outer protective housing removed.
Figure 5:
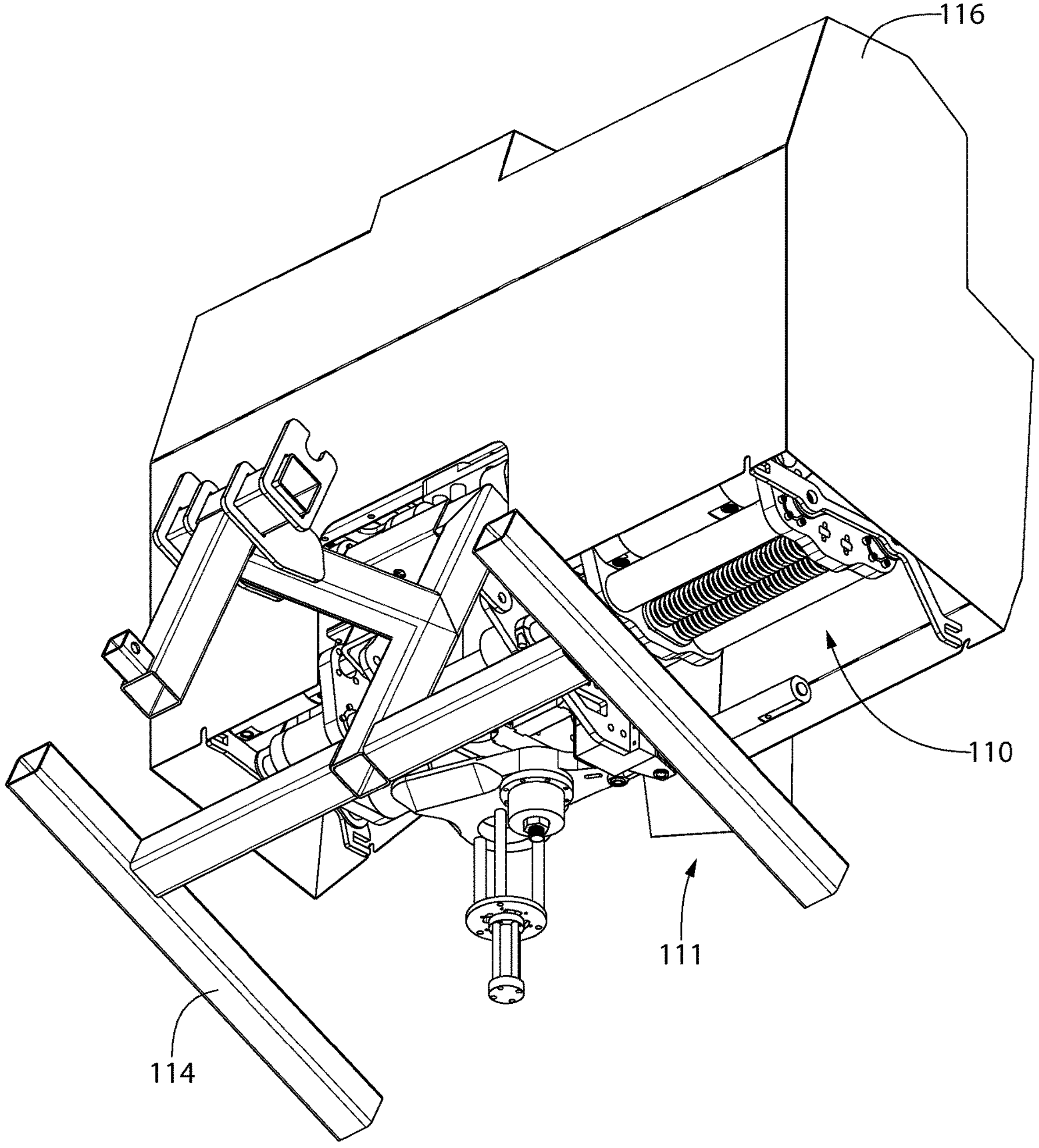
FIG. 5 is a bottom left rear perspective of the packaging apparatus.
Figure 6:
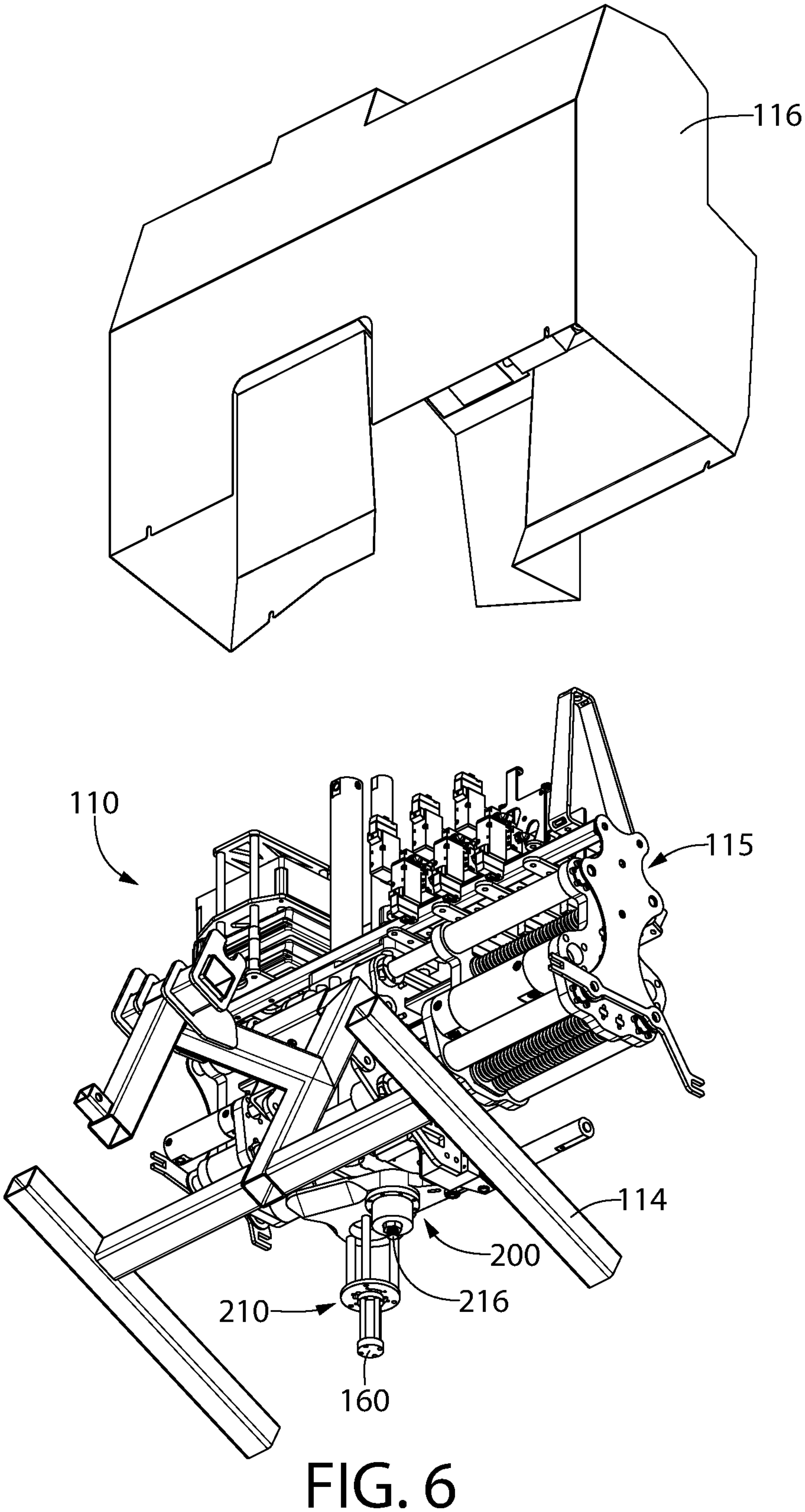
FIG. 6 is an exploded perspective view thereof.
Figure 7:
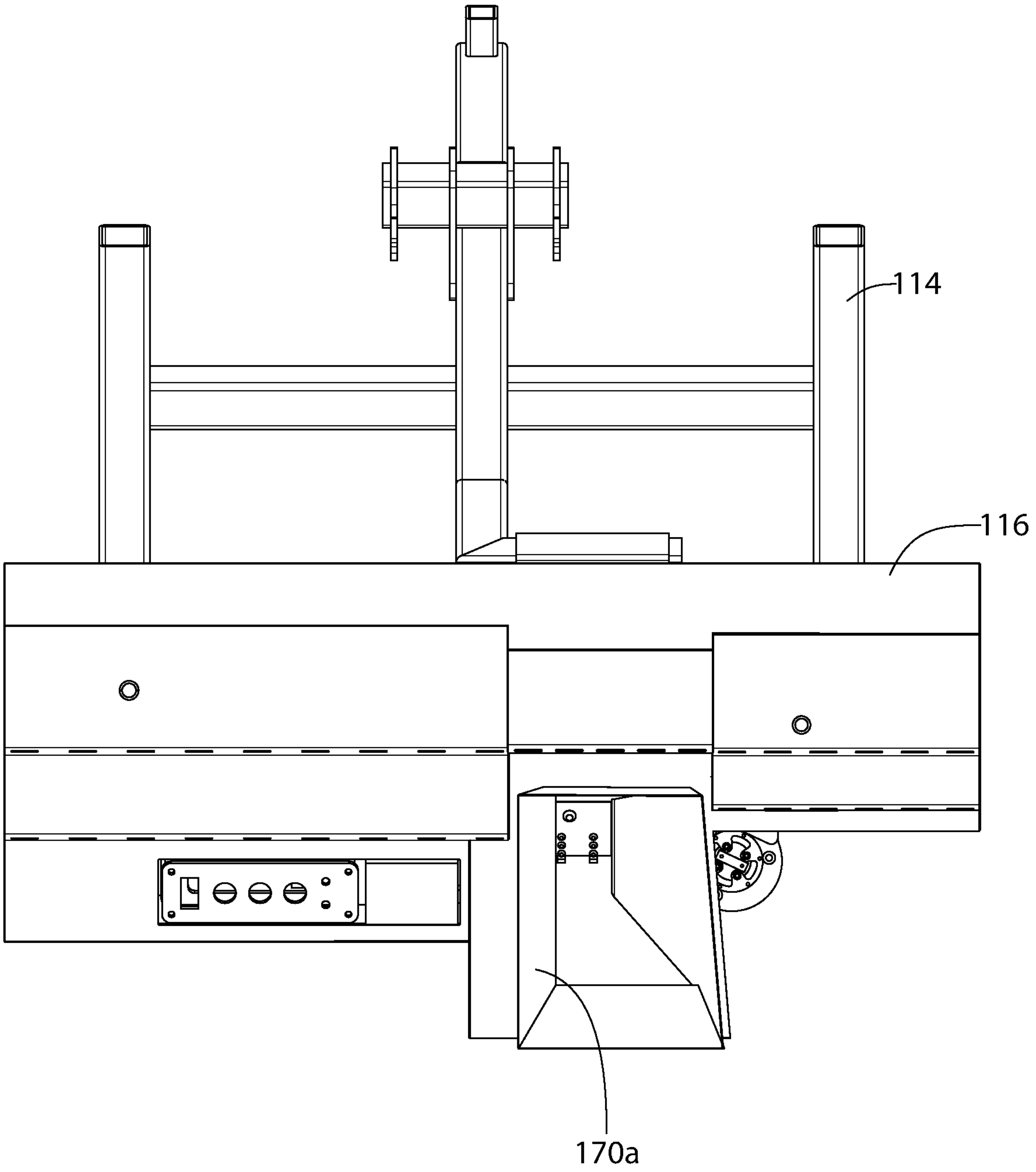
FIG. 7 is a top view of the packaging apparatus.
Figure 8:
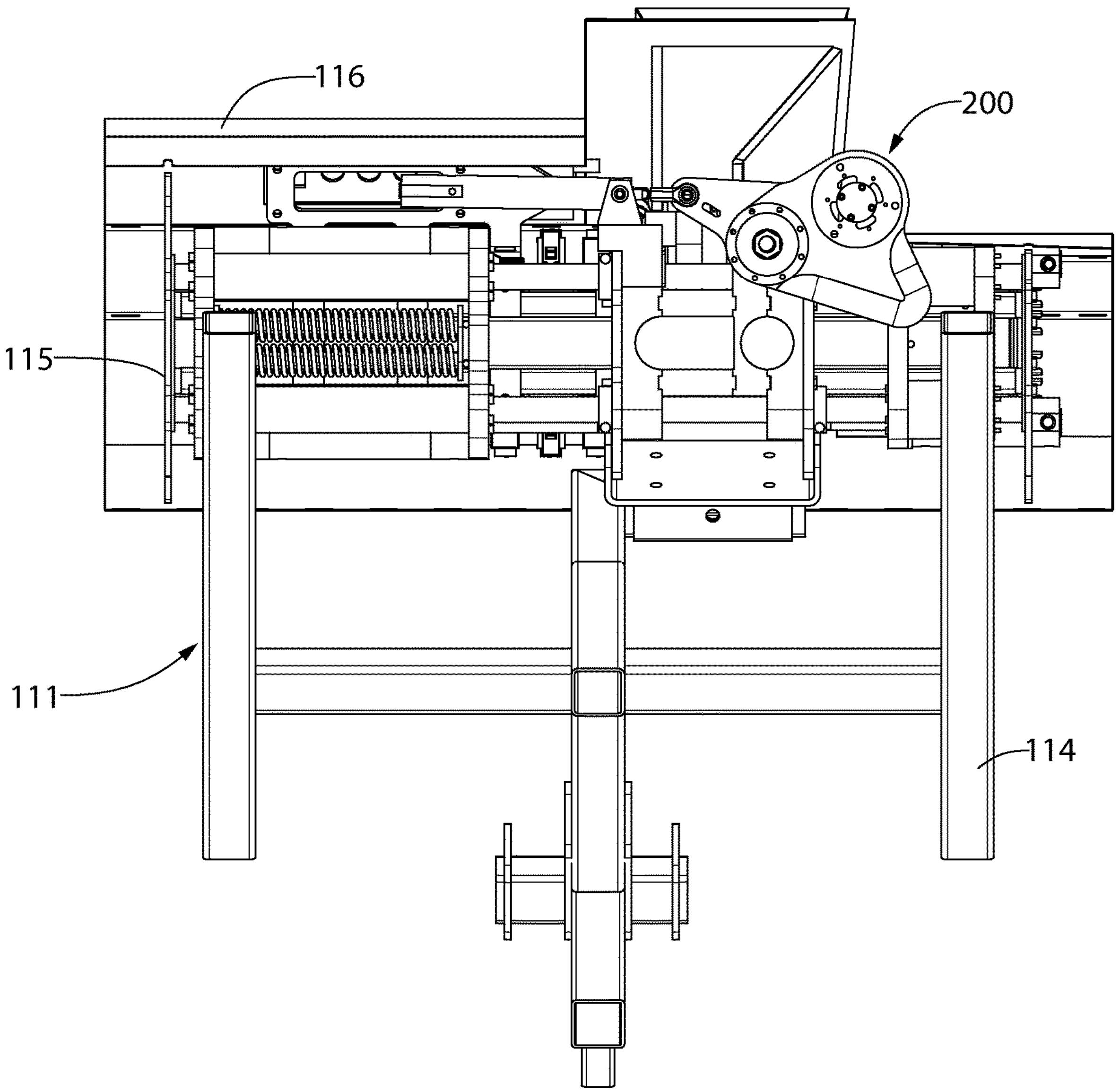
FIG. 8 is a bottom view thereof.
Figure 9:
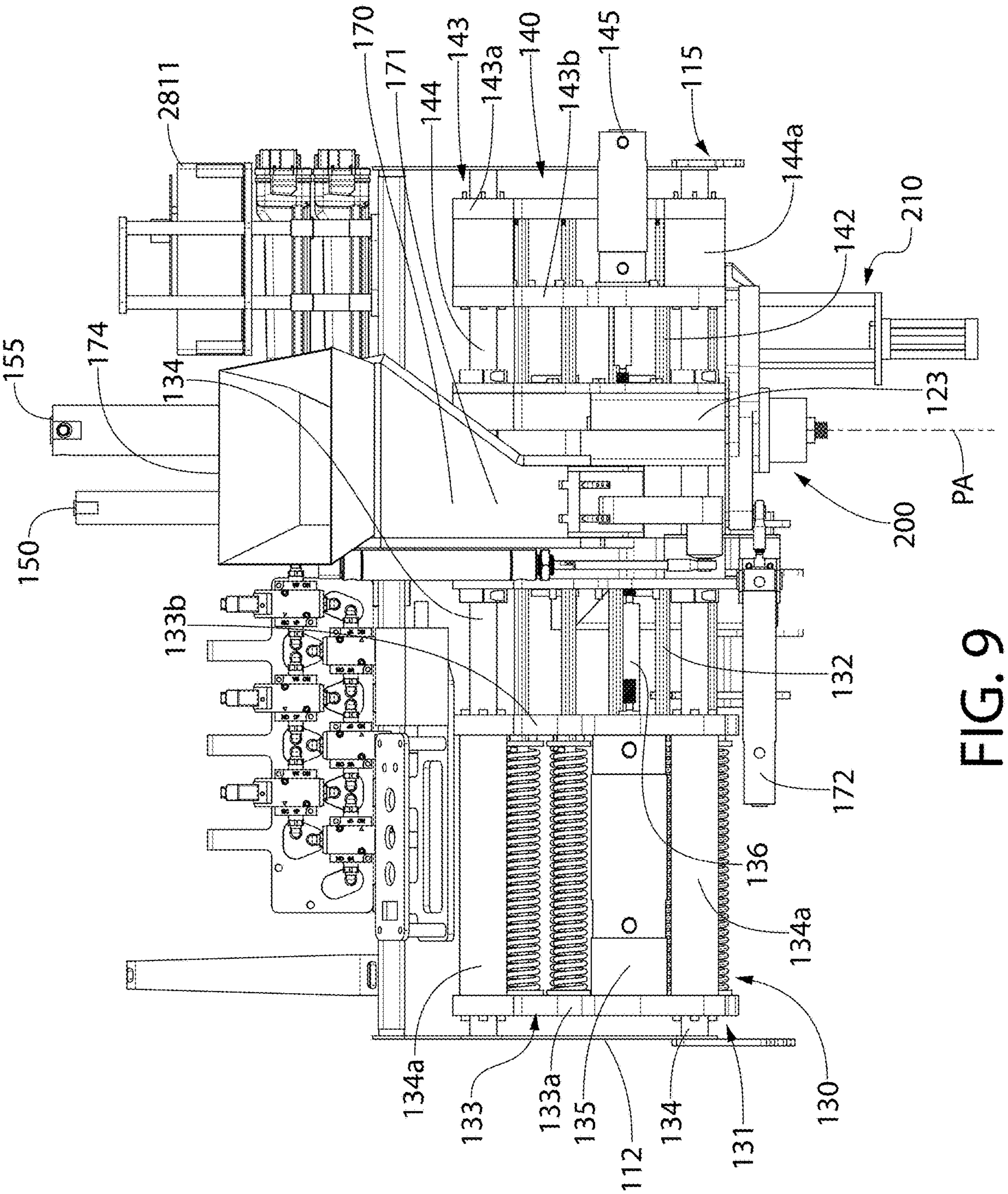
FIG. 9 is a front view thereof without the housing.
Figure 10:
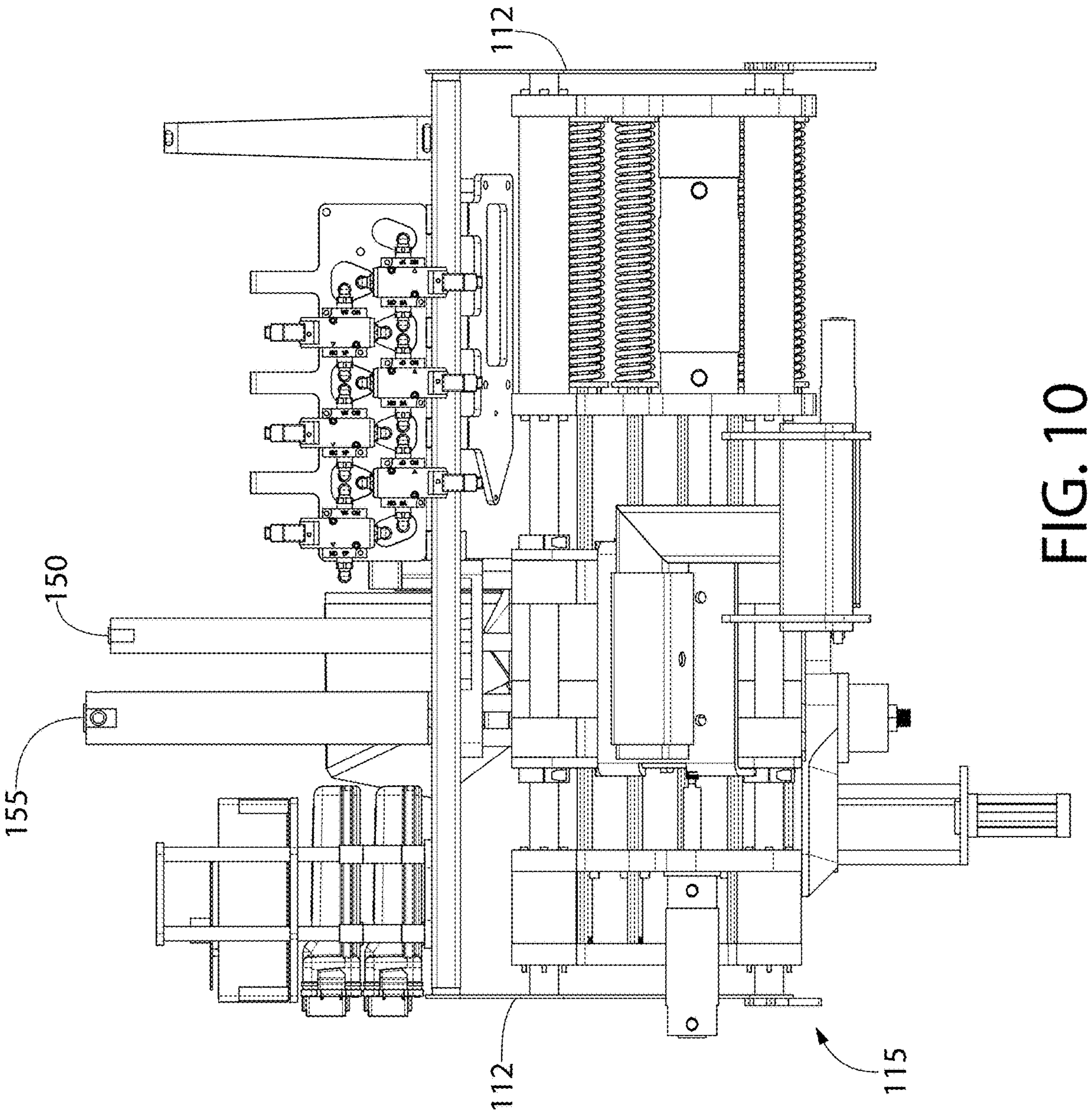
FIG. 10 is a rear view thereof.
Figure 11:
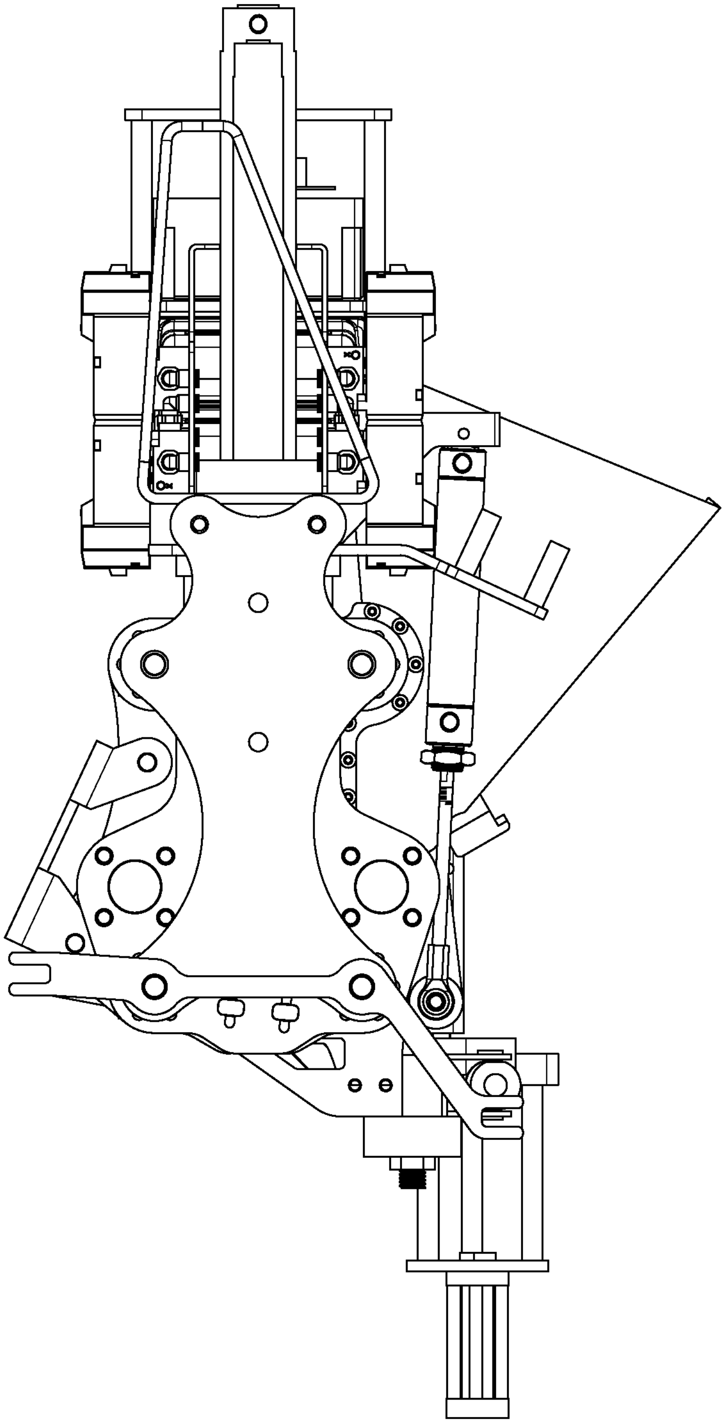
FIG. 11 is a right side view thereof.
Figure 12:
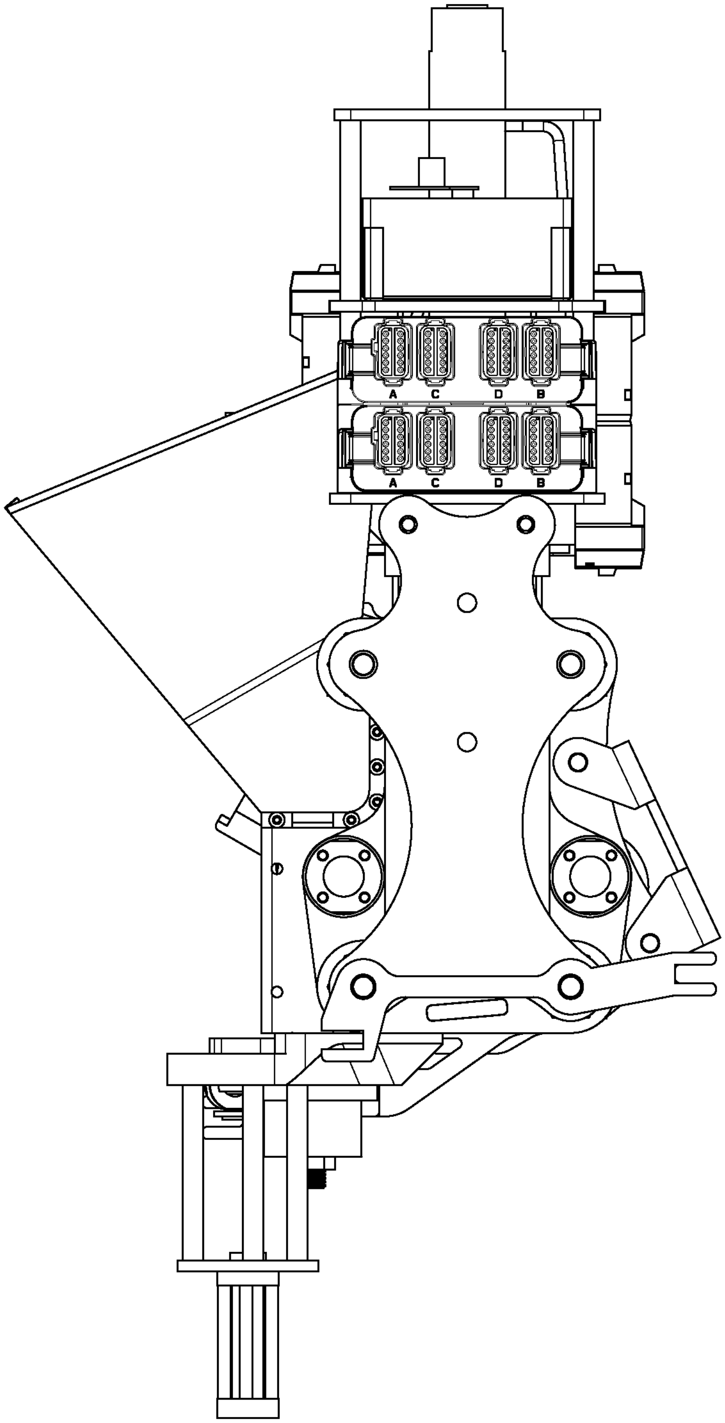
FIG. 12 is a left side view thereof.
Figure 13:
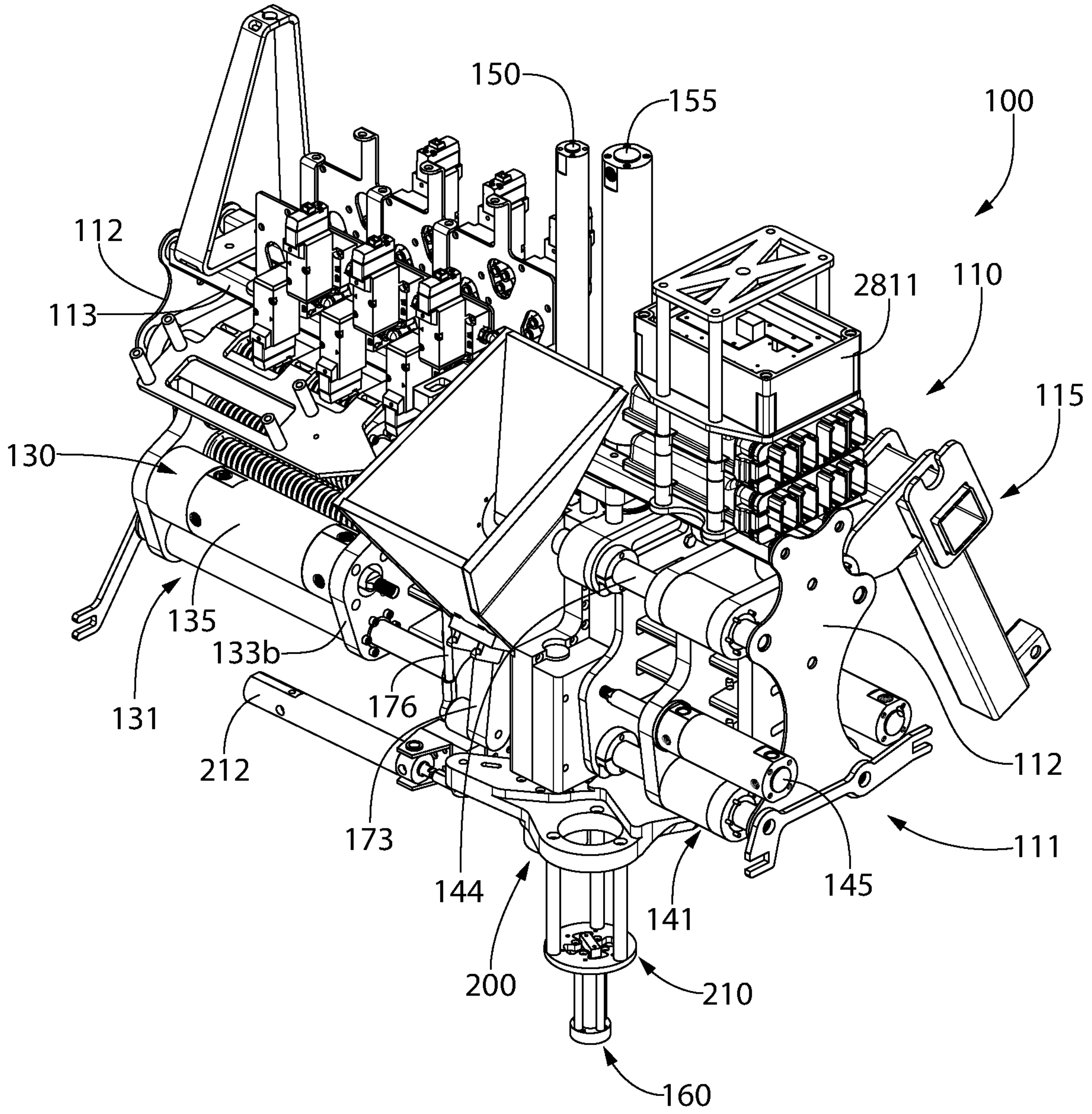
FIG. 13 is a top right front perspective view thereof.
Figure 14:
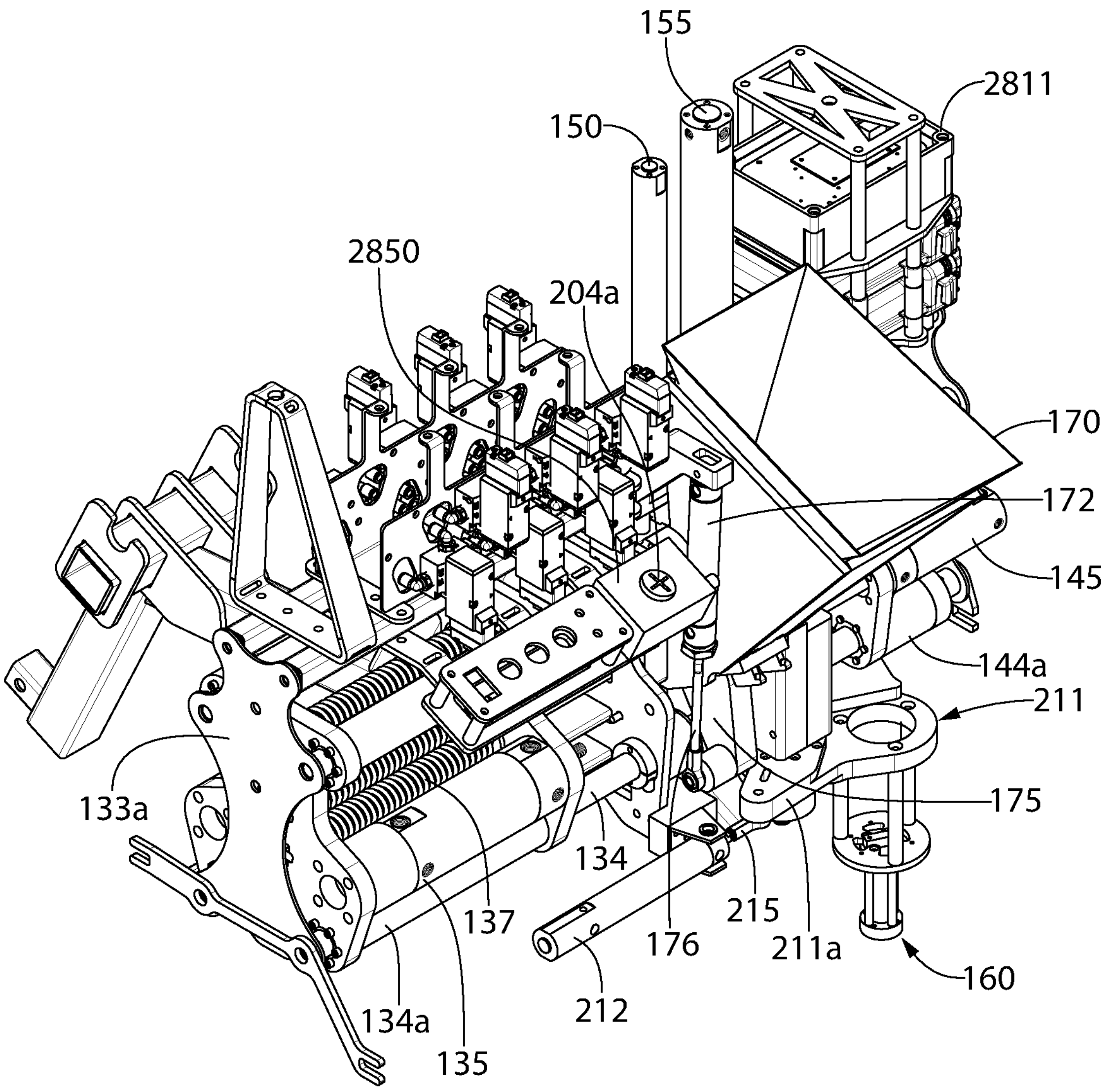
FIG. 14 is a top left rear perspective view thereof.
Figure 15:
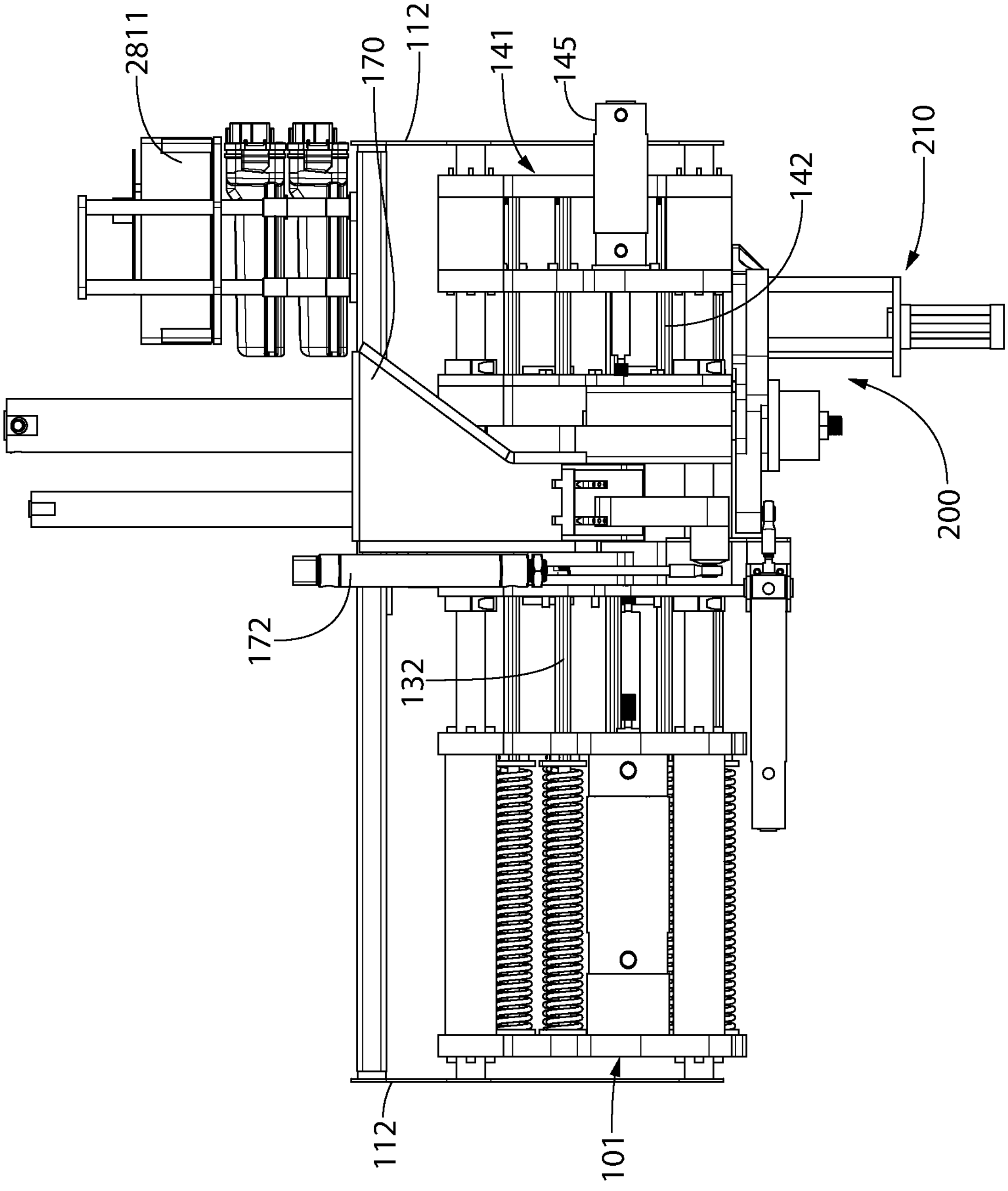
FIG. 15 is a front view thereof with some equipment removed to better show the sample blade mechanism components.
Figure 16:
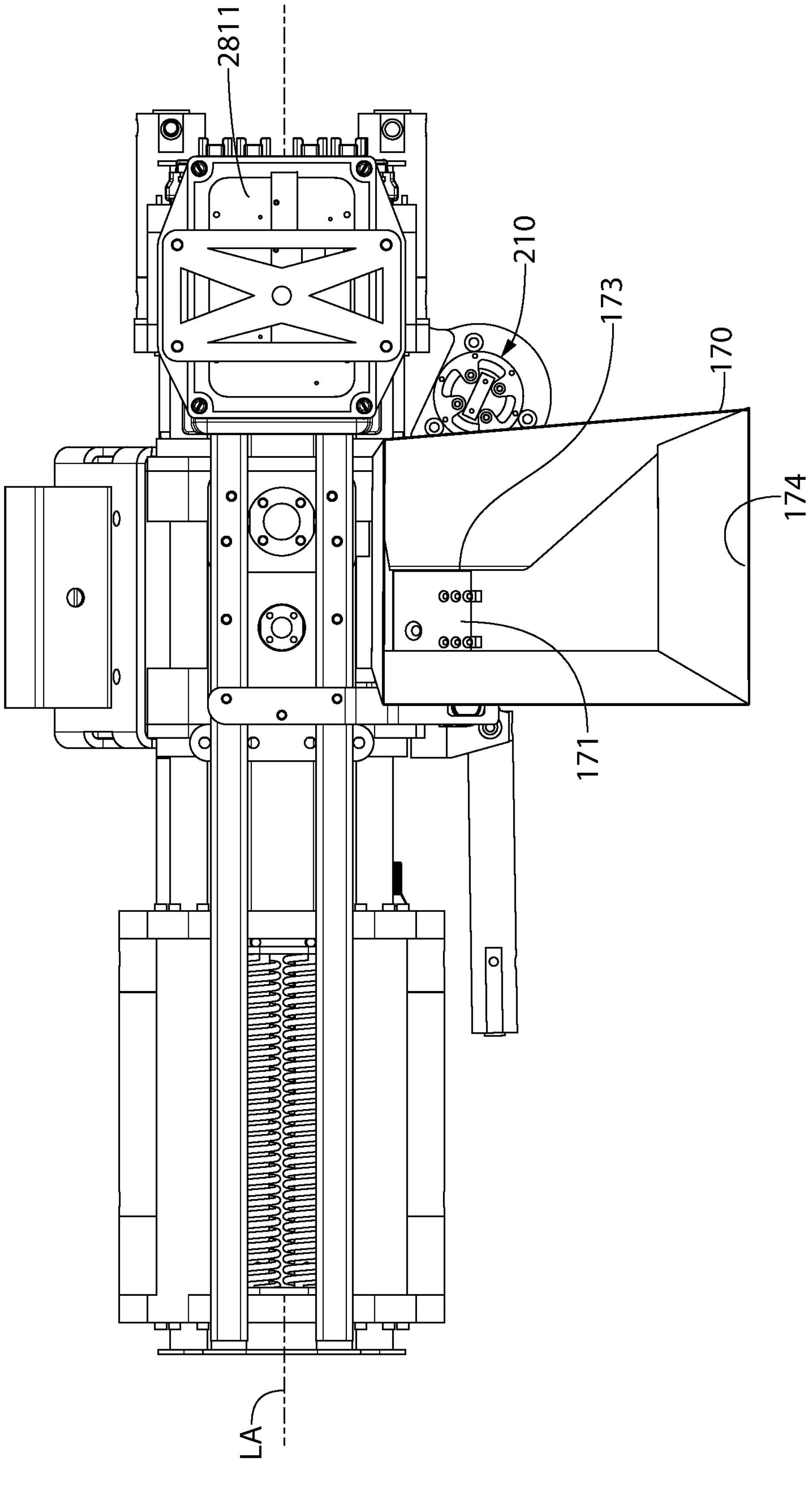
FIG. 16 is a top view thereof.
Figure 17:
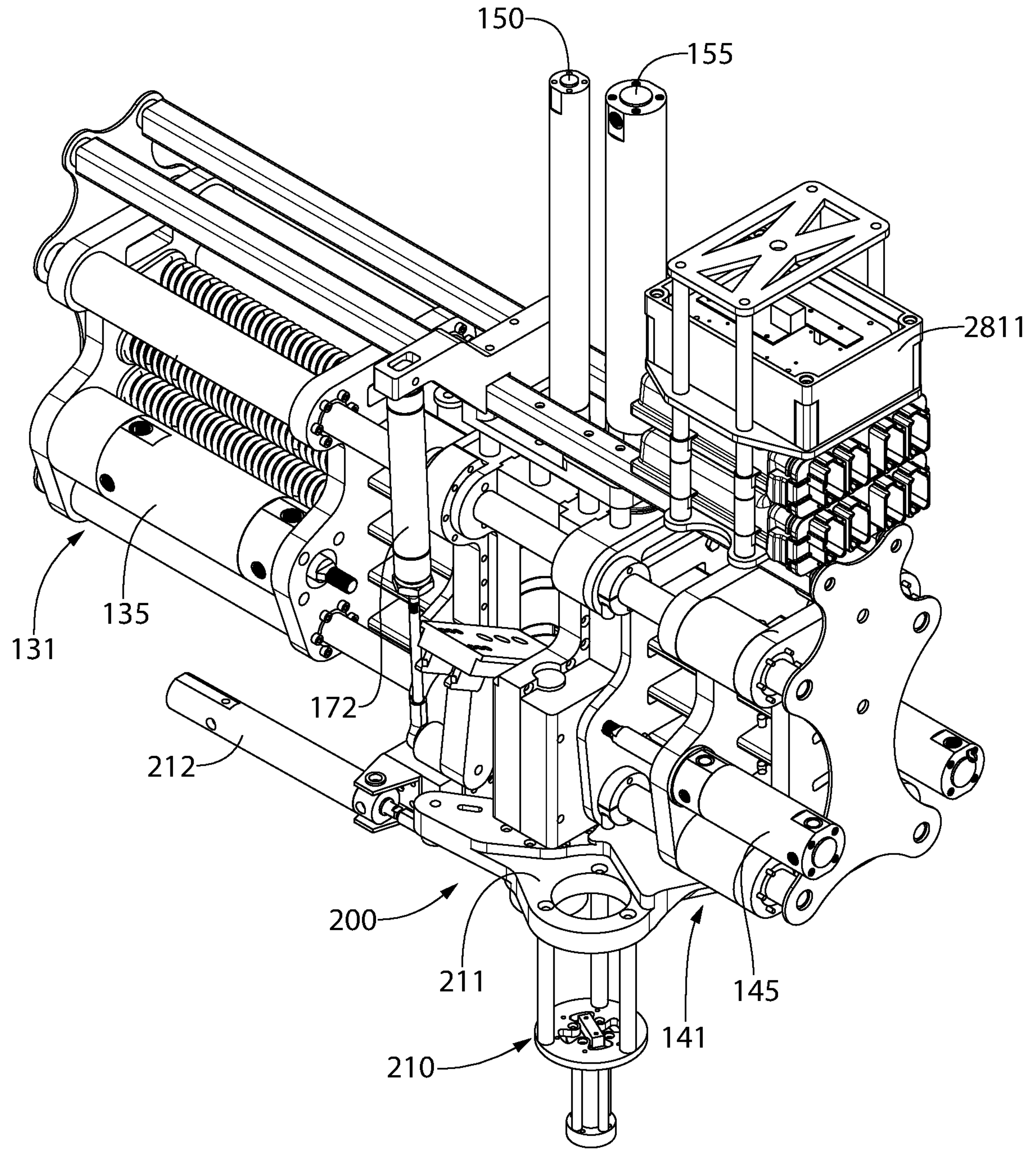
FIG. 17 is a right top front perspective view thereof.
Figure 18:
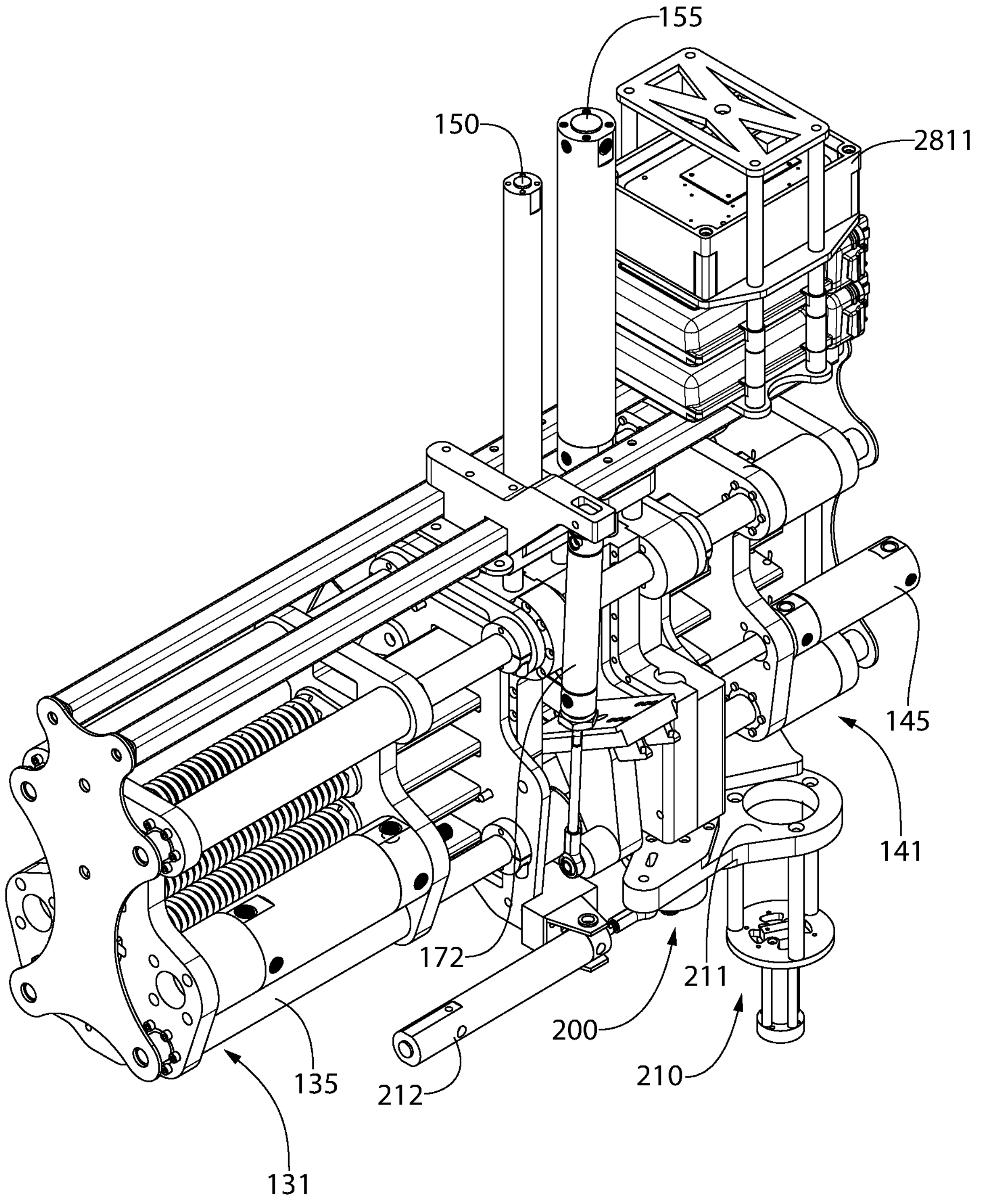
FIG. 18 is a left top front perspective view thereof.
Figure 19:
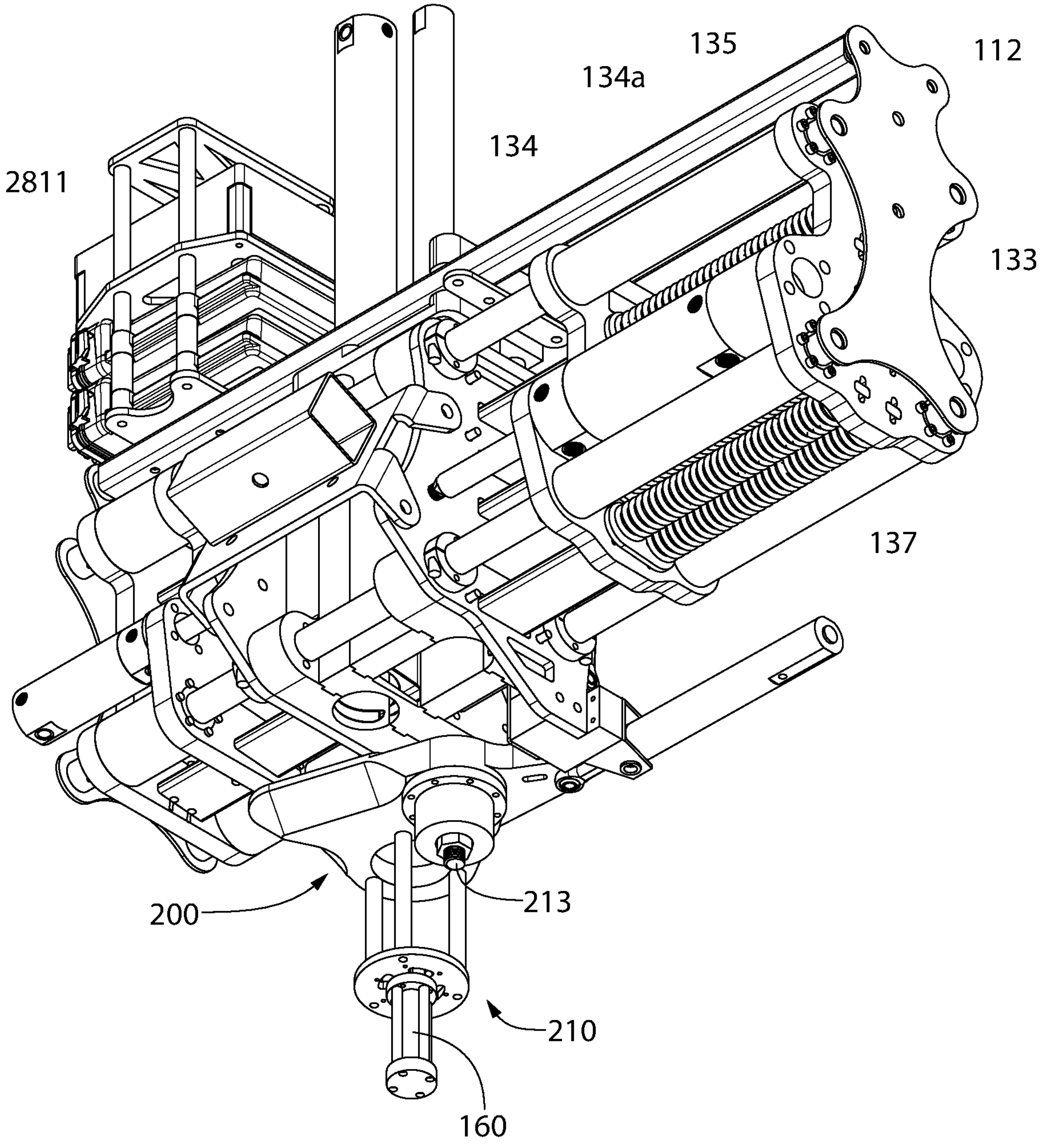
FIG. 19 is a left bottom rear perspective view with the lower portion of the apparatus support frame removed.

FIG. 2 is a high-level system block diagram showing the control system 2800 including programmable processor-based machine controller 2811 and main system controller 2820 referenced herein. System controller 2820 may include one or more processors, non-transitory tangible computer readable medium, programmable input/output peripherals, and all other necessary electronic appurtenances normally associated with a fully functional processor-based controller. Control system 2800, including controller 2820, is operably and communicably linked to the different soil sample processing and analysis systems and devices described elsewhere herein via suitable wired or wireless communication links to control operation of those systems and devices in a fully integrated and sequenced manner.

Referring to FIG. 2, the control system 2800 including programmable main system controller 2820 and/or local machine controller 2811 may be mounted on a translatable self-propelled or pulled vehicle 2802 (e.g., tractor, trailer, combine harvester, truck, ATV, etc.) including those disclosed in U.S. Application Nos. 3/260772 filed on 31 Aug. 2021; 63/260,776 filed on 31 Aug. 2021; and 63/260,777 filed on 31 Aug. 2021. The vehicle may be the same vehicle which collects the agricultural samples such as soil samples. In other embodiments, the controller may be part of a stationary workstation or facility. The sampling vehicle 2802 and its boundaries are designated by dashed box in FIG. 2 (those items within the box being mounted onboard the sampling vehicle in the illustrated embodiment). The packaging apparatus 110 may be mounted on the same vehicle 2802 or a stationary workstation as the main system controller 2820, or be separate therefrom. Local machine controller 2811 is mounted on packaging apparatus 110.

Main control system 2800 generally includes programmable controller 2820, non-transitory tangible computer or machine accessible and readable medium such as memory 2805, and a network interface 2815. Computer or machine accessible and readable medium may include any suitable volatile memory and non-volatile memory or devices operably and communicably coupled to the processor(s). Any suitable combination and types of volatile or non-volatile memory may be used including as examples, without limitation, random access memory (RAM) and various types thereof, read-only memory (ROM) and various types thereof, hard disks, solid-state drives, flash memory, or other memory and devices which may be written to and/or read by the processor operably connected to the medium.

Both the volatile memory and the non-volatile memory may be used for storing the program instructions or software. In one embodiment, the computer or machine accessible and readable non-transitory medium (e.g., memory 2805) contains executable computer program instructions which when executed by the system controller 2820 cause the system to perform operations or methods of the present disclosure including measuring properties and testing of soil and vegetative samples. While the machine accessible and readable non-transitory medium (e.g., memory 2805) is shown in an exemplary embodiment to be a single medium, the term should be taken to include a single medium or multiple media (e.g., a centralized or distributed database, and/or associated caches and servers) that store the one or more sets of control logic or instructions. The term "machine accessible and readable non-transitory medium" shall also be taken to include any medium that is capable of storing, encoding or carrying a set of instructions for execution by the machine and that cause the machine to perform any one or more of the methodologies of the present disclosure. The term "machine accessible and readable non-transitory medium" shall accordingly also be taken to include, but not be limited to, solid-state memories, optical and magnetic media, and carrier wave signals.

Network interface 2815 may be configured to communicate with the soil or other bulk agricultural material collection system on the vehicle which is retrieving samples (e.g., soil, etc.) from the agricultural field, and sample post-packaging/containerizing systems such as a sample slurry preparation, processing, and chemical analysis systems and devices (collectively represented by box 2803 in FIG. 2).

The agricultural sample packaging system 100 machine network 2810 can include at least one local microprocessor-based machine controller 2811 and a plurality of different type sensors 2812. Sensors 2812 may be operably and communicably linked to local machine controller 2811 and optionally system controller 2820 through controller 2811; each controller being configured to receive and send data/signals from/to the sensors. In some embodiments, packaging apparatus 110 with local machine controller 2811 mounted thereto may be one vehicle which traverses the agricultural field along with the bulk sample collection system and main system controller 2820 may be located on a remote separate vehicle or in a stationary location.

The sensors 2812 may include full sample tube sensor 220 previously described herein, and other linear positional or status sensors 2812*a* integrated with cap actuator 160, compaction and sample transfer piston-plungers 150 and 155 respectively, sample blade mechanism actuator 135, and cleaning blade mechanism 140 actuator 145 to apprise the system controller 2820 of the position or status of the those devices (e.g., piston-plungers up or down, sample and cleaning blades mechanism inserted or withdrawn from die block 124, etc.). The status sensors may also include accelerometers to provide feedback to the system controller 2820 that a device of the packaging system physically moved in response to an action/motion initiated by a control signal from the controller (e.g. sample and cleaning blades mechanism inserted/withdrawn, piston-plungers up/down, etc.). Geolocation tracking sensors such as GPS (global positioning system) may also be included if the sample packaging system is mounted on a vehicle which travels across the agricultural field. Accordingly, the control system knows the operational status, position, and condition of each of at least the major components of the agricultural sample packaging system 100 under its control at any given moment. This information is used by the machine network controller 2811 and/or system controller 2820 to automatically control the entire agricultural sample packing operations of the packaging apparatus 110 via machine network 2810, and detect if an operational malfunction of packaging apparatus has occurred. This is particularly useful if the apparatus 110 is being controlled from a remote location via a communicably linked laptop, tablet, cell phone, etc. In addition, the GPS sensor 2854 communicably linked to the packaging machine network 2810 as seen in FIG. 2 permits the machine and/or system controllers 2811, 2820 to pinpoint where in the agricultural field the soil sample was collected if the sample collection system equipment is used alongside the packaging apparatus 110 when the sample is collected and then packaged. The RFID tag associated with each packaged sample permits the associated GPS geolocation information to be tracked for each sample.

The local machine controller 2811 which may be mounted onboard packaging apparatus 110 controls operation of the agricultural sample packaging system 100 in cooperation with system controller 2820 in one embodiment. In other embodiments, machine controller 2811 may control operation of the packaging apparatus 110 alone via preprogrammed control logic/instructions if the controller is not linked to a main system controller 2820, or still be communicably coupled to the main system controller for data/information exchange and programming, but not for purposes of direct control of the sample packaging system components.

Local machine controller 2811 includes all of the usual appurtenances and auxiliary electronic devices similar to main system controller 2820 (e.g., memory, power supply, etc.) for forming a normal fully functional microprocessor-based control system configured to control operation of packaging apparatus 110.

With continuing reference to FIG. 2, the RFID scanner or reader 2850 previously described herein which is mounted on or may be nearby packaging apparatus 110 is operably and communicably coupled to packing system machine network 2810 via communication link 2852. Communication link 2852 may be wired or wireless. The unique RFID tag 2850*a* associated with each collected and packaged agricultural sample in sample tube 202 may be automatically scanned and read in one embodiment when end cap 204*a* which contains the tag is placed on the reader at the start of the sample tube filling operation. The tag may be read in some embodiments when the Fill Tube actuator 2811*a* is manually activated (e.g., pushed or thrown) by the packaging apparatus operator. This ensures that the correct geolocation is associated with the sample as the operator and vehicle should still be in the same physical location where the soil sample was collected from the agricultural field at that time. As previously described herein, the RFID tag may alternatively be located on the cylindrical body of the sample tube 202 or slideable plunger cap 204*b* inside the tube and read by controller 2811 of the machine network 2810. The unique sample ID information is transmitted to packaging system machine controller 2811, which may in turn may share that information with the main system controller 2820. The unique RFID tag associated with each sample tube 202 and its sample contents allows the sample to be tracked from initial packaging, other staging and processing of the sample pending chemical system, and finally chemical analysis. With use of the GPS information collected for with each sample that identifies the exact location in the agricultural field where the sample was collected, the chemical analysis results of the analytes of interest may be readily correlated back to a particular location or region in the field to determine the soil amendments necessary there.

The packaging system 100 may be locally controlled by machine controller 2811, which in turn is controlled and programmed by an personal electronic device (PED) 2851 with onboard microprocessor, memory, power supply, and all other usual auxiliary device and components associated with such devices. Such personal electronic devices 2851 may include for example without limitation a tablet, laptop, notebook, cell phone, and other similar devices located onboard vehicle 2802. Device 2851 acts as a user interface and input device which initiates automated operation of the agricultural sample packaging system 100 and packaging apparatus 110 via machine controller 2811. Personal electronic device 2851 may have a graphic user interface such as a touchscreen for such a purpose. Personal electronic device 2851 is operably and communicably coupled to packing system machine network 2810 via communication link 2853, which may be wired or wireless.

It bears noting that in embodiments where the entire agricultural sampling collection, packaging, and chemical analysis systems are mounted on a single field vehicle 2802 for in-situ analysis of the samples, the agricultural sample packaging system 100 may be controlled by the main system controller 2820 in lieu of a separate machine controller 2811. In such a case, the array of packaging system sensors 2812 may communicate directly with system controller 2820.

The network interface 2815 can be configured for wired and/or wireless bidirectional communications which may include at least one of a GPS transceiver, a WLAN transceiver (e.g., WiFi), an infrared transceiver, a Bluetooth transceiver, Ethernet, Near Field Communications, or other suitable communication interfaces and protocols for communications with the other devices and systems including the agricultural sample packaging system 100. The network interface 2815 may be integrated with the control system 2800 as illustrated in FIG. 2, the machine network 2810, or elsewhere. The I/O (input/output) ports 2829 of control system 2800 (e.g., diagnostic/on board diagnostic (OBD) port) enable communication with another data processing system or device (e.g., display devices, sensors, etc.).

The programmable controller 2820 may include one or more microprocessors, processors, a system on a chip (integrated circuit), one or more microcontrollers, or combinations thereof. The processing system includes processing logic 2826 for executing software instructions of one or more programs and a communication module or unit 2828 (e.g., transmitter, transceiver) for transmitting to and receiving communications from the machine network 2810 of sampling machine or vehicle 2802 via direct communication link 2831 or network interface 2815. The communication unit 2828 may be integrated with the control system 2800 (e.g. controller 2820) or be separate from the controller. In one embodiment, the communication unit 2828 may be in operable data communication with the machine/vehicle network 2810 via a diagnostic/OBD port of the I/O ports 2829.

Programmable processing logic or instructions 2826 of the control system 2800 which directs the operation of system controller 2820 including one or more processors may process the communications (i.e. data/information) received via the communication unit 2828 or network interface 2815 from the agricultural sample packaging system 100 including without limitation sensor associated with the status and operation of the packaging apparatus 110 and components thereof under the control of programmable system controller 2820. The memory 2805 of control system 2800 is configured for preprogrammed variable or setpoint/baseline values, storing collected data, and computer instructions or programs for execution (e.g. software 2806) used to control operation of the controller 2820, which in turn controls operation of packaging apparatus 110 and sample processing/analysis devices 2803. The memory 2805 can store, for example, software components such as testing software for analysis of soil and vegetation samples for performing operations of the present disclosure, or any other software application or module, images 2808 (e.g., captured images of crops), alerts, maps, etc. The system 2800 can also include an audio input/output subsystem (not shown) which may include a microphone and a speaker for, for example, receiving and sending voice commands or for user authentication or authorization (e.g., biometrics).

In some embodiments of agriculture sample packaging system 100 can further preferably include a sensing system 2812 comprising a plurality or array of different type sensors useful and associated with packaging and tracking the soil sample. The sensing system and its sensors are in data and control communication with packaging system machine controller 2811 and/or main system controller 2820. Other sensors which communicate with system controller 2820 may be associated with operation of the sample collection apparatus 8002 and components thereof including various equipment positional or orientation sensors, proximity sensors, etc. The agricultural material sample packaging system in combination with sensing system can provide complete automated control of the sample collection apparatus 8002 via the packaging system machine controller 2811 and/or main system controller 2820.

The main system controller 2820 communicates bi-directionally with memory 2805 via communication link 2830, machine or sample collection system network 2810 directly via communication link 2831 and/or alternatively via communication link 2837 associated with network interface 2815, the network interface 2815 via communication link 2832, display device 2830 and optionally a second display device 2825 via communication links 2834, 2835, and I/O ports 2829 via communication links 2836. System controller 2820 further communicates with the soil sample processing and analysis systems and devices 2803 via the wired/wireless communication links 5752 previously described herein via the network interface 2815 and/or directly as shown.

Display devices 2825 and 2830 can provide visual user interfaces for a user or human operator. The operator may be located onboard the mobile vehicle in one embodiment which traverses the agricultural field or at a remote operating position or station distal from the packaging apparatus 110. The display devices may include display controllers with onboard programmable microprocessors. In some embodiments, the computerized display device 2825 may therefore be a portable tablet device, cell phone, laptop, notebook, or other processor-based computing device with a touchscreen and/or keyboard (software based or physical hardware) that acts as an input/output device and which displays data (e.g., equipment status and position, and other relevant operational and maintenance information) and communicates with controller 2820. The computerized display device 2825 therefore receives input from the user or operator for controlling packaging apparatus 110.

The agricultural sample packaging system 100 disclosed herein is usable with and may form part of an overall agricultural sampling and analysis systems such as those described in U.S. Patent Application Publication No. 2018/0124992A1 and PCT Publication No. WO2020/012369, and other systems are described in U.S. Application Nos. 62/983,237, filed on 28 Feb. 2020; 63/017,789, filed on 30 Apr. 2020; 63/017,840, filed on 30 Apr. 2020; 63/018,120, filed on 30 April 2020; 63/018,153, filed on 30 Apr. 2020; 63/191,147, filed on 20 May 2021; 63/191,159, filed on 20 May 2021; 63/191,166, filed on 20 May 2021; 63/191,172, filed on 20 May 2021; Ser. No. 17/326,050, filed on 20 May 2021; 63/191,186, filed on 20 May 2021; 63/191,189, filed on 20 May 2021; 63/191,195, filed on 20 May 2021; 63/191,199, filed on 20 May 2021; 63/191,204, filed on 20 May 2021; Ser. No. 17/343,434, filed on 9 Jun. 2021; 63/208,865, filed on 9 Jun. 2021; Ser. No. 17/343,536, filed on 9 Jun. 2021; 63/213,319, filed on 22 Jun. 2021; 63/260,772, filed on 31 Aug. 2021; 63/260,776, filed on 31 Aug. 2021; 63/260,777, filed on 31 Aug. 2021; 63/245,278, filed on 17 Sep. 2021; 63/264,059, filed on 15 Nov. 2021; 63/264,062, filed on 15 Nov. 2021; 63/264,065, filed on 15 Nov. 2021; 63/268,418, filed on 23 Feb. 2022; 63/268,419, filed on 23 Feb. 2022; 63/268,990, filed on 8 Mar. 2022; 63/269,060, filed 9 Mar. 2022; 63/269,064, filed 9 Mar. 2022; 63/365,243, filed 24 May 2022; 63/365,244, filed 24 May 2022; 63/366,673, filed 20 Jun. 2022; 63/366,674, filed 20 Jun. 2022; 63/369,722, filed 28 Jul. 2022; 63/369,724, 28 Jul. 2022; 63/369,765, filed 28 Jul. 2022; 63/369,988, filed 1 Aug. 2022; 63/370,072, filed 1 Aug. 2022; 63/370,077, filed 1 Aug. 2022; 63/370,081, filed 1 Aug. 2022; and PCT/IB2021/051076, filed on 10 Feb. 2021; PCT Application Nos. PCT/IB2021/051077, filed on 10 Feb. 2021; PCT/IB2021/052872, filed on 7 Apr. 2021; PCT/IB2021/052874, filed on 7 Apr. 2021; PCT/IB2021/052875, filed on 7 Apr. 2021; PCT/IB2021/052876, filed on 7 Apr. 2021. Other sampling systems are described in U.S. Application Nos. 62/983,237, filed on 28 Feb. 2020; 63/017,789, filed on 30 Apr. 2020; 63/017,840, filed on 30 Apr. 2020; 63/018,120, filed on 30 Apr. 2020; 63/018,153, filed on 30 Apr. 2020; PCT/IB2021/051076, filed on 10 Feb. 2021; and PCT Application Nos. PCT/IB2021/051077, filed on 10 Feb. 2021; PCT/IB2021/052872, filed on 7 Apr. 2021; PCT/IB2021/052874, filed on 7 Apr. 2021; PCT/IB2021/052875, filed on 7 Apr. 2021; PCT/IB2021/052876, filed on 7 Apr. 2021.

Examples

The following are non-limiting examples.

Example 1—an agricultural sample packaging apparatus comprising: a bulk material chamber configured for receiving a sample; a sample collection chamber; a die block disposed between the bulk material and sample collection chambers, the die block including a plurality of through die slots in communication with the bulk material and sample collection chambers; a sample blade mechanism comprising a plurality of elongated sample blades movably insertable through the bulk material chamber and die slots from a first side of the die block, wherein the sample blades are operable to extrude the sample from the bulk material chamber through the die slots and into the sample collection chamber.

Example 2—the apparatus according to Example 1, wherein the apparatus comprises a rotatable carousel including a container holder configured to removably hold a sample container.

Example 3—the apparatus according to Example 2, wherein the carousel is rotatable between an inward closed position in which the sample container is positioned beneath the sample collection chamber and an outward open position in which the sample container is not beneath the sample collection chamber.

Example 4—the apparatus according to any one of Examples 2 to 3, wherein the apparatus comprises a cleaning blade mechanism comprising a plurality of elongated cleaning blades movably insertable through the sample collection chamber and die slots from a second side of the die block.

Example 5—the apparatus according to any one of Examples 2 to 4, further comprising a compaction piston-plunger configured to compress the sample in the bulk material chamber.

Example 6—the apparatus according to Example 5, further comprising a sample transfer piston-plunger configuration to force the sample downwards and outwards from the sample collection chamber.

Example 7—the apparatus according to any one of Examples 2 to 6, further comprising a programmable controller configured to control operation of the sample packaging apparatus.

Example 8—the apparatus according to any one of Examples 2 to 7, wherein the sample is soil.

Example 9—the apparatus according to any one of Examples 2 to 8, wherein the apparatus comprises a support frame configured for mounting to a mobile vehicle.

Example 10—the apparatus according to Example 1, wherein each of the sample blades comprises a compression spring.

Example 11—the apparatus according to Example 10, wherein each sample blade comprises a bifurcated end comprising a pair of the springs which act on a pair of spaced apart spring plates coupled to each sample blade.

Example 12—a method for packaging an agricultural sample comprising: adding a sample to a bulk material chamber; inserting a plurality of sample blades through the bulk material chamber; forcing the sample through a die block with the sample blades forming sample material plugs; and collecting the sample material plugs in a sample collection chamber.

Example 13—the method according to Example 12, further comprising before the insertion step, a step of rotating a carousel holding a sample container and positioning the sample container beneath the sample collection chamber.

Example 14—the method according to Example 13, further comprising depositing the sample material plugs in the sample container.

While the foregoing description and drawings represent some example systems, it will be understood that various additions, modifications and substitutions may be made therein without departing from the spirit and scope and range of equivalents of the accompanying claims. In particular, it will be clear to those skilled in the art that embodiments of the present disclosure may be embodied in other forms, structures, arrangements, proportions, sizes, and with other elements, materials, and components, without departing from the spirit or essential characteristics thereof. In addition, numerous variations in the methods/processes described herein may be made. One skilled in the art will further appreciate that the embodiments of the present disclosure may be used with many modifications of structure, arrangement, proportions, sizes, materials, and components and otherwise, used in the practice of the embodiments of the present disclosure, which are particularly adapted to specific environments and operative requirements without departing from the principles of the present embodiments of the present disclosure. The presently disclosed embodiments are therefore to be considered in all respects as illustrative and not restrictive, the scope of the embodiments of the present disclosure being defined by the appended claims and equivalents thereof, and not limited to the foregoing description or embodiments. Rather, the appended claims should be construed broadly, to include other variants and embodiments, which may be made by those skilled in the art without departing from the scope and range of equivalents of the embodiments of the present disclosure.

What is claimed is:

1. An agricultural sample packaging apparatus comprising:

- a bulk material chamber configured for receiving a sample;
- a sample collection chamber;
- a die block disposed between the bulk material and sample collection chambers and forming a fixed wall relative to the bulk material and sample collection chambers, the die block including a plurality of through die slots in communication with the bulk material and sample collection chambers; and
- a sample blade mechanism comprising a plurality of elongated sample blades movably insertable through the bulk material chamber and die slots from a first side of the die block;
- wherein the sample blades are operable to extrude the sample from the bulk material chamber through the die slots and into the sample collection chamber.

2. The apparatus according to claim 1, wherein the apparatus comprises a rotatable carousel including a container holder configured to removably hold a sample container.

3. The apparatus according to claim 2, wherein the carousel is rotatable between an inward closed position in which the sample container is positioned beneath the sample collection chamber and an outward open position in which the sample container is not beneath the sample collection chamber.

4. The apparatus according to claim 2, wherein the apparatus comprises a cleaning blade mechanism comprising a plurality of elongated cleaning blades movably insertable through the sample collection chamber and die slots from a second side of the die block.

5. The apparatus according to claim 2, further comprising a compaction piston-plunger configured to compress the sample in the bulk material chamber.

6. The apparatus according to claim 5, further comprising a sample transfer piston-plunger configuration to force the sample downwards and outwards from the sample collection chamber.

7. The apparatus according to claim 2, further comprising a programmable controller configured to control operation of the sample packaging apparatus.

8. The apparatus according to claim 2, wherein the sample is soil.

9. The apparatus according to claim 1, wherein each of the sample blades comprises a compression spring.

10. The apparatus according to claim 9, wherein each sample blade comprises a bifurcated end comprising a pair of the springs which act on a pair of spaced apart spring plates coupled to each sample blade.

11. The apparatus according to claim 1, wherein each of the plurality of through die slots extends completely through the die block from the bulk material chamber to the sample collection chamber.

12. A method for packaging an agricultural sample comprising:

- adding a sample to a bulk material chamber;
- inserting a plurality of sample blades through the bulk material chamber;
- forcing the sample through a die block with the sample blades forming sample material plugs; and
- collecting the sample material plugs in a sample collection chamber;
- wherein the die block is disposed between the bulk material chamber and the sample collection chamber and forming a fixed wall relative to the bulk material and sample collection chambers.

13. The method according to claim 12, further comprising before the insertion step, a step of rotating a carousel holding a sample container and positioning the sample container beneath the sample collection chamber.

14. The method according to claim 13, further comprising depositing the sample material plugs in the sample container.

15. The method according to claim 13, wherein the die block further comprises a plurality of through die slots in communication with the bulk material chamber, and the method further comprises, after the collecting step, a step for cleaning the plurality of through die slots via inserting a plurality of cleaning blades into the plurality of through die slots.

16. The method according to claim 13, wherein each of the plurality of sample blades comprises a bifurcated end comprising a pair of springs which act on a pair of spaced apart spring plates coupled to each sample blade.

17. An agricultural sample packaging apparatus comprising:

- a bulk material chamber configured for receiving a sample;
- a sample collection chamber;

a die block disposed between the bulk material and sample collection chambers, the die block including a plurality of through die slots in communication with the bulk material and sample collection chambers;

a sample blade mechanism comprising a plurality of elongated sample blades movably insertable through the bulk material chamber and die slots from a first side of the die block; and a cleaning blade mechanism comprising a plurality of elongated cleaning blades movably insertable through the sample collection chamber and die slots from a second side of the die block;

wherein the sample blades are operable to extrude the sample from the bulk material chamber through the die slots and into the sample collection chamber.

18. The apparatus according to claim 17, further comprising a compaction piston-plunger configured to compress the sample in the bulk material chamber.

19. The apparatus according to claim 18, further comprising a sample transfer piston-plunger configuration to force the sample downwards and outwards from the sample collection chamber.

20. An agricultural sample packaging apparatus comprising:

a bulk material chamber configured for receiving a sample;

a sample collection chamber;

a die block disposed between the bulk material and sample collection chambers and forming a part of the bulk material chamber and a part of the sample collection chamber, the die block including a plurality of through die slots in communication with the bulk material and sample collection chambers; and a sample blade mechanism comprising a plurality of elongated sample blades movably insertable through the bulk material chamber and die slots from a first side of the die block;

wherein the sample blades are operable to extrude the sample from the bulk material chamber through the die slots and into the sample collection chamber.

* * * * *